(12) United States Patent
Birnie

(10) Patent No.: US 8,802,619 B2
(45) Date of Patent: Aug. 12, 2014

(54) CANCER VACCINE

(75) Inventor: Richard Birnie, York (GB)

(73) Assignee: The University of York, York (GB)

(*) Notice: Subject to any disclaimer, the term of this patent is extended or adjusted under 35 U.S.C. 154(b) by 0 days.

(21) Appl. No.: 13/379,957

(22) PCT Filed: Jun. 22, 2010

(86) PCT No.: PCT/GB2010/001225
§ 371 (c)(1),
(2), (4) Date: Dec. 21, 2011

(87) PCT Pub. No.: WO2010/149963
PCT Pub. Date: Dec. 29, 2010

(65) Prior Publication Data
US 2012/0100102 A1 Apr. 26, 2012

(30) Foreign Application Priority Data

Jun. 23, 2009 (GB) .................................. 0910751.7

(51) Int. Cl.
*C07K 14/00* (2006.01)
*C07H 21/02* (2006.01)
(52) U.S. Cl.
USPC .............................. 514/1; 530/350; 536/23.1
(58) Field of Classification Search
USPC ................................ 514/1; 530/350; 536/23.1
See application file for complete search history.

(56) References Cited

U.S. PATENT DOCUMENTS

| 2003/0124529 A1 | 7/2003 | Oxvig |
| 2005/0009136 A1 | 1/2005 | Nixon |

FOREIGN PATENT DOCUMENTS

| AU | 2009200138 | 2/2009 |
| WO | 2007012811 | 2/2007 |
| WO | 2007015171 | 2/2007 |
| WO | 2008090355 | 2/2008 |

OTHER PUBLICATIONS

Taylor. 1995; Cytokines as adjuvants for vaccines: Anigen-specific responses differ from polyclonal responses. Infection and Immunity. 63(9): 3241-3244.*
Weiner et al. 1997; Immunostimulatory oligodeoxynucleotides containing the CpG motif are effective as immune adjuvants in tumor antigen immunization. PNAS 94: 10833-10837.*
Parant. 1979; Biologic properties of a new synthetic adjuvant, muramyl dipeptide (MDP). Springer Seminars in Immunopathology. 2: 101-118.*
Qin et al. 1997; Double-monoclonal immunofluorometric assays for pregnancy-associated plasma protein A/proeosinophil major basic protein (PAPP-A/proMBP) complex in first-trimester maternal serum screening for Down Syndrome. Clinical Chemistry 43 (12): 2323-2332.*
Lubaroff, et al., "CpG oligonucleotide as an adjuvant for the treatment of prostate cancer.", Adv. Drug Deliv. Rev., 61(3):268-74 (2009).
Roos, et al., "DNA vaccination for prostate cancer", Methods Mol. Biol., 423:463-72 (2008).
Ryan, et al., "Expression of a protease-resistant insulin-like growth factor-binding protein-4 inhibits tumor growth in a murine model of breast cancer", Br. J. Cancer, 101(2):278-86 (2009).
Saffran, et al., "Target antigens for prostate cancer immunotherapy", Cancer Metastasis Rev., 18(4):437-49 (1999).
Suzuki, et al., "Bikunin target genes in ovarian cancer cells identified by microarray analysis", J Biol. Chem., 278 (17):14640-6 (2003).
Tanaka, et al., "Genetic downregulation of pregnancy-associated plasma protein-A (PAPP-A) by bikunin reduces IGF-I-dependent Akt and ERK1/2 activation and subsequently reduces ovarian cancer cell growth, invasion and metastasis", Int. J Cancer, 109(3):336-47 (2004).
Zimmermann, et al., "Immunostimulatory DNA as adjuvant: efficacy of phosphodiester CpG oligonucleotides is enhanced by 3' sequence modifications", Vaccine, 21(9-10):990-5 (2003).
International Search Report and written opinion in corresponding PCT Application PCT/GB2010/001225, mailed Oct. 5, 2010.

* cited by examiner

*Primary Examiner* — Karen Cochrane Carlson
(74) *Attorney, Agent, or Firm* — Pabst Patent Group LLP

(57) ABSTRACT

We disclose a vaccine comprising a pappalysin and vaccine compositions comprising a pappalysin.

11 Claims, 24 Drawing Sheets

Figure 1

```
   1 atgggctct ggagttggt gctgcactg gggctgctga gcgcgcgct gggctgcagg
  61 ctggcgaga gtcccgccg ggccggaga gaccgcggg ccggccgacc ccgcgccc
 121 gccgccggcc cggccacctg cgccacccgg gcgccgcg gccgccgcga ctgccgccg
 181 ccgccgggcg cgccgggcg tgcctggaa gccgtgcgcg tccccggcg gcggcagcag
 241 cggaggcga gggcgccac cgaggagcg agcccgccga gccggcgct ctattcagc
 301 gcgggaggcg agcagtgcg cctgcgggcc gacctcgagc tgcccggga cgcgttcacg
 361 ctgaagtgt ggctgcgagc ggaggcggagc ccgaggtctc cggcagtgat cacagggctg
 421 tatgacaaat gttcttatat ctcacgtgac cgaggatggg tcgtgggcat tcacaccatc
 481 agtgaccaag acatcaatga accacgctac tttttctct tgaagacaga ccgagccggg
 541 caagtgacca ccatcaatgc ccaccgcagc tacctccag gccagtgggt ataccctagct
 601 gccacctatg atgggcagtt catgaagctc tatgtgaatg gtgccaggt ggccacctct
 661 gggaccaag tgggtgcat attcagccca ctgaccaga agtgcaaagt gctcatgtta
 721 gggcagtg cctgaatca caactaccgg gctacatcg agcacttcag tctgtggaag
 781 gtgccagga ctcagcggga gatactgct gacatggaaa ccatggcgc ccacactgct
 841 ctacctcagc tcctcctca ggagactgg gacaatgtga agcatgctg gtccccatg
 901 aaggatgca gcagcccaa agtggaattc agcaatgccc acggcttct gctggacacg
 961 agtctggagc ctcctctgtg cggacagaca ttgtgtgaca acacagagt cattgccagc
1023 tacaatcagc tctcaagttt cgggccagcc aaggtggtgc gctaccgcgt ggtcacctc
1081 tatgaagatg atcataagaa ccgacggtg acgcgcgagc aggtgcattt ccagcaccat
1141 cagctggctg aggcctcaa gaataccaaa atctcctggg agtggacgt gctggaggtg
1201 agcaactcct ccttcgccg ccgctccatc ccggccaact tgccccaag caagattggg
1261 gatgagaact gtgaccccga gtgcaaccac acgctgacgt gccacacgg cgggattgc
1321 cgccacctgc gccacctgc cttcgtgaag aagcagcaca acggggtgtg tgacatggac
1381 tgcaactatg aacgttcaa cttgatggt ggagagtgct gtgaccctga aatcaccaat
1441 gtcactcaga cttgcttga ccccgactct ccaacagag cctacttgga tgttaatgag
1501 ctgaagaaca ttcttaatt ggatggatcc acacatctca atatttcct tgcaaatcc
1561 tcagagagg agttgcagg agtagcaact tggcaatgg acaagagc cctgatgac
1621 ttaggtgcca tgtcttgaa cccatcttc tatggcatgc ctggcacac ccacaccatg
1681 atccatgaga ttggtcacag cctggcctc tatcacgtct tccagcgcat ctcagaaatc
1741 cagtcctgca gtgaccctg catggagata gagccttctt tgagactgg agaccctgc
1801 aatgatacca accagccc taaacacaag tcctgtggtg accagggcc aggaaatgac
1861 acctgtggct ttcatagctt cttcaacct cttacacca acttcatgag ctatgagat
1921 gagctgtga cggactctt cacgctcaat caagtgccaa gaatgcaatg ttcctgac
1981 ctggctacc agggctggca gcctccagga aaaccagaga ctgttgcct cgccccaa
2041 gttctgggc acacaacgga ctctgtgaca ctggagtggt tccacattat agatggccat
2101 ttcttgaaa gagaattggg atcagcatgt catctttgcc tggaagggag aattcctggtg
2161 cagtatgctt ccaacgttc ctcccaatg cctgcagcc catcaggaca ctggagcct
2221 cgtgaagtga aagttcatcc tgatgtgaa ctgtgcaact acaagagccc cgcactgg
2281 agccaaatt cagctgtcaa cccacacacg gttcctcag cctgcctga gctcaaggc
2341 tgctacctcg agtggagtt cctataccca ttggtccctg agtctctgac cattgggtg
2403 acctttgtct ccacggactg ggactctagt ggagctgtca atgacatcaa actgtggct
2461 gtcagtggga agaacatctc cctgggtcct cagaatgtct tctgtgatgt cccactgaca
2523 atcagactct ggacgtgg cgaggagtg tatggcatc aaatctacac gctggatgag
2581 cacctggaga tcgatgtgc catgtgcag tccatgcag acacccact ctgtctacag
2641 tgtaagccc tgaagtataa ggtggtccgg gacctctcta tccagatggga tgtggcctcc
2701 atcctacatc tcaataggaa attgtgagac atggatctaa acattggcag tgtgtaccag
2761 tattgggca taactatttc aggaactgaa gagagtgagc atcaactgc tgtccataac
2821 atccatggaa gtggtactg tgcgatggc atttaccaaa agaccaagg tgaacaatgc
2881 gacgacatga ataaatcaa tggtgatggc tgctccctt tctgtcgaca agagttctac
2941 ttcaactgta cagcggcgta tatttccatg atgggtgatg ggtatgtgga
3001 gagttttgaac aaaaaccaa cattaaggga tgtggtgctct acacgccca ggattcctg
3061 gatcagtggg catccatgc tccagtatct catcaagacc agcaatgcc aggctggtc
3121 atcatcggac agccagcagc atccagggtg tgtgaacca aggtgataga tctcagtgaa
3181 ggattccca agcatgcctg gtacctgga accatcagct accatattc caagtggct
3241 cagaccactt ttggctccgg gggtatttt tctcaaccaa tggttgcgc agctgtcatt
```

Figure 1 Con't

```
3301 gtccacctgg tgacggatgg gacatattat ggggaccaaa agcaggagac catcagcgtg
3361 cagctgcttg ataccaaaga tcagagccac gatctaggcc tccatgtcct gagctgcagg
3421 aacaatcccc tgattatccc tgtggtccat gacctcagcc agccttcta ccacagccag
3481 ggggtacgtg tgagcttcag ttcgccctg gtcgccatct cggggbggc cctccgttcc
3541 ttcgacaact ttgacccgt cacoctgagc agtgccagta gagggagac ctacagcoct
3601 gccgagcaga gctgcgtgca cttcgcatgt gagaaaactg actgtccaga gctggctgtg
3661 gagaatgctt ctctcaattg ctccagcagc gaccgctacc acggtgccca gtgtactgtg
3721 agctgccgga caggctacgt gctccagata cggcgggatg atgagctgat caagagccag
3781 acgggaccca gcgtcacaagt gacctgtaca gagggcaaagt ggaataagca ggtggcctgt
3841 gagccagtcg actgcagcat cccagatcac catcaagtct atgctgcctc cttctcctgc
3901 cctgagggca ccaccttgg cagtcaatgt tccttccagt gccgtcaccc tgcacaattg
3961 aaaggcaaca acagcctcct gacctgtatg gaggatgggc tgtggtcctt cccagaggcc
4021 ctgtgtgagc tcatgtgcct cgctcaacc cctgtgccca atgcagacct ccagacgcc
4081 cggtgccgag agaataagca caaggtgagc tccttctgca aatacaaatg caagcctgga
4141 taccatgtgc ctggatcctc tggaagtca aagaaacggg cctccaagac tcagtgtacc
4201 caggatggca gctggcagga gggagcttgt gttcctgtga cctgtgacc aactccacca
4261 aaattccatg ggctctacca gtgtactaat ggcttccagt tcaacagtga gtgtaggatc
4321 aagtgtgaag acagtgatgc ctccagggaa cttgggagca atgtcattca ttgccggaaa
4381 gatggcacct ggaacggctc cttccatgtc tgccaggaga tgcaaggcca gbgctcggtt
4441 ccaaacgagc tcaacagcaa cctcaaactg cagtgcctg atggctatgc catagggtcg
4501 gagctgcttg cctgtgcct ggaccacgca ggcagtcca tcatcctgca aatgaacgtg
4561 acgtgcgtg acatccccca ctggctgaac ccacacgag tagagagagt tgtctgcact
4621 gctggtctca agtggtatcc tcaccctgct ctgattcact gtgtcaaagg ctgtgagcc
4681 ttcatgggag acaattattg tgatgccatc aacaaccgag cctttgcaa ctatgacggt
4741 ggggattgct gcacctcac agtgaagacc aaaaggtca cccattcc tatgtcctgt
4801 gatctacaag gtgactgtgc ttgtcgggac cccaggcca aagaacacag cggaaagac
4861 ctccggggat acagccatgg ctaa
```

Figure 2

MRLWSWVLHLGLLSAALGCGLAERPRRARRDPRAGRPPRPAAGPATCATRAARGRRASPPPPPPPGGAWEAVR
VPRRRQQREARGATEEPSPPSRALYFSGRGEQLRLRADLELPRDAFTLQVWLRAEGGQRSPAVITGLYDKCSYISR
DRGWVVGIHTISDQDNKDPRYFFSLKTDRARQVTTINAHRSYLPGQWVYLAATYDGQFMKLYVNGAQVATSGEQV
GGIFSPLTQKCKVLMLGGSALNHNYRGYIEHFSLWKVARTQREILSDMETHGAHTALPQLLLQENWDNVKHAWSP
MKDGSSPKVEFSNAHGFLLDTSLEPPLCGQTLCDNTEVIASYNQLSSFRQPKVVRYRVVNLYEDDHKNPTVTREQV
DFQHHQLAEAFKQYNISWELDVLEVSNSSLRRRLILANCDISKIGDENCDPECNHTLTGHDGGDCRHLRHPAFVK
KQHNGVCDMDCNYERFNFDGGECCDPEITNVTQTCFDPDSPHRAYLDVNELKNILKLDGSTHLNIFFAKSSEEELA
GVATWPWDKEALMHLGGIVLNPSFYGMPGHTHTMIHEIGHSLGLYHVFRGISEIQSCSDPCMETEPSFETGDLCND
TNPAPKHKSCGDPGPGNDTCGFHSFFNTPYNNFMSYADDDCTDSFTPNQVARMHCYLDLVYQGWQPSRKPAPV
ALAPQVLGHTTDSVTLEWFPPIDGHFFERELGSACHLCLEGRILVQYASNASSPMPCSPSGHWSPREAEGHPDVE
QPCKSSVRTWSPNSAVNPHTVPPACPEPQGCYLELEFLYPLVPESLTIWVTFVSTDWDSSGAVNDIKLLAVSGKNIS
LGPQNVFCDVPLTIRLWDVGEEVYGIQIYTLDEHLEIDAAMLTSTADTPLCLQCKPLKYKVVRDPPLQMDVASILHLN
RKFVDMDLNLGSVYQYWVITISGTEESEPSPAVTYIHGSGYCGDGIIQKDQGEQCDDMNKINGDGCSLFCRQEVSF
NCIDEPSRCYFHDGDGVCEEFEQKTSIKDCGVYTPQGFLDQWASNASVSHQDQQCPGWVIIGQPAASQVCRTKVI
DLSEGISQHAWYPCTISYPYSQLAQTTFWLRAYFSQPMVAAAVIVHLVTDGTYYGDQKQETISVQLLDTKDQSHDLG
LHVLSCRNNPLIIPVVHDLSQPFYHSQAVRVSFSSPLVAISGVALRSFDNFDPVTLSSCQRGETYSPAEQSCVHFAC
EKTDCPELAVENASLNCSSSDRYHGAQCTVSCRTGYVLQIRRDDELIKSQTGPSVTVTCTEGKWNKQVACEPVDC
SIPDHHQVYAASFSCPEGTTFGSQCSFQCRHPAQLKGNNSLLTCMEDGLWSFPEALCELMCLAPPPVPNADLQTA
RCRENKHKVGSFCKYKCKPGYHVPGSSRKSKKRAFKTQCTQDGSWQEGACVPVTCDPPPPKFHGLYQCTNGFQ
FNSECRIKCEDSDASQGLGSNVIHCRKDGTWNGSFHVCQEMQGGQCSVPNELNSNLKLQCPDGYAIGSECATSCLD
HNSESIILPMNVTVRDIPHWLNPTRVERVVCTAGLKWYPHPALIHCVKGCEPFMGDNYCDAINNRAFCNYDGGDCC
TSTVKTKKVTPFPMSCDLQGDCACRDPQAQEHSRKDLRGYSHG

Figure 3

```
   1 atgataactg cactgacaac ttcactccta accaagtggc ccgaatgcat tgctatttgg
  61 acctagtcta tcagcagtgg actgaaagca gaaagcccac cccatcccc attccaccta
 121 tggtcatcgg acagaccaac aagtccctca ctatccactg gctgcctcct attagtggag
 181 ttgtatatga cagggcctca ggcagcttgt gtggcgcttg cactgaagat gggacctttc
 241 gtcagtatgt gcacacagct tcctcccggc gggtgtgtga ctcctcaggt tattggaccc
 301 cagaggaggc tgtggggcct cctgatgtgg atcagccctg cgagccaagc ttacaggcct
 361 ggagccctga ggtccacctg taccacatga acatgacggt ccctgcccc acagaaggct
 421 gtagcttgga gctgctcttc caacaccogg tccaagccga caccctcacc ctgtgggtca
 481 cttccttctt catggagtcc tcgcaggtcc tctttgacac agagatcttg ctggaaaaca
 541 aggagtcagt gcacctgggc cccttagaca cttctgtga catcccactc accatcaaac
 601 tgcacgtgga tgggaaggtg tcggggtga aagtctacac ctttgatgag aggatagaga
 661 ttgatgcagc actcctgact tctcagcccc acagtccctt gtgctctggc tgcaggcctg
 721 tgaggtacca ggttctccgc gatccccat ttgccagtgg tttgcccgtg gtggtgacac
 781 attctcacag gaagttcacg gacgtggagg tcacacctgg acagatgtat cagtaccaag
 841 ttctagctga agctggagga gaactgggag aagcttcgcc tcctctgaac cacattcatg
 901 gagctcctta ttgtggagat gggaaggtgt cagagagact gggagaagag tgtgatgatg
 961 gagaccttgt gagcggagat ggctgctcca aggtgtgtga gctggaggaa ggtttcaact
1021 gtgtaggaga gccaagcctt tgctacatgt atgagggaga tggcatatgt gaaccttttg
1081 agagaaaaac cagcattgta gactgtggca tctacactcc caaaggatac ttggatcaat
1141 gggctaccog ggcttactcc tctcatgaag acaagaagaa gtgtcctgtt tccttggtaa
1201 ctggagaacc tcattcccta atttgcacat cataccatcc agatttaccc aaccaccgtc
1261 ccctaactgg ctggtttccc tgtgttgcca gtgaaaatga aactcaggat gacaggagtg
1321 aacagccaga aggtagcctg aagaaagagg atgaggtttg gctcaaagtg tgtttcaata
1381 gaccaggaga ggccagagca atttttattt ttttgacaac tgatggccta gttcccggag
1441 agcatcagca gccgacagtg actctctacc tgaccgatgt ccgtggaagc aaccactctc
1501 ttgaaccta tggactgtca tgccagcata atccactgat tatcaatgtg acccatcacc
1561 agaatgtcct tttccaccat accacctcag tgctgctgaa tttctcatcc ccacgggtcg
1621 gcatctcagc tgtggctcta aggacatcct cccgcattgg tctttcggct cccagtaact
1681 gcatctcaga ggacgagggg cagaatcatc agggacagag ctgtatccat cggccctgtg
1741 ggaagcagga cagctgtccg tcattgctgc ttgatcatgc tgatgtggtg aactgtacct
1801 ctataggccc aggtctcatg aagtgtgcta tcacttgtca aaggggattt gcccttcagg
1861 ccagcagtgg gcagtacatc aggcccatgc agaaggaaat tctgctcaca tgttcttctg
1921 ggcactggga ccagaatgtg agctgccttc ccgtggactg cggtgttccc gacccgtctt
1981 tggtgaacta tgcaaacttc tcctgctcag agggaaccaa atttctgaaa cgctgctcaa
2041 tctcttgtgt cccaccagcc aagctgcaag gactgagccc atggctgaca tgtcttgaag
2101 atggtctctg gtctctccct gaagtctact gcaagttgga gtgtgatgct cccctatta
2161 ttctgaatgc caacttgctc ctgcctcact gcctccagga caaccacgac gtgggcacca
2221 tctgcaaata tgaatgcaaa ccagggtact atgtggcaga aagtgcagag ggtaaagtca
2281 ggaa
```

Figure 4

```
MMCLKILRISLAILAGWALCSANSELGWTRKKSLVEREHLNQVLLEGERCWLGAKVRRPRASPQHHLFGVYPSRAGN
YLRPYPVGEQEIHHTGRSKPDTEGNAVSLVPPDLTENPAGLRGAVEEPAAPWVGDSPIGQSELLGDDDAYLGNQRSK
ESLGEAGIQKGSAMAATTTTAIFTTLNEPKPETQRRGWAKSRQRRQVWKRRAEDGQGDSGISSHFQPWPKHSLKHRV
KKSPPEESNQNGGEGSYREAETFNSQVGLPILYFSGRRERLLLRPEVLAEIPREAFTVEAWVKPEGGQNNPAIIAGV
FDNCSHTVSDKGWALGIRSGKDKGKRDARFFFSLCTDRVKKATILISHSRYQPGTWTHVAATYDGRHMALYVDGTQV
ASSLDQSGPLNSPFMASCRSLLLGGDSSEDGHYFRGHLGTLVFWSTALPQSHFQHSSQHSSGEEEATDLVLTASFEP
VNTEWVPFRDEKYPRLEVLQGFEPEPEILSPLQPPLCGQTVCDNVELISQYNGYWPLRGEKVIRYQVVNICDDEGLN
PIVSEEQIRLQHEALNEAFSRYNISWQLSVHQVHNSTLRHRVVLVNCEPSKIGNDHCDPECEHPLTGYDGGDCRLQG
RCYSWNRRDGLCHVECNNMLNDFDDGDCCDPQVADVRKTCFDPDSPKRAYMSVKELKEALQLNSTHFLNIYFASSVR
EDLAGAATWPWDKDAVTHLGGIVLSPAYYGMPGHTDTMIHEVGHVLGLYHVFKGVSERESCNDPCKETVPSMETGDL
CADTAPTPKSELCREPEPTSDTCGFTRFPGAPFTNYMSYTDDNCTDNFTPNQVARMHCYLDLVYQQWTESRKPTPIP
IPPMVIGQTNKSLTIHWLFPISGVVYDRASGSLCGACTEDGTFRQYVHTASSRRVCDSSGYWTPEEAVGPPDVDQPC
EPSLQAWSPEVHLYHMNMTVPCPTEGCSLELLFQHPVQADTLTLWVTSFFMESSQVLFDTEILLENKESVHLGPLDT
FCDIPLTIKLHVDGKVSGVKVYTFDERIEIDAALLTSQPHSPLCSGCRPVRYQVLRDPPFASGLPVVVTHSHRKFTD
VEVTPGQMYQYQVLAEAGGELGEASPPLNHIHGAPYCGDGKVSERLGEECDDGDLVSGDGCSKVCELEEGFNCVGEP
SLCYMYEGDGICEPFERKTSIVDCGIYTPKGYLDQWATRAYSSHEDKKKCPVSLVTGEPHSLICTSYHPDLPNHRPL
TGWFPCVASENETQDDRSEQPEGSLKKEDEVWLKVCFNRFGEARAIFIFLTTDGLVPGEHQQPTVTLYLTDVRGSNH
SLGTYGLSCQHNPLIINVTHHQNVLFHHTTSVLLNFSSPRVGISAVALRTSSRIGLSAPSNCISEDEGQNHQGQSCI
HRPCGKQDSCPSLLLDHADVVNCTSIGPGLMKCAITCQRGFALQASSGQYIRPMQKEILLTCSSGHWDQNVSCLPVD
CGVPDPSLVNYANFSCSEGTKFLKRCSISCVPPAKLQGLSPWLTCLEDGLWSLPEVYCKLECDAPPIILNANLLLPH
CLQDNHDVGTICKYECKPGYYVAESAEGKVRNKLLKIQCLEGGIWEQGSCIPVVCEPPPPVFEGMYECTNGFSLDSQ
CVLNCNQEREKLPILCTKEGLWTQEFKLCENLQGECPPPPSELNSVEYKCEQGYGIGAVCSPLCVIPPSDPVMLPEN
ITADTLEHWMEPVKVQSIVCTGRRQWHPDPVLVHCIQSCEPFQADGWCDTINNRAYCHYDGGDCCSSTLSSKKVIPF
AADCDLDECTCRDPKAEENQ
```

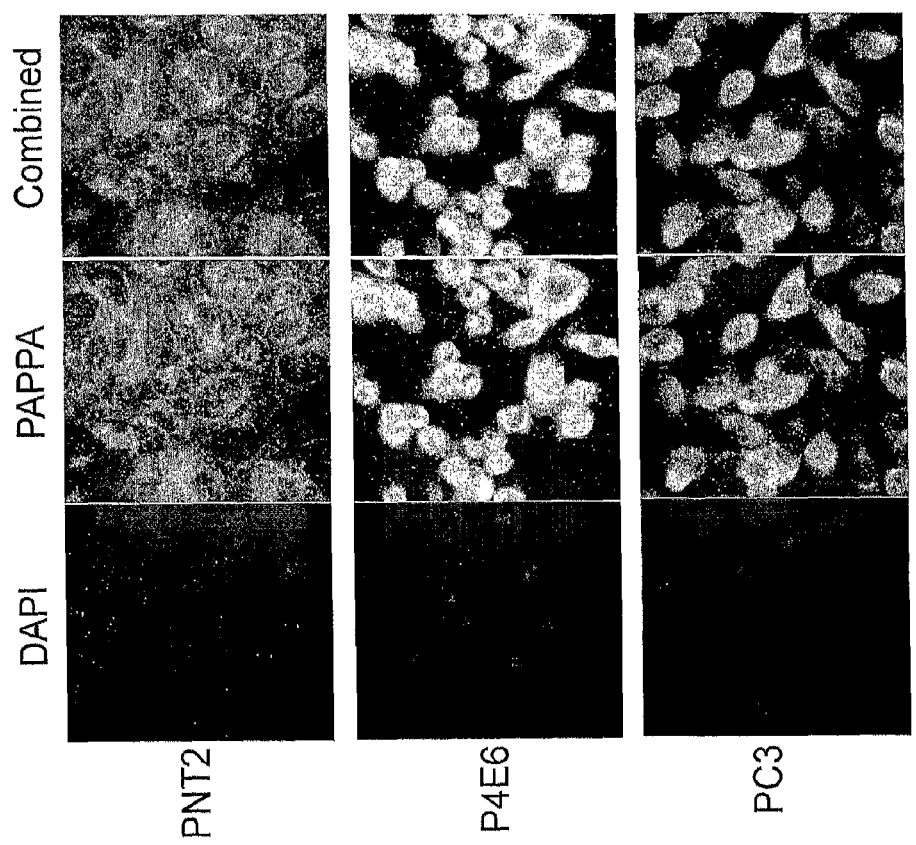

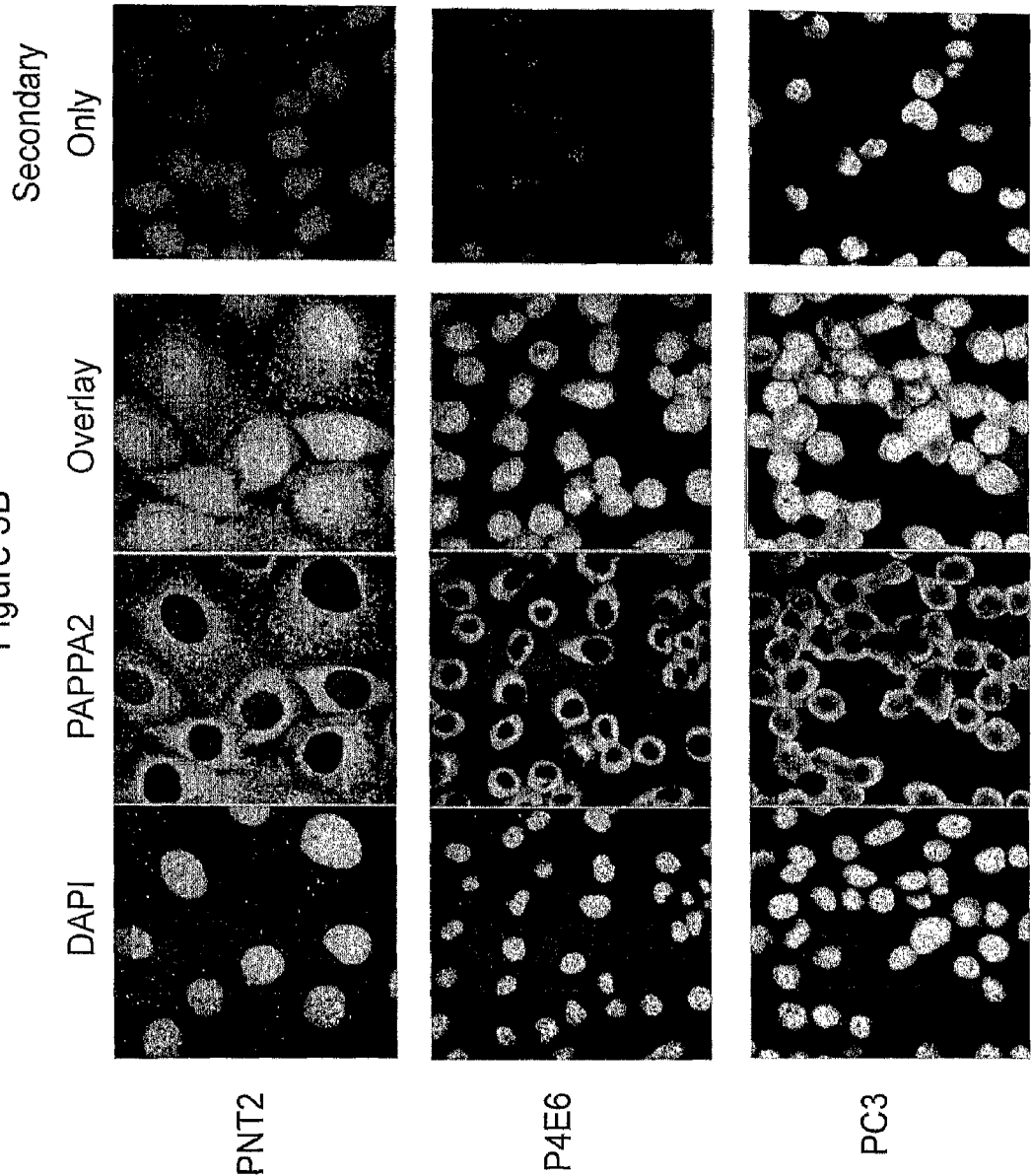

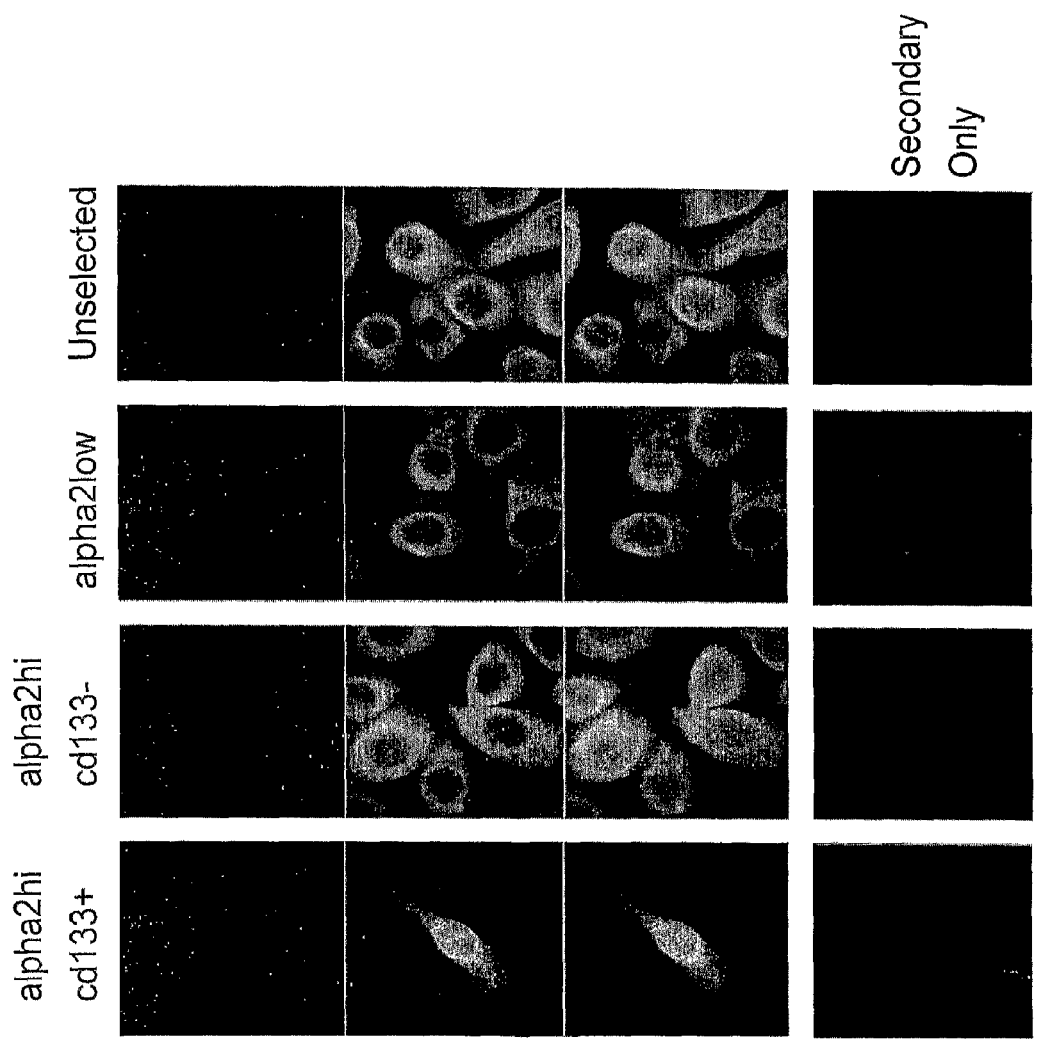

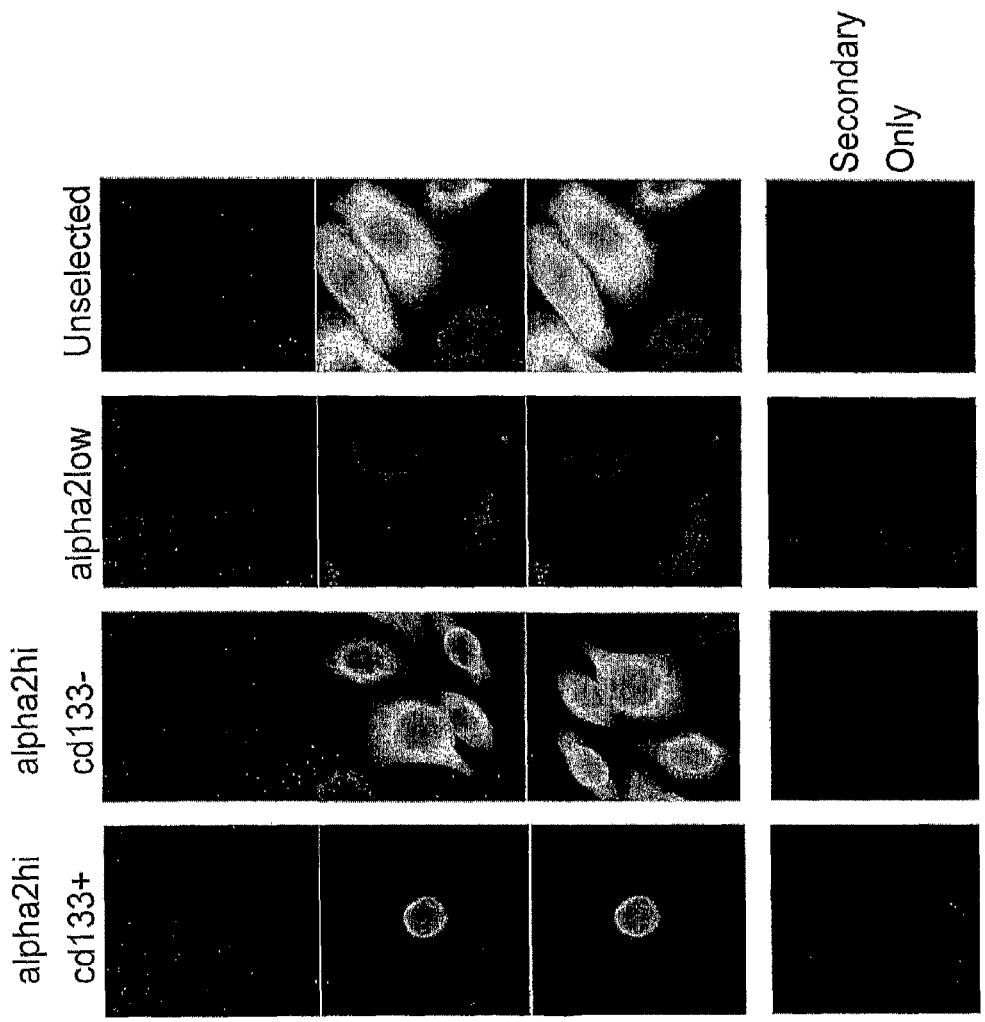

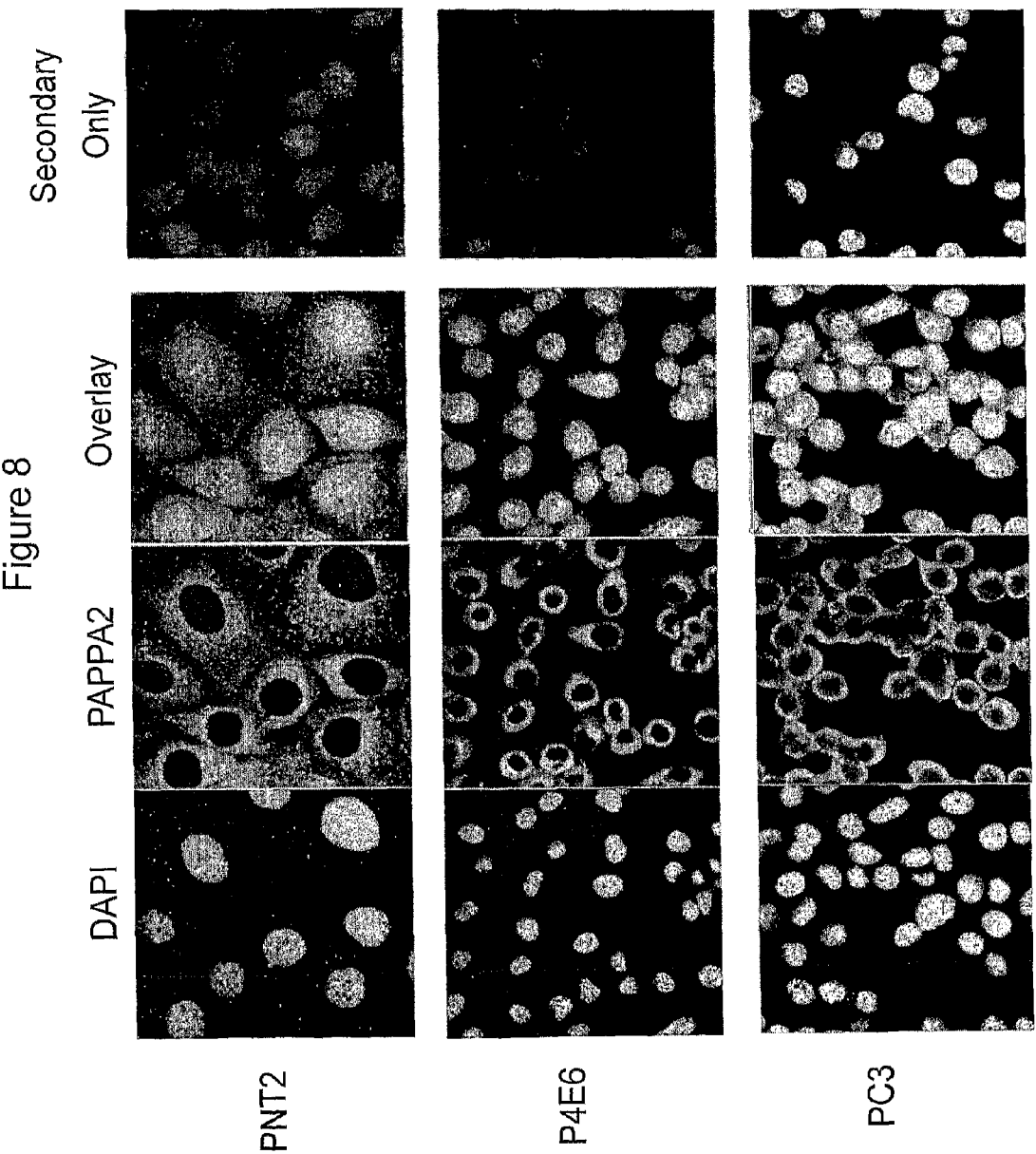

Figure 11a

GACATGCGGCTCTGGAGTTGGGTGCTGCGCCTGGGGCTGCTGAGCGCC
GCGCTGGGCTGCGGGCTGGCCGAGCGCCCCGCCGGGTCCGAAGAGA
CCCTCGGGCCGTGCGCCCCCGCGCCCCGCCGCTGGACCGGCCACCT
GCGCCACCCGGGCGGCCCGCGGTCGCCGCGCCTCGCCGCCGCCGCCT
CCGGGCGGTGCCTGGGAAGCCGTGCGCGTCCCCGGCGGCGGCAGCA
GCGGGCGGCGAGGGGCGCCGAGGAGCCGAGCCCGCCTAGCCGGGCG
CTCTATTTCAGCGGGCGAGGGGAGCAGCTGCGCCTCCGGGCCGACCTG
GAGCTACCCCGCGACGCCTTTACACTGCAAGTGTGGCTGCGAGCCGAG
GGTGGCCAGAAGTCTCCAGCAGTGATCACAGGGCTGTATGACAAATGTT
CTTATACCTCACGTGATCGAGGATGGGTCATGGGCATTCACACCACCAG
TGATCAAGGCAACAGAGATCCACGCTACTTTTTCTCCTTGAAGACAGACC
GGGCCAGGAAAGTGACCACCATTGATGCCCATCGCAGCTACCTCCCAG
GTCAGTGGGTACATCTAGCTGCTACCTATGATGGGCGGCTGATGAAGCT
CTATATGAATGGTGCCCAGGTGGCAACTTCGGCTGAGCAAGTAGGTGGC
ATATTCAGCCCACTGACCCAGAAGTGTAAAGTGCTCATGTTGGGGGGCA
GTGCTCTGAATCACAACTTCCGGGGCCACATTGAACACTTCAGTCTATG
GAAAGTAGCAAGAACCCAGCGAGAGATTGTATCCGACATGGAAACCCGT
GGCCTCCACACCCCTCTACCTCAGCTCCTCCTCCAGGAGAACTGGGACA
ACGTG

Figure 11b

GTATCCGACATGGAAACCCGTGGCCTCCACACCCCTCTACCTCAGCTCC
TCCTCCAGGAGAACTGGGACAACGTGAAGCGCACTTGGTCCCCATGAA
GGATGGCAACAGCCCCAGGTGGAATTCAGCAATGCCCACGGCTTCCT
GTTGGACACTAATTTGGAGCCCCTCTTTGTGGGCAGACACTGTGTGAC
AACACAGAAGTCATCTCCAGTTACAATCAGCTCCCAAGTTTTCGGCAGCC
CAAGGTGGTCCGCTATCGTGTGGTCAACATCTATGATGATCACCATGAG
AATCCAACGGTGAGCTGGCAACAGATTGACTTTCAGCACCAACAGCTGG
CTGAGGCCTTTCAACACTACAACATCTCCTGGGAGCTGGAGGTACTGAA
TATAAACAGTTCCTCTCTGCGTCACCGCCTCATCCTAGCCAACTGTGACA
TCAGCAAGATTGGGGATGAAAATGTGATCCAGAATGTAACCATACACTG
ACTGGTCATGATGGTGGAGATTGCCGCCAGCTGCGCTACCCTGCGTTCA
TGAAGAAGCAGCAGAATGGTGTGTGTGACATGGACTGTAACTACGAAAG
GTTTAATTTTGATGGTGGAGAGTGCTGTGACCCAGACATCACTGATGTCA
CTAAGACATGCTTTGATCCTGACTCTCCACACAGAGCCTACTTGGATGTT
AATGAGCTAAAGAACATTCTTAGACTGGACGGATCAACACATCTCAATAT
TTTCTTTGCAAACTCTTCAGAGGAGGAGTTGGCAGGAGTGGCAACTTGG
CCA

Figure 11c

CTGGACGGATCAACACATCTCAATATTTTCTTTGCAAACTCTTCAGAGGA
GGAGTTGGCAGGAGTGGCAACTTGGCCATGGGACAAGGAAGCCCTAAT
GCACTTGGGCGGTATTGTCTTGAACCCATCTTTCTATGGCATTCCCGGAC
ACACCCACACCATGATTCATGAGATTGGGCATAGCCTGGGCCTCTATCA
CATCTTCCGTGGCATCTCAGAAATCCAGTCCTGCAGTGATCCCTGCATG
GAGACAGAGCCTTCATTTGAAACTGGAGACCTCTGCAATGATACCAACC
CAGCCCCAAACACAAGTTTTGTGGAGACCCTGGACCAGGGAATGACAC
TTGTGGCTTTCATGGCTTCTTCAACACTCCTTACAACAACTTCATGAGCTA
CGCAGATGACGACTGTACAGACTCTTTCACGCCCAATCAAGTCTCCAGA
ATGCACTGTTACCTGGACCTCGTATACCAGAGCTGGCAGCCCTCCAGAA
AGCCAGCACCTGTAGCTCTTGCGCCCAGGTTGTGGGGCACACAATGG
ACTCTGTGATGCTAGAGTGGTTCCCACCCATCGATGGCCACTTCTTTGAA
AGAGAATTGGGATCAGCATGTGACCTTTGCCTAGAAGGGAGAATCCTGG
TGCAATATGCTTTCAATGCCTCCTCCCCATGCCCTGTGGACCGTCAGG
ACACTGGAGTCCTCGGGAAGCAGAAGGTCACCCAGATGTTGAACAGCC
CTGTAAATCCAGTGTCCGAACCTGGAGTCCAAATTCAGCTGTCAACCCA
CACACAGTTCCTCCAGCCTGCCCTGAGCCACAAGGCTGCTACCTCGAGC
TGGAATTTCGCTACCCTTTGGTCCCTGAGTCTCTGACCATCTGGGTAACC
TTTGTCTCCAGTGATTGGGACTCTAGTGGAGCTGTCAATGACATCAAACT
CTTGACTATCAGTGGAAAGAATATCTCTTTGGGTCCTCAGAATGTTTCT
GTGATATCCCACTTACCATCAGACTCCGGGATGTGGGTGAGGAGGTATA
TGGCATCCAAATCTATACTCTTGATGAGCACCTGGAGATTGATGCAGCAA
TG

Figure 11d

GGTGAGGAGGTATATGGCATCCAAATCTATACTCTTGATGAGCACCTGG
AGATTGATGCAGCAATGCTGACCTCCACTGTAGACAGTCCACTCTGCCT
ACAGTGTAAACCTCTGCAGTATAAAGTGCTTCGAGACCCACCTCTGCTAG
AAGATGTAGCCTCATTACTCCACCTCAACAGAAGATTCATGGACACGGAT
CTGAAACTTGGCAGTGTGTACCAGTACCGGATTATCACCATTTCAGGAAA
TGAAGAGAGCGAGCCATCACCTGCTGCCATATACACCCACGGAAGTGG
GTACTGTGGTGATGGCGTTATCCAAAAGACCAAGGAGAAGAATGTGAC
GACATGAATAAGGTCAATGGGGATGGCTGCTCCCTTTTCTGCAAGCAAG
AAGTTTCCTTCAACTGCATTGATGAACCCAGCCGGTGCTATTTCCATGAT
GGGGATGGGATGTGTGAAGAGTTTGAACAAAAAACTAGCATTAAAGACT
GTGGTGTCTACACGCCCCAGGGTTTCCTGGATCAGTGGGCATCCAATGC
TTCAGTATCTCATCAAGACCAGCAGTGCCCAGGTTGGGTTGTCATTGGG
CAGCCAGCGGCATCTCAGGTGTGTCGAACCAAGGTGATAGATCTCAGTG
AAGGCATTTCCCAGCATGCTTGGTATCCTTGCACCATTACTTACCCATAC
TACCATCTGCCTCAGACCACATTCTGGCTCCAGACATATTTCTCTCAGCC
AATGGTTGCTGCAGCTGTAATTATTCACCTGGTGACTGATGGGACATACT
ATGGGGACCAAAAGCAAGAGACCATCAGTGTGCAGTTGCTTGATACCAA
AGATCAAAGCCATGATCTAGGCCTCCATGTCTTGAGCTGCAGAAACAATC
CCCTGATTATCCCTGTGGTCCATGACCTCAGCCAGCCCTTCTACCACAG
CCAGGCGGTACATGTGAGCTTCAGTTCGCCCCTGGTCGCCATCTCGGG
GGTGGCCCTCCGCTCTTTCGACAACTTTGACCCCGTCACCCTGAGCAGC
TGCCAGAGAGGAGAGACCTACAGCCCTGCTGAGCAGAGCTGTGTGCAT

Figure 11e

TGCCAGAGAGGAGAGACCTACAGCCCTGCTGAGCAGAGCTGTGTGCAT
TTTGCCTGTCAAGCTGCCGACTGCCCAGAACTGGCCGTGGGGAATGCTT
CTCTCAACTGTTCCAGCAACCACCACTACCATGGTGCCCAGTGCACTGT
GAGCTGCCAGACAGGTTATGTGCTGCAGATACAGCGGGACGATGAGCT
AATCAAGAGCCAGGTAGGGCCAAGCATCACAGTGACATGTACCGAGGG
CAAATGGAACAAGCAGGTGGCATGTGAGCCGGTGGACTGTGGTATCCC
AGATCACCATCACGTCTATGCTGCCTCCTTCTCCTGTCCAGAGGGTACC
ACCTTTGGTAGAAGATGTTCTTTTCAGTGTCGCCACCCTGCCCAGCTGAA
AGGCAACAACAGCTTTCTGACCTGTATGGAAGATGGACTGTGGTCCTTC
CCAGAGGCCTTGTGTGAGCTCATGTGCCTCGCCCCACCCCCAGTTCCCA
ATGCGGACCTACAGACAGCCCGGTGTCGAGAGAACAAGCACAAGGTGG
GCTCCTTCTGCAAGTACAAGTGTAAACCTGGATACCACGTGCCTGGCTC
ATCTCGGAAGTCCAAGAAACGGGCTTTCAAGACTCAATGTACTCAAGATG
GCAGCTGGCAAGAGGGAACTTGTGTGCCGGTGACTTGTGACCCACCTC
CACCCAAATTCCATGGGCTCTATCAATGCACTAATGGCTTCCAGTTCAAT
AGTGAGTGCAGGATCAAGTGTGAAGACAGTGATGCCTCCCAGGGCCGT
GGGAGCAATATCATTCACTGCCGGAAAGATGGCACTTGGAGTGGTTCCT
TCCACGTCTGCCGAGAGATGCAAGGCCAGTGCTCAGCCCCAAACCAACT
CAACAGTAACCTCAAATTGCAGTGTCCTGATGGCTATGCAATAGGGTCA

Figure 11f

CGAGAGATGCAAGGCCAGTGCTCAGCCCCAAACCAACTCAACAGTAACC
TCAAATTGCAGTGTCCTGATGGCTATGCAATAGGGTCAGAGTGTGCCAT
CTCGTGCCTGGACCATAACAGCGAGTCCATCATCCTTCCCGTTAACTTGA
CAGTGCGTGACATACCCCATTGGATGAACCCACACGAGTACAGAGGAT
TGTCTGCACTGCTGGTCTCCAGTGGTATCCCCACCCTGCTCTGATCCAC
TGTGTCAAAGGCTGTGAGCCATTCATGGGAGACAACTACTGTGATGCCA
TCAACAATCGAGCCTTCTGCAACTATGATGGTGGGGACTGCTGCACCTC
CACAGTAAAGACCAAAAAGGTCACTCCCTTTCCTATGTCCTGTGACCTAC
AAAATGACTGCGCCTGTCGAGACCCTGAGGCCCAAGAACACAACCGGAA
AGATCTTCGGGGATATAGCCAT

Figure 12a 1

GACATGCGGCTCTGGAGTTGGGTGCTGCACCTGGGGCTGCTGAGCGCC
GCGCTGGGCTGCGGGCTGGCCGAGCGTCCCCGCCGGGCCCGGAGAGA
CCCGCGGGCCGGCCGACCCCCGCGCCCCGCCGCCGGCCCGGCCACCT
GCGCCACCCGGGCGGCCCGCGGCCGCCGCGCCTCGCCGCCGCCGCC
GCCGCCGCCGGGCGGTGCCTGGGAAGCCGTGCGCGTCCCCGGCGGC
GGCAGCAGCGGGAGGCGAGGGGCGCCACCGAGGAGCCGAGCCCGCC
GAGCCGGGCGCTCTATTTCAGCGGGCGAGGCGAGCAGCTGCGCCTCC
GGGCCGACCTCGAGCTGCCCCGGGACGCGTTCACGCTGCAAGTGTGGC
TGCGAGCGGAGGGGGGCCAGAGGTCTCCGGCAGTGATCACAGGGCTG
TATGACAAATGTTCTTATATCTCACGTGACCGAGGATGGGTCGTGGGCAT
TCACACCATCAGTGACCAAGACAACAAAGACCCACGCTACTTTTTCTCCT
TGAAGACAGACCGAGCCCGGCAAGTGACCACCATCAATGCCCACCGCA
GCTACCTCCCAGGCCAGTGGGTATACCTAGCTGCCACCTATGATGGGCA
GTTCATGAAGCTCTATGTGAATGGTGCCCAGGTGGCCACCTCTGGGGAA
CAAGTGGGTGGCATATTCAGCCCACTGACCCAGAAGTGCAAAGTGCTCA
TGTTAGGGGGCAGTGCCCTGAATCACAACTACCGGGGCTACATCGAGCA
CTTCAGTCTGTGGAAGGTGGCCAGGACTCAGCGGGAGATACTGTCTGAC
ATGGAAACCCATGGCGCCCACACTGCTCTACCTCAGCTCCTCCTCCAGG
AGAACTGGGACAATGTG

Figure 12b

CTGTCTGACATGGAAACCCATGGCGCCCACACTGCTCTACCTCAGCTCC
TCCTCCAGGAGAACTGGGACAATGTGAAGCATGCCTGGTCCCCCATGAA
GGATGGCAGCAGCCCCAAAGTGGAATTCAGCAATGCCCACGGCTTTCTG
CTGGACACGAGTCTGGAGCCTCCTCTGTGCGGACAGACATTGTGTGACA
ACACAGAGGTCATTGCCAGCTACAATCAGCTCTCAAGTTTCCGCCAGCC
CAAGGTGGTGCGCTACCGCGTGGTCAACCTCTATGAAGATGATCATAAG
AACCCGACGGTGACGCGCGAGCAGGTGGACTTCCAGCACCATCAGCTG
GCTGAGGCCTTCAAGCAATACAACATCTCCTGGGAGCTGGACGTGCTGG
AGGTGAGCAACTCCTCCCTTCGCCGCCGCCTCATCCTGGCCAACTGTGA
CATCAGCAAGATTGGGGATGAGAACTGTGACCCCGAGTGCAACCACACG
CTGACGGGCCACGACGGCGGGGATTGCCGCCACCTGCGCCACCCTGC
CTTCGTGAAGAAGCAGCACAACGGGGTGTGTGACATGGACTGCAACTAT
GAACGGTTCAACTTTGATGGTGGAGAGTGCTGTGACCCTGAAATCACCA
ATGTCACTCAGACTTGCTTTGACCCCGACTCTCCACACAGAGCCTACTTG
GATGTTAATGAGCTGAAGAACATTCTTAAATTGGATGGATCAACACATCT
CAATATTTTCTTTGCAAAATCCTCAGAGGAGGAGTTGGCAGGAGTAGCAA
CTTGGCCA

Figure 12c

TTGGATGGATCAACACATCTCAATATTTTCTTTGCAAAATCCTCAGAGGA
GGAGTTGGCAGGAGTAGCAACTTGGCCATGGGACAAGGAGGCCCTGAT
GCACTTAGTGTGGCATTGTCTTGAACCCATCTTTCTATGGCATGCCTGGG
CACACCCACACCATGATCCATGAGATTGGTCACAGCCTGGGCCTCTATC
ACGTCTTCCGAGGCATCTCAGAAATCCAGTCCTGCAGTGACCCCTGCAT
GGAGACAGAGCCCTCCTTCGAGACTGGAGACCTCTGCAATGATACCAAC
CCAGCCCCTAAACACAAGTCCTGTGGTGACCCAGGGCCAGGAAATGACA
CCTGTGGCTTTCATAGCTTCTTCAACACTCCTTACAACAACTTCATGAGC
TATGCAGATGACGACTGTACGGACTCCTTCACGCCCAATCAAGTCGCCA
GAATGCACTGTTACCTGGACCTGGTCTACCAGGGCTGGCAGCCCTCCAG
GAAACCAGCGCCTGTTGCCCTCGCCCCCAAGTTCTGGGCCACACAAC
GGACTCTGTGACACTGGAGTGGTTCCCACCTATAGATGGCCATTTCTTTG
AAAGAGAATTGGGATCAGCATGTCATCTTTGCCTGGAAGGGAGAATCCT
GGTGCAGTATGCTTCCAACGCTTCCTCCCCAATGCCCTGCAGCCCATCA
GGACACTGGAGCCCTCGTGAAGCAGAAGGTCATCCTGATGTTGAACAGC
CCTGTAAGTCCAGTGTCCGCACCTGGAGCCCAAATTCAGCTGTCAACCC
ACACACGGTTCCTCCAGCCTGCCCTGAGCCTCAAGGCTGCTACCTCGAG
CTGGAGTTCCTCTACCCCTTGGTCCCTGAGTCTCTGACCATTTGGGTGA
CCTTTGTCTCCACTGACTGGGACTCTAGTGGAGCTGTCAATGACATCAAA
CTGTTGGCTGTCAGTGGGAAGAACATCTCCCTGGGTCCTCAGAATGTCT
TCTGTGATGTCCCACTGACCATCAGACTCTGGGACGTGGGCGAGGAGG
TGTATGGCATCCAAATCTACACGCTGGATGAGCACCTGGAGATCGATGC
TGCCATG

Figure 12d

GGCGAGGAGGTGTATGGCATCCAAATCTACACGCTGGATGAGCACCTG
GAGATCGATGCTGCCATGTTGACCTCCACTGCAGACACCCCACTCTGTC
TACAGTGTAAGCCCCTGAAGTATAAGGTGGTCCGGGACCCTCCTCTCCA
GATGGATGTGGCCTCCATCCTACATCTCAATAGGAAATTCGTAGACATGG
ATCTAAATCTTGGCAGTGTGTACCAGTATTGGGTCATAACTATTTCAGGA
ACTGAAGAGAGTGAGCCATCACCTGCTGTCACATACATCCATGGAAGTG
GGTACTGTGGCGATGGCATTATACAAAAAGACCAAGGTGAACAATGCGA
CGACATGAATAAGATCAATGGTGATGGCTGCTCCCTTTTCTGCCGACAA
GAAGTCTCCTTCAATTGTATTGATGAACCCAGCCGGTGCTATTTCCATGA
TGGTGATGGGGTATGTGAGGAGTTTGAACAAAAACCAGCATTAAGGAC
TGTGGTGTCTACACGCCCCAGGGATTCCTGGATCAGTGGGCATCCAATG
CTTCAGTATCTCATCAAGACCAGCAATGCCCAGGCTGGGTCATCATCGG
ACAGCCAGCAGCATCCCAGGTGTGTCGAACCAAGGTGATAGATCTCAGT
GAAGGCATTTCCCAGCATGCCTGGTACCCTTGCACCATCAGCTACCCAT
ATTCCCAGCTGGCTCAGACCACTTTTTGGCTCGGGCGTATTTTCTCAA
CCAATGGTTGCCGCAGCTGTCATTGTCCACCTGGTGACGGATGGGACAT
ATTATGGGGACCAAAAGCAGGAGACCATCAGCGTGCAGCTGCTTGATAC
CAAAGATCAGAGCCACGATCTAGGCCTCCATGTCCTGAGCTGCAGGAAC
AATCCCCTGATTATCCCTGTGGTCCATGACCTCAGCCAGCCCTTCTACCA
CAGCCAGGCGGTACGTGTGAGCTTCAGTTCGCCCCTGGTCGCCATCTC
GGGGGTGGCCCTCCGTTCCTTCGACAACTTTGACCCCGTCACCCTGAGC

Figure 12d Con't

AGCTGCCAGAGAGGGGAGACCTACAGCCCTGCCGAGCAGAGCTGCGTGCAC

Figure 12e

TGCCAGAGAGGGGAGACCTACAGCCCTGCCGAGCAGAGCTGCGTGCAC
TTCGCATGTGAGAAAACTGACTGTCCAGAGCTGGCTGTGGAGAATGCTT
CTCTCAATTGCTCCAGCAGCGACCGCTACCACGGTGCCCAGTGTACTGT
GAGCTGCCGGACAGGCTACGTGCTCCAGATACGGCGGGATGATGAGCT
GATCAAGAGCCAGACGGGACCCAGCGTCACAGTGACCTGTACAGAGGG
CAAGTGGAATAAGCAGGTGGCCTGTGAGCCAGTCGACTGCAGCATCCC
AGATCACCATCAAGTCTATGCTGCCTCCTTCTCCTGCCCTGAGGGCACC
ACCTTTGGCAGTCAATGTTCCTTCCAGTGCCGTCAGCCTGCACAATTGAA
AGGCAACAACAGCCTCCTGACCTGCATGGAGGATGGGCTGTGGTCCTTC
CCAGAGGCCCTGTGTGAGCTCATGTGCCTCGCTCCACCCCCTGTGCCC
AATGCAGACCTCCAGACCGCCCGGTGCCGAGAGAATAAGCACAAGGTG
GGCTCCTTCTGCAAATACAAATGCAAGCCTGGATACCATGTGCCTGGAT
CCTCTCGGAAGTCAAAGAAACGGGCCTTCAAGACTCAGTGTACCCAGGA
TGGCAGCTGGCAGGAGGGAGCTTGTGTTCCTGTGACCTGTGACCCACC
TCCACCAAAATTCCATGGGCTCTACCAGTGTACTAATGGCTTCCAGTTCA
ACAGTGAGTGTAGGATCAAGTGTGAAGACAGTGATGCCTCCCAGGGACT
TGGGAGCAATGTCATTCATTGCCGGAAAGATGGCACCTGGAACGGCTCC
TTCCATGTCTGCCAGGAGATGCAAGGCCAGTGCTCGGTTCCAAACGAGC
TCAACAGCAACCTCAAACTGCAGTGCCCTGATGGCTATGCCATAGGGTC
G

Figure 12f

CAGGAGATGCAAGGCCAGTGCTCGGTTCCAAACGAGCTCAACAGCAAC
CTCAAACTGCAGTGCCCTGATGGCTATGCCATAGGGTCGGAGTGTGCCA
CCTCGTGCCTGGACCACAACAGCGAGTCCATCATCCTGCCAATGAACGT
GACCGTGCGTGACATCCCCACTGGCTGAACCCCACACGGGTAGAGAG
AGTTGTCTGCACTGCTGGTCTCAAGTGGTATCCTCACCCTGCTCTGATTC
ACTGTGTCAAAGGCTGTGAGCCCTTCATGGGAGACAATTATTGTGATCC
CATCAACAACCGAGCCTTTTGCAACTATGACGGTGGGGATTGCTGCACC
TCCACAGTGAAGACCAAAAAGGTCACCCCATTCCCTATGTCCTGTGATCT
ACAAGGTGACTGTGCTTGTCGGGACCCCCAGGCCCAAGAACACAGCCG
GAAAGACCTCCGGGGATACAGCCAT

Figure 13a

DMRLWSWVLRLGLLSAALGCGLAERPRRVRRDPRAVRPPRPAAGPATCAT
RAARGRRASPPPPPGGAWEAVRVPRRRQQRAARGAEEPSPPSRALYFSG
RGEQLRLRADLELPRDAFTLQVWLRAEGGQKSPAVITGLYDKCSYTSRDRG
WVMGIHTTSDQGNRDPRYFFSLKTDRARKVTTIDAHRSYLPGQWVHLAATY
DGRLMKLYMNGAQVATSAEQVGGIFSPLTQKCKVLMLGGSALNHNFRGHIE
HFSLWKVARTQREIVSDMETRGLHTPLPQLLLQENWDNV

Figure 13b

VSDMETRGLHTPLPQLLLQENWDNVKRTWSPMKDGNSPQVEFSNAHGFLL
DTNLEPPLCGQTLCDNTEVISSYNQLPSFRQPKVVRYRVVNIYDDHHENPTV
SWQQIDFQHQQLAEAFQHYNISWELEVLNINSSSLRHRLILANCDISKIGDEK
CDPECNHTLTGHDGGDCRQLRYPAFMKKQQNGVCDMDCNYERFNFDGG
ECCDPDITDVTKTCFDPDSPHRAYLDVNELKNILRLDGSTHLNIFFANSSEEE
LAGVATWP

Figure 13c

LDGSTHLNIFFANSSEEELAGVATWPWDKEALMHLGGIVLNPSFYGIPGHTH
TMIHEIGHSLGLYHIFRGISEIQSCSDPCMETEPSFETGDLCNDTNPAPKHKF
CGDPGPGNDTCGFHGFFNTPYNNFMSYADDDCTDSFTPNQVSRMHCYLD
LVYQSWQPSRKPAPVALAPQVVGHTMDSVMLEWFPPIDGHFFERELGSAC
DLCLEGRILVQYAFNASSPMPCGPSGHWSPREAEGHPDVEQPCKSSVRTW
SPNSAVNPHTVPPACPEPQGCYLELEFRYPLVPESLTIWVTFVSSDWDSSG
AVNDIKLLTISGKNISLGPQNVFCDIPLTIRLRDVGEEVYGIQIYTLDEHLEIDAA
M

Figure 13d

GEEVYGIQIYTLDEHLEIDAAMLTSTVDSPLCLQCKPLQYKVLRDPPLLEDVA
SLLHLNRRFMDTDLKLGSVYQYRIITISGNEESEPSPAAIYTHGSGYCGDGVI
QKDQGEECDDMNKVNGDCSLFCKQEVSFNCIDEPSRCYFHDGDGMCEE
FEQKTSIKDCGVYTPQGFLDQWASNASVSHQDQQCPGWVVIGQPAASQVC
RTKVIDLSEGISQHAWYPCTITYPYYHLPQTTFWLQTYFSQPMVAAAVIIHLV
TDGTYYGDQKQETISVQLLDTKDQSHDLGLHVLSCRNNPLIIPVVHDLSQPF
YHSQAVHVSFSSPLVAISGVALRSFDNFDPVTLSSCQRGETYSPAEQSCVH

Figure 13e

CQRGETYSPAEQSCVHFACQAADCPELAVGNASLNCSSNHHYHGAQCTVS
CQTGYVLQIQRDDELIKSQVGPSITVTCTEGKWNKQVACEPVDCGIPDHHH
VYAASFSCPEGTTFGRRCSFQCRHPAQLKGNNSFLTCMEDGLWSFPEALC
ELMCLAPPPVPNADLQTARCRENKHKVGSFCKYCKPGYHVPGSSRKSKK
RAFKTQCTQDGSWQEGTCVPVTCDPPPPKFHGLYQCTNGFQFNSECRIKC
EDSDASQGRGSNIIHCRKDGTWSGSFHVCREMQGQCSAPNQLNSNLKLQC
PDGYAIGS

Figure 13f

REMQGQCSAPNQLNSNLKLQCPDGYAIGSECAISCLDHNSESIILPVNLTVR
DIPHWMNPTRVQRIVCTAGLQWYPHPALIHCVKGCEPFMGDNYCDAINNRA
FCNYDGGDCCTSTVKTKKVTPFPMSCDLQNDCACRDPEAQEHNRKDLRGY
SH

Figure 14a

DMRLWSWVLHLGLLSAALGCGLAERPRRARRDPRAGRPPRPAAGPATCAT
RAARGRRASPPPPPPPGGAWEAVRVPRRRQQREARGATEEPSPPSRALY
FSGRGEQLRLRADLELPRDAFTLQVWLRAEGGQRSPAVITGLYDKCSYISR
DRGWVVGIHTISDQDNKDPRYFFSLKTDRARQVTTINAHRSYLPGQWVYLA
ATYDGQFMKLYVNGAQVATSGEQVGGIFSPLTQKCKVLMLGGSALNHNYR
GYIEHFSLWKVARTQREILSDMETHGAHTALPQLLLQENWDNV

Figure 14b

LSDMETHGAHTALPQLLLQENWDNVKHAWSPMKDGSSPKVEFSNAHGFLL
DTSLEPPLCGQTLCDNTEVIASYNQLSSFRQPKVVRYRVVNLYEDDHKNPT
VTREQVDFQHHQLAEAFKQYNISWELDVLEVSNSSLRRRLILANCDISKIGDE
NCDPECNHTLTGHDGGDCRHLRHPAFVKKQHNGVCDMDCNYERFNFDGG
ECCDPEITNVTQTCFDPDSPHRAYLDVNELKNILKLDGSTHLNIFFAKSSEEE
LAGVATWP

Figure 14c

LDGSTHLNIFFAKSSEEELAGVATWPWDKEALMHLGGIVLNPSFYGMPGHT
HTMIHEIGHSLGLYHVFRGISEIQSCSDPCMETEPSFETGDLCNDTNPAPKH
KSCGDPGPGNDTCGFHSFFNTPYNNFMSYADDDCTDSFTPNQVARMHCY
LDLVYQGWQPSRKPAPVALAPQVLGHTTDSVTLEWFPPIDGHFFERELGSA
CHLCLEGRILVQYASNASSPMPCSPSGHWSPREAEGHPDVEQPCKSSVRT
WSPNSAVNPHTVPPACPEPQGCYLELEFLYPLVPESLTIWVTFVSTDWDSS
GAVNDIKLLAVSGKNISLGPQNVFCDVPLTIRLWDVGEEVYGIQIYTLDEHLEI
DAAM

Figure 14d

GEEVYGIQIYTLDEHLEIDAAMLTSTADTPLCLQCKPLKYKVVRDPPLQMDVA
SILHLNRKFVDMDLNLGSVYQYWVITISGTEESEPSPAVTYIHGSGYCGDGII
QKDQGEQCDDMNKINGDGCSLFCRQEVSFNCIDEPSRCYFHDGDGVCEEF
EQKTSIKDCGVYTPQGFLDQWASNASVSHQDQQCPGWVIIGQPAASQVCR
TKVIDLSEGISQHAWYPCTISYPYSQLAQTTFWLRAYFSQPMVAAAVIVHLVT
DGTYYGDQKQETISVQLLDTKDQSHDLGLHVLSCRNNPLIIPVVHDLSQPFY
HSQAVRVSFSSPLVAISGVALRSFDNFDPVTLSSCQRGETYSPAEQSCVH

Figure 14e

CQRGETYSPAEQSCVHFACEKTDCPELAVENASLNCSSSDRYHGAQCTVS
CRTGYVLQIRRDDELIKSQTGPSVTVCTEGKWNKQVACEPVDCSIPDHHQ
VYAASFSCPEGTTFGSQCSFQCRHPAQLKGNNSLLTCMEDGLWSFPEALC
ELMCLAPPPVPNADLQTARCRENKHKVGSFCKYKCKPGYHVPGSSRKSKK
RAFKTQCTQDGSWQEGACVPVTCDPPPPKFHGLYQCTNGFQFNSECRIKC
EDSDASQGLGSNVIHCRKDGTWNGSFHVCQEMQGQCSVPNELNSNLKLQ
CPDGYAIGS

Figure 14f

QEMQGQCSVPNELNSNLKLQCPDGYAIGSECATSCLDHNSESIILPMNVTV
RDIPHWLNPTRVERVVCTAGLKWYPHPALIHCVKGCEPFMGDNYCDAINNR
AFCNYDGGDCCTSTVKTKKVTPFPMSCDLQGDCACRDPQAQEHSRKDLR
GYSH

CANCER VACCINE

The invention relates to a vaccine comprising a pappalysin and vaccine compositions comprising a pappalysin.

Pappalysin is a secreted pregnancy associated metalloproteinase of molecular weight 181 kilodaltons which naturally exists as a disulphide linked homodimer which is expressed continually during pregnancy and is found in a complex with an inhibitor protein called eosinophil major basic protein in a 2:2 proteinase:inhibitor complex. A second form of the enzyme exists as pappalysin 2 [PappA2] which has a molecular weight of 198.5 kilodaltons, functions as a monomer and is preferentially expressed in the placenta and non pregnant mammary gland with low expression in the kidney, fetal brain and pancreas. The substrates for pappalysin are insulin like growth factor binding proteins [IGFBP] of which there are 6 different proteins. IGFBP 4 and 5 are the preferred substrates for pappalysin. PappA2 cleaves IGFBP 5 preferentially. IGFBPs are found tightly bound with insulin-like growth factor [IGF-1] which inhibits insulin-like growth factor I (IGF-1) activity. IGF-1 is a 70 amino acid polypeptide with a molecular weight of 7.61 kD. IGF-1 stimulates, amongst other cells, the proliferation of chondrocytes resulting in bone growth. IGF-1 is also implicated in muscle development. IGF-1 is an example of a protein ligand that interacts with members of the receptor tyrosine kinase (RTK) superfamily. Approximately 98% of IGF-1 is bound to one of the six IGFBPs. IGFBP3 is the most abundant and accounts for 80% of IGF-1 binding. IGF-1 binds two receptors; the IGF-1 receptor (IGFR) and insulin receptor (IR) the former of which is bound with greater affinity. It is also known that IGF-1 has a role in the maintenance of tumours and therefore IGF-1 antagonists will have therapeutic value in the treatment of cancer.

In our co-pending application (WO2005/089043) we describe the isolation of prostate stem cells which have been directly isolated from lymph node and prostate glands from a series of patient samples. These stem cells express markers that characterise the cells with stem cell properties. The following markers are typically expressed as prostate stem cell markers; human epithelial antigen (HEA), CD44, high expression of $\alpha_2\beta_1$ integrin and CD133. Furthermore, in our co-pending application (WO2007/0128110) we disclose array expression of genes that are up regulated in cancer prostate stem cells when compared to normal prostate stem cells. One of the most highly up regulated genes in the array is pappalysin.

We have further analysed pappalysin expression in prostate stem cells and confirm that it is highly expressed thereby validating the array analysis disclosed in WO2007/0128110. Moreover we have analysed the expression of pappalysin in other cells and found that expression is high in prostate cancer cell lines and correlates with the degree of malignancy of the prostate cell-lines. Furthermore we disclose that the related pappalysin, pappalysin 2 is also produced by cancer cell-lines to high levels. Pappalysin and pappalysin 2 are secreted proteins with a restricted tissue/cell expression pattern providing an ideal candidate for the development of small molecule inhibitors and the like.

According to an aspect of the invention there is provided a vaccine composition comprising a pappalysin polypeptide, or antigenic part thereof, with an adjuvant and/or carrier.

In a preferred embodiment of the invention the pappalysin polypeptide is represented by the amino acid sequences in FIG. 2 (SEQ ID NO: 2) or FIG. 4 (SEQ ID NO: 4).

In a preferred embodiment of the invention said antigenic part consists of an amino acid sequence or sequence variant thereof selected from the group consisting of the amino acid sequences presented in FIG. 13a (SEQ ID NO: 17), 13b (SEQ ID NO: 18), 13c (SEQ ID NO: 19), 13d (SEQ ID NO: 20), 13e (SEQ ID NO: 21) or 13f (SEQ ID NO: 22), wherein said sequence variant is an amino acid addition, deletion or substitution of at least one amino acid residue and said sequence variant includes at least one antigenic epitope.

In a preferred embodiment of the invention said antigenic part consists of an amino acid sequence presented in FIG. 13c (SEQ ID NO: 19).

In a preferred embodiment of the invention said antigenic part consists of an amino acid sequence or sequence variant thereof selected from the group consisting of the amino acid sequences presented in FIG. 14a (SEQ ID NO: 23), 14b (SEQ ID NO: 24), 14c (SEQ ID NO: 25), 14d (SEQ ID NO: 26), 14e (SEQ ID NO: 27) or 14f (SEQ ID NO: 28), wherein said sequence variant is an amino acid addition, deletion or substitution of at least one amino acid residue and said sequence variant includes at least one antigenic epitope.

In a preferred embodiment of the invention said antigenic part consists of an amino acid sequence presented in FIG. 14c (SEQ ID NO: 25).

A variant polypeptide may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies. In addition, the invention features polypeptide sequences having at least 50-75% identity with the polypeptide sequences as herein disclosed, or fragments and functionally equivalent polypeptides thereof. In one embodiment, the polypeptides have at least 75% identity, 85% identity, more preferably at least 90% identity, even more preferably at least 95% identity, still more preferably at least 97% identity, and most preferably at least 99% identity with the amino acid sequences illustrated herein.

The terms adjuvant and carrier are construed in the following manner. Some polypeptide or peptide antigens contain B-cell epitopes but no T cell epitopes. Immune responses can be greatly enhanced by the inclusion of a T cell epitope in the polypeptide/peptide or by the conjugation of the polypeptide/peptide to an immunogenic carrier protein such as keyhole limpet haemocyanin or tetanus toxoid which contain multiple T cell epitopes. The conjugate is taken up by antigen presenting cells, processed and presented by human leukocyte antigens (HLA's) class H molecules. This allows T cell help to be given by T cell's specific for carrier derived epitopes to the B cell which is specific for the original antigenic polypeptide/peptide. This can lead to increase in antibody production, secretion and isotype switching. An adjuvant is a substance or procedure which augments specific immune responses to antigens by modulating the activity of immune cells. Examples of adjuvants include, Freunds adjuvant, muramyl dipeptides, liposomes, cytokines selected from the group consisting of GMCSF, interferon gamma, interferon alpha, interferon beta, interleukin 12, interleukin 23, interleukin 17, interleukin 2, interleukin 1, transforming growth factor (TGF), tumor necrosis factor alpha (TNFα), and tumor necrosis factor beta (TNFβ); and toll-like receptor (TLR) agonists such as CpG oligonucleotides, flagellin, monophosphoryl lipid A, poly I:C and derivatives thereof.

A carrier is an immunogenic molecule which, when bound to a second molecule augments immune responses to the latter.

According to a further aspect of the invention there is provided a DNA vaccine composition comprising a nucleic acid molecule encoding a pappalysin polypeptide or antigenic part thereof.

In a preferred embodiment of the invention said composition comprises a nucleic acid molecule selected from the group consisting of:
  i) a nucleic acid molecule comprising or consisting of the nucleic acid sequence as represented in FIG. 1 (SEQ ID NO: 1) and/or FIG. 3 (SEQ ID NO: 3);
  ii) a nucleic acid molecule the complementary strand of which hybridizes under stringent hybridization conditions to the sequences in i) above wherein said nucleic acid molecule encodes a pappalysin polypeptide or antigenic part thereof.

In a preferred embodiment of the invention said nucleic acid molecule is selected from the group consisting of:
  i) a nucleic acid molecule consisting of the nucleic acid sequence as represented in FIG. 11a (SEQ ID NO: 5), 11b (SEQ ID NO: 6), 11c (SEQ ID NO:7), 11d (SEQ ID NO: 8), 11e (SEQ ID NO: 9) or 11f (SEQ ID NO: 10);
  ii) a nucleic acid molecule the complementary strand of which hybridizes under stringent hybridization conditions to the sequences in 1) above wherein said nucleic acid molecule encodes a pappalysin polypeptide or antigenic part thereof.

In a preferred embodiment of the invention said nucleic acid molecule consists of the nucleic acid sequence presented in FIG. 11c (SEQ ID NO: 7).

In a preferred embodiment of the invention said nucleic acid molecule is selected from the group consisting of:
  i) a nucleic acid molecule consisting of the nucleic acid sequence as represented in FIG. 12a (SEQ ID NO: 11), 12b (SEQ ID NO: 12), 12c (SEQ ID NO: 13), 12d (SEQ ID NO: 14), 12e (SEQ ID NO: 15) or 12f (SEQ ID NO: 16);
  ii) a nucleic acid molecule the complementary strand of which hybridizes under stringent hybridization conditions to the sequence in i) above wherein said nucleic acid molecule encodes a pappalysin polypeptide or antigenic part thereof.

In a preferred embodiment of the invention said nucleic acid molecule consists of the nucleic acid sequence presented in FIG. 12c (SEQ ID NO: 13).

In a preferred embodiment of the invention said nucleic acid molecule is part of an expression vector adapted to express said pappalysin polypeptide or antigenic part thereof.

Typically said adaptation includes, the provision of transcription control sequences (promoter sequences) which mediate cell/tissue specific expression. These promoter sequences may be cell/tissue specific, inducible or constitutive.

Promoter is an art recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences and is therefore position independent). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors (see Eukaryotic Transcription Factors, by David S Latchman, Academic Press Ltd, San Diego) is responsive to a number of environmental cues which include, by example and not by way of limitation, intermediary metabolites (eg glucose, lipids), environmental effectors (eg light, heat,).

Promoter elements also include so called TATA box and RNA polymerase initiation selection (RIS) sequences which function to select a site of transcription initiation. These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell or prokaryotic host. Vectors which are maintained autonomously are referred to as episomal vectors.

Adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

Expression control sequences also include so-called Locus Control Regions (LCRs). These are regulatory elements which confer position-independent, copy number-dependent expression to linked genes when assayed as transgenic constructs in mice. LCRs include regulatory elements that insulate transgenes from the silencing effects of adjacent heterochromatin, Grosveld et al., Cell (1987), 51: 975-985.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

In a preferred embodiment of the invention said adjuvant is selected from the group consisting of: cytokines selected from the group consisting of GMCSF, interferon gamma, interferon alpha, interferon beta, interleukin 12, interleukin 23, interleukin 17, interleukin 2, interleukin 1, TGF, TNFα, and TNFβ.

In a further alternative embodiment of the invention said adjuvant is a TLR agonist such as CpG oligonucleotides, flagellin, monophosphoryl lipid A, poly I:C and derivatives thereof.

In a preferred embodiment of the invention said adjuvant is a CpG oligonucleotide.

In a preferred embodiment of the invention said adjuvant is a bacterial cell wall derivative such as muramyl dipeptide (MDP) and/or trehelose dycorynemycolate (TDM).

According to a further aspect of the invention there is provided a method to vaccinate a subject suffering from or having a predisposition to cancer comprising administering an effective amount of a vaccine composition comprising a pappalysin polypeptide or antigenic part thereof and an adjuvant and/or carrier.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "cancer"

includes malignancies of the various organ systems, such as those affecting, for example, lung, breast, thyroid, lymphoid, gastrointestinal, and genito-urinary tract, as well as adenocarcinomas which include malignancies such as most colon cancers, renal-cell carcinoma, prostate cancer and/or testicular tumours, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumours composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In a preferred method of the invention said cancer is prostate cancer.

In an alternative preferred method of the invention said cancer is lung cancer.

According to a further aspect of the invention there is provided a nucleic acid molecule consisting of a nucleic acid sequence selected from the group consisting of (i) a nucleic acid molecule consisting of the nucleic acid sequence as represented in FIG. 11a (SEQ ID NO: 5), 11b (SEQ ID NO: 6), 11c (SEQ ID NO: 7), 11d (SEQ ID NO: 8), 11e (SEQ ID NO:9) or 11f (SEQ ID NO: 10);

(ii) a nucleic acid molecule the complementary strand of which hybridizes under stringent hybridization conditions to the sequences in i) above wherein said nucleic acid molecule encodes a pappalysin polypeptide or antigenic part thereof; and (iii) a nucleic acid molecule comprising nucleotide sequences that are degenerate as a result of the genetic code to the nucleotide sequence defined in (i) and (ii).

According to a further aspect of the invention there is provided a nucleic acid molecule consisting of a nucleic acid sequence selected from the group consisting of:

(i) a nucleic acid molecule consisting of the nucleic acid sequence as represented in FIG. 12a (SEQ ID NO: 11), 12b (SEQ ID NO: 12), 12c (SEQ ID NO: 13), 12d (SEQ ID NO: 14), 12e (SEQ ID NO: 15) or 12f (SEQ ID NO: 16);

(ii) a nucleic acid molecule the complementary strand of which hybridizes under stringent hybridization conditions to the sequences in 1) above wherein said nucleic acid molecule encodes a pappalysin polypeptide or antigenic part thereof; and (iii) a nucleic acid molecule comprising nucleotide sequences that are degenerate as a result of the genetic code to the nucleotide sequence defined in (i) and (ii).

According to a further aspect of the invention there is provided a polypeptide encoded by a nucleic acid molecule according to the invention.

In a preferred embodiment of the invention said polypeptide is a variant polypeptide and comprises the amino acid sequence represented in FIG. 13a (SEQ ID NO: 17), 13b (SEQ ID NO: 18), 13c (SEQ ID NO: 19), 13d (SEQ ID NO: 20), 13e (SEQ ID NO: 21) or 13f (SEQ ID NO: 22), which sequence has been modified by deletion, addition or substitution of at least one amino acid residue.

In a preferred embodiment of the invention said polypeptide consists of the amino acid sequence as represented in FIG. 13a (SEQ ID NO: 17), 13b (SEQ ID NO: 18), 13c (SEQ ID NO: 19), 13d (SEQ ID NO: 20), 13e (SEQ ID NO: 21) or 13f (SEQ ID NO: 22).

In a preferred embodiment of the invention said polypeptide consists of the amino acid sequence as represented in FIG. 13c (SEQ ID NO: 19).

In a preferred embodiment of the invention said polypeptide is a variant polypeptide and comprises the amino acid sequence represented in FIG. 14a (SEQ ID NO: 23), 14b (SEQ ID NO: 24), 14c (SEQ ID NO: 25), 14d (SEQ ID NO: 26), 14e (SEQ ID NO: 27) or 14f (SEQ ID NO: 28), which sequence has been modified by deletion, addition or substitution of at least one amino acid residue.

In a preferred embodiment of the invention said polypeptide consists of the amino acid sequence as represented in FIG. (SEQ ID NO: 23), 14b (SEQ ID NO: 24), 14c (SEQ ID NO: 25), 14d (SEQ ID NO: 26), 14e (SEQ ID NO: 27) or 14f (SEQ ID NO: 28).

In a preferred embodiment of the invention said polypeptide consists of the amino acid sequence as represented in FIG. 14c (SEQ ID NO: 25).

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures:

FIG. 1 is the nucleic acid sequence of human pappalysin (SEQ ID NO: 1);

FIG. 2 is the amino acid sequence of human pappalysin (SEQ ID NO: 2);

FIG. 3 is the nucleic acid sequence of human pappalysin 2 (SEQ ID NO: 3);

FIG. 4 is the amino acid sequence of human pappalysin 2 SEQ ID NO: 4);

FIG. 5 illustrates immunofluoresence of pappalysin in prostate cell-lines PNT 2, P4E6 and PC3;

FIG. 6 illustrates immunofluoresence of pappalysin in primary BPH cells; and

FIG. 7 illustrates immunofluoresence of pappalysin in primary cancer cells;

FIG. 8 illustrates immunofluoresence of pappalysin 2 in cell-lines PNT 2, P4E6 and PC3;

Figure 9:
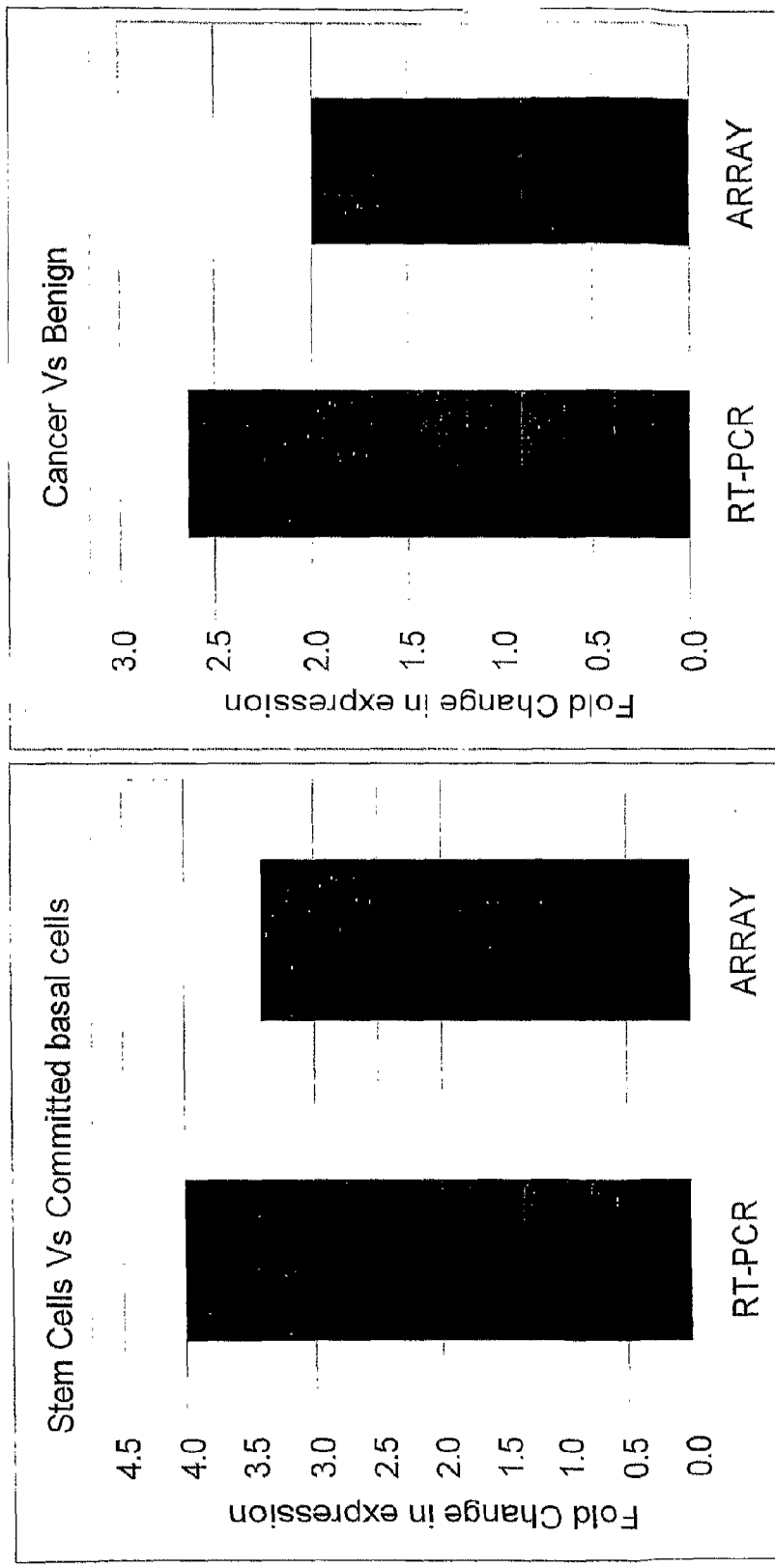
FIG. 9 is a comparison of pappalysin expression using RT PCR with levels of expression predicted from array analysis.
Figure 15:
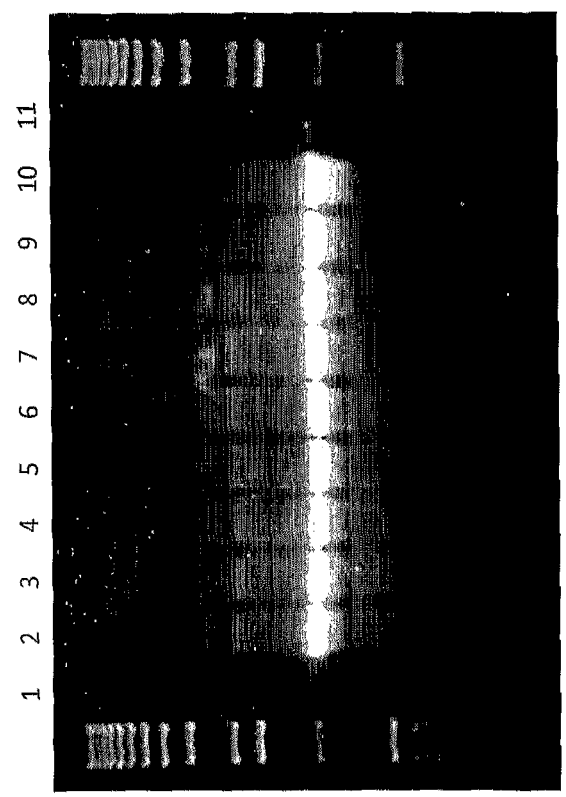
Figure 16:
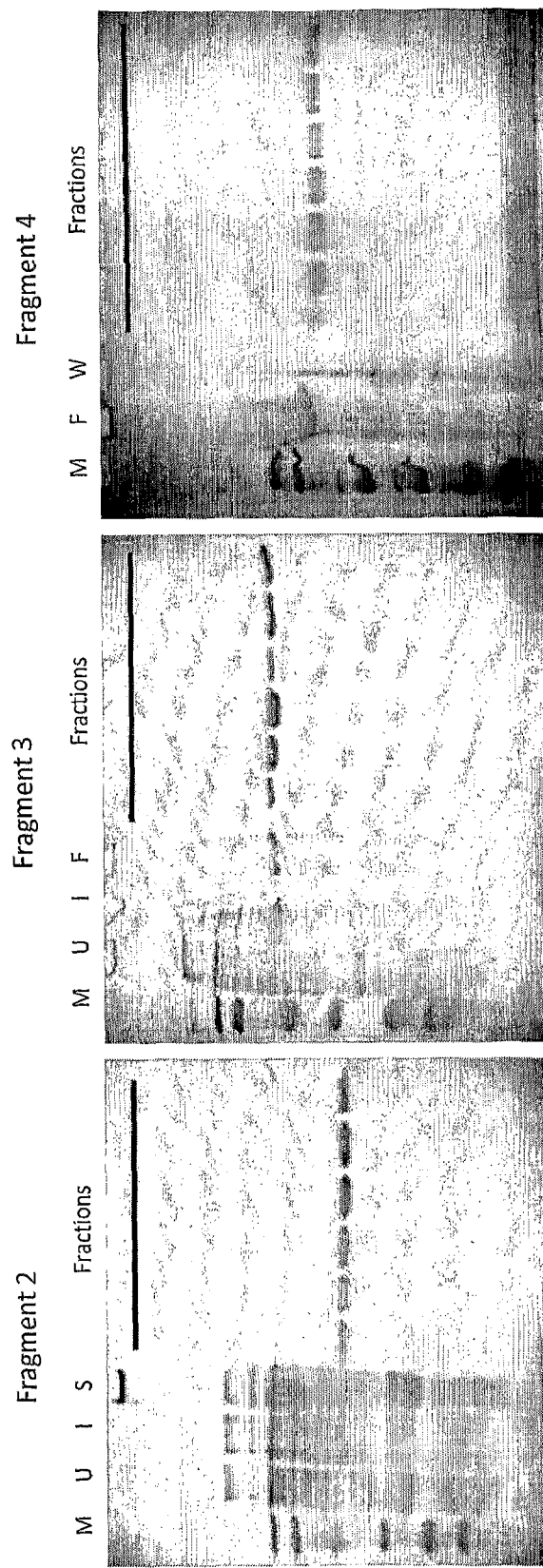

FIG. 11a is the nucleotide sequence of mouse pappalysin 1 fragment 1 (SEQ ID NO: 5); FIG. 11b is the nucleotide sequence of mouse pappalysin 1 fragment 2 (SEQ ID NO: 6); FIG. 11e is the nucleotide sequence of mouse pappalysin 1 fragment 3 (SEQ ID NO: 7); FIG. 11d is the nucleotide sequence of mouse pappalysin 1 fragment 4 (SEQ ID NO: 8);

FIG. 11e is the nucleotide sequence of mouse pappalysin 1 fragment 5 (SEQ ID NO: 9); FIG. 11f is the nucleotide sequence of mouse pappalysin 1 fragment 6 (SEQ ID NO: 10);

FIG. 12a is the nucleotide sequence of human pappalysin 1 fragment 1 (SEQ ID NO: 11); FIG. 12b is the nucleotide sequence of human pappalysin 1 fragment 2 (SEQ ID NO: 12); FIG. 12c is the nucleotide sequence of human pappalysin 1 fragment 3 (SEQ ID NO: 13); FIG. 12d is the nucleotide sequence of human pappalysin 1 fragment 4 (SEQ ID NO: 14); FIG. 12e is the nucleotide sequence of human pappalysin 1 fragment 5 (SEQ ID NO: 15); FIG. 12f is the nucleotide sequence of human pappalysin 1 fragment 6 (SEQ ID NO: 16);

FIG. 13a is the amino acid sequence of mouse pappalysin 1 fragment 1 (SEQ ID NO: 17); FIG. 13b is the amino acid sequence of mouse pappalysin 1 fragment 2 (SEQ ID NO: 18); FIG. 13c is the amino acid sequence of mouse pappalysin 1 fragment 3 (SEQ ID NO: 19); FIG. 13d is the amino acid sequence of mouse pappalysin 1 fragment 4 (SEQ ID NO: 20); FIG. 13e is the amino acid sequence of mouse pappalysin 1 fragment 5 (SEQ ID NO: 21); FIG. 13f is the amino acid sequence of mouse pappalysin 1 fragment 6 (SEQ ID NO: 22);

FIG. 14a is the amino acid sequence of human pappalysin 1 fragment 1 (SEQ ID NO: 23); FIG. 14b is the amino acid sequence of human pappalysin 1 fragment 2 (SEQ ID NO: 24); FIG. 14c is the amino acid sequence of human pappalysin 1 fragment 3 (SEQ ID NO: 25); FIG. 14d is the amino acid sequence of human pappalysin 1 fragment 4 (SEQ ID NO: 26); FIG. 14e is the amino acid sequence of human pappalysin 1 fragment 5 (SEQ ID NO: 27); FIG. 14f is the amino acid sequence of human pappalysin 1 fragment 6 (SEQ ID NO: 28);

FIG. 15 shows pappalysin expression in stable transfectants of B16 cells. Expression was measured by RT-PCR in 4 stable clones after 6 passages (lanes 2-5) or >20 passages in continuous culture (lanes 6-9). The parental B16 cells were shown to be pappalysin negative (lane 1). The pappalysin expression plasmid was amplified as a positive control (lane 10), water was used as a negative control (lane 11), FIG. 16 shows SDS-PAGE analysis of purified protein fragments. Eluted fractions from the purification column were subjected to SDS-PAGE analysis to determine recovery of the desired product and the presence of any contaminating proteins (fractions). Aliquots of uninduced (U) and induced (1) bacterial cultures are shown to indicate that expression was induced. Flow-through (F) and wash (W) samples were also analysed to detect any protein loss during the protein purification procedure.

MATERIALS AND METHODS

Tissue Collection, Isolation, and Culture of Tumor Stem Cells

Human prostatic tissue was obtained, with patient consent, from patients undergoing radical prostatectomy for prostate cancer. Prostate cancer was confirmed by histologic examination of representative adjacent fragments. In some cases, lymph node biopsies were taken if metastasis was suspected. Primary stem cell derived cultures were maintained in complete keratinocyte growth medium [keratinocyte serum-free medium with epidermal growth factor (EGF) and bovine pituitary extract; Invitrogen, Paisley, Scotland]. The medium was also supplemented with 2 ng/mL of leukaemia inhibitory factor (LW; Sigma, Poole, United Kingdom), 2 ng/mL of stem cell factor (Sigma), and 100 ng/mL of cholera toxin (Sigma). CD44/$\alpha_2\beta_1^{hi}$/CD133$^+$ cells were isolated from the tissue, as described previously for normal prostate epithelium (Richardson et al, 2004).

Tissue Culture of Standard Cell Lines

Cell lines were maintained at 37'C/5% $CO_2$ in air in the following growth media: PNT2 R10 medium: RPMI 1640 medium (Invitrogen) containing 10% fetal calf serum and 1% L-glutamine (Invitrogen); PC3 cells H7 medium: HAMS F12 containing 7% fetal calf serum and 1% L-glutamine supplemented with bovine pituitary extract (BPE) and epidermal growth factor (EGF); P4E6 cells K2 medium: KSFM containing 2% fetal calf serum and 1% L-Glutamine.

Immunofluorescent Staining of $\alpha_2\beta_1^{hi}$/CD133$^+$ Cells.

$\alpha_2\beta_1^{hi}$/CD133$^+$ cells were selected directly from cultured cells from tumors before processing for imaging under confocal microscopy by fixation in ice-cold 2:1 methanol:acetone for 20 minutes. Slides were blocked for 1 hour at room temperature in 20% normal goat serum (NGS). After blocking cells were incubated with a rabbit polyclonal antibody to pappalysin A (ab59088, Abcam) diluted in 20% NGS. After washing (3×TBS), cells were further probed with an alexa488-tagged secondary antibody. Cells were mounted in the antiphotobleaching (Dako) medium under coverslips.

Cloning of Mouse PAPPA Fragments into pET22b(+) Expression Vector

Primers were designed to amplify products approximately corresponding to the predicted protein domains of human PAPPA (see FIG. 2 (SEQ ID NO: 2). Each forward and reverse primer also contained a 15 bp sequence homologous to the BamH1 site of the His-tagged protein expression vector pET-22b(+) for use in the In-Fusion cloning system (Clontech—see below). PCR was carried using KOD Hot Start DNA polymerase (Novagen) using the following conditions: 95° C. for 2 mins followed 25 cycles of 95° C. 10 secs, 55° C. 10 secs, 70° C. 15 secs. Products were run on 1% agarose gel containing 1/10,000 dilution of GelRed (Invitrogen). Bands were visualized using a UV transilluminator (GeneGenius).

pET-22b(+) was linearized with BamH1 (37° C., 3 h) and products run on a 0.8% agarose gel stained with GelRed. A band corresponding to linearized vector was excised and the DNA purified using a Qiagen Gel Extraction kit following the manufacturer's protocol.

Insertion of the fragment DNA into the vector was accomplished using the Clontech In-Fusion Advantage kit following manufacturer's instructions. The resulting constructs were transformed into DH5α competent bacteria followed by culture on Luria broth (LB) agar containing ampicillin (50 ug/ml; Sigma). Plates were incubated overnight at 37° C. Individual colonies were picked into 5 ml LB containing ampicillin and incubated overnight in a shaker incubator. DNA was extracted using a Qiaprep Spin Miniprep kit (Qiagen) following manufacturer's instructions. DNA sequencing confirmed that the insert was in frame with the His tag required for purification (Technology Facility, University of York) The construct was transformed into Rosetta-gami2 (DE3) pLysS expression hosts.

Induction of Protein Expression

Bulk inductions were carried out using the same conditions as described above. Rosetta-gami2 (DE3) pLysS cells containing the relevant pappalysin fragment were inoculated into 10 ml LB with ampicillin (50 ug/ml; Sigma) and incubated at 37° C. in a shaker incubator. When the $OD_{600}$ reached 0.5, the culture was added to 500 ml of LB containing ampicillin. When the OD600 reached 0.5 units 1 mM IPTG was added and the culture incubated for a further 2 hours. Cells were pelleted by centrifugation, resuspended in a wash buffer (Tris HCl 50 mM; EDTA 2 mM, NaCl 150 mM pH 7.9) and pelleted once more. Dry pellets were stored at −80° C. until purification.

Purification Under Denaturing Conditions

Preliminary experiments showed that the fragments were packaged into insoluble inclusion bodies, therefor; fragments were purified under denaturing conditions. Bacterial cell pellets from 500 ml cultures were resuspended in 10 ml PBS followed by sonication on ice (Soniprep 150, MSE; 4×30 sec. bursts interspersed with 15 sec. cooling). Lysed culture was spun at 10,000×g for 15 minutes. The supernatant was discarded and the pellet of insoluble material was resuspended in 10 ml of PBS and centrifuged once more, The resulting pellet was resuspended in a guanidine lsyis buffer. Initially the pellet was resuspended in 5 ml resuspension buffer (sodium dihydrogen orthophosphate 20 mM; NaCl 0.5M pH 7.8) and 15 ml of guanidine lysis buffer added (sodium dihydrogen orthophosphate 20 mM; NaCl 0.5M, guanidine HCl 8M ph7.8) resulting in a final concentration of guanidine HCl of 6M. The solubilised protein was incubated at room temperature on a rotating shaker for 10 minutes followed by filtration through a 0.80 □m syringe filter.

Purification was carried out using a 1 ml HisTrap column (GE Healthcare) charged with 3% $NiSO_4$ attached to a AKTA purifier (Amersham). The solubilised protein was passed over the column at a rate of 1 ml/min with a denaturing binding buffer (sodium dihydrogen orthophosphate 20 mM; NaCl 0.5M, Urea 8M pH7.8). The column was washed using a denaturing wash buffer (sodium dihydrogen orthophosphate 20 mM; NaCl 0.5M, Urea 8M pH6) which was gradually replaced by native wash buffer (sodium dihydrogen orthophosphate 25 mM; NaCl 0.5M, imidazole 5 mM pH 8) over a 30 mins period. A linear elution was carried out by exchanging the native wash buffer with a native elution buffer (sodium dihydrogen orthophosphate 25 mM; NaCl 0.5M, imidazole 500 mM pH 8) over 15 minutes such that a gradient of 5 mM to 500 mM imididazole was created over time. 1 ml fractions were collected from the elution at 1 minute intervals.

Buffer Exchange and Concentration of Protein

After PAGE analysis of the eluted fragments, fractions with high expression were selected for buffer exchange into PBS and further concentration. Fractions were pooled and placed in a Vivaspin 20. PBS was added to make the volume up to 20 ml followed by centrifugation at 4000 rpm until the volume was reduced to 5 ml. PBS was added to 20 ml and the process repeated twice more. Finally the he volume was further reduced to 1 ml. Protein concentration was quantified using a Nanodrop spectrophotometer.

Culture of B16 Cells

B16 mouse melanoma cells were maintained in R10 growth medium which is comprised of RPMI1640 medium supplemented with 10% foetal calf serum (PAA Laboratories Ltd. Yeovil, UK) and 1% L-Glutamine (Invitrogen, Paisley, UK).

Stable Transfection of B16 cells

B16 cells were plated in 25 $cm^2$ flasks at $5 \times 10^5$ cells/flask and incubated at 37° C. in R10 growth medium for 24 h prior to transfection. Cells were transfected with 6.5 μg/flask of the pLNCX-PAPPA expression vector using Oligofectamine liposome transfection reagent according to the manufacturer's instructions (Invitrogen, Paisley, UK). Briefly, DNA was mixed with OptiMEM transfection medium (Invitrogen, Paisley, UK). In order to select stable transfectants growth media was changed to $R10^{-4}$-600 μg/ml G418 72 h after transfection. Selection was maintained for 10-14 days to allow the growth of G418 resistant colonies. The cells were then re-plated at one cell/well in 96-well tissue culture plates and maintained in R10+600 μg/ml G418.

EXAMPLE

Pappalysin expression is consistently cytoplasmic in all three cell lines tested; see FIGS. 5, 6 and 7. This is normal for a secreted protein since the secreted component cannot be detected using this technique. Expression is higher in the cancer cell lies (P4E6 and PC3) than the benign cell line (PNT2). Interestingly pappalysin expression is higher in the early stage cancer line P4E6 than the advanced stage cell line PC3 which was derived from a bone metastasis. In primary cells expression is higher on average in cancer cells compared to benign. In the cancer patient expression is higher in the α2β1high/CD133+ stem cell and α2β1high/CD133+ progenitor cell populations compared to the more differentiated α2β1 low population. A similar immunofluoresence staining pattern with respect to pappalysin 2 is shown by P4E6, PC3 and PNT2 cells, see FIG. 8.

Figure 10:
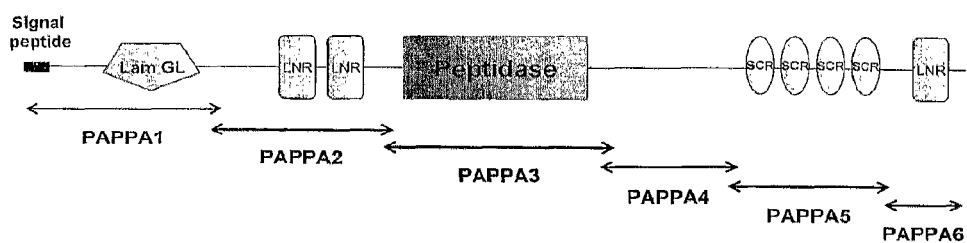
FIG. 10 is a schematic representation of pappalysin and domains 1-6 from which DNA and immunogenic protein fragments are derived.

The stable B16 melanoma cell transfectants are used in an in vivo model to test the efficacy of vaccines disclosed herein. Expression of pappalysin in cloned cell lines is shown in FIG. 15. FIG. 16 describes the recombinant expression of selected pappalysin fragments 2, 3 and 4 which are described in FIG. 10.

---

The invention claimed is:

1. An immunogenic composition comprising an antigenic pappalysin polypeptide fragment and an adjuvant and/or carrier, wherein the antigenic pappalysin polypeptide consists of the amino acid sequence set forth in SEQ ID NO: 26.

2. The composition of claim 1 wherein the adjuvant is a cytokine selected from the group-consisting of GMCSF (granulocyte colony-stimulating factor), interferon gamma, interferon alpha, interferon beta, interleukin 12, interleukin 23, interleukin 17, interleukin 2, interleukin 1, TGF (transforming growth factor), TNFα (tumor necrosis factor alpha), and TNFβ (tumor necrosis factor beta).

3. The composition claim 1 wherein the adjuvant is a TLR (toll-like receptor) agonist.

4. The composition of claim 3 wherein the TLR agonist is selected from the group consisting of: CpG oligonucleotides, flagellin, monophosphoryl lipid A, poly I:C and derivatives thereof.

5. The composition of claim 4 wherein the adjuvant is a CpG oligonucleotide.

6. The composition of claim 1 wherein the adjuvant is a bacterial cell wall derivative selected from the group consisting of muramyl dipeptide (MDP) and trehetose dycorynemycolate (TDM).

7. A composition comprising a nucleic acid molecule encoding an antigenic pappalysin polypeptide fragment wherein when said nucleic acid molecule is expressed the antigenic pappalysin polypeptide fragment consisting of the amino acid sequence set forth in SEQ ID NO: 26 is produced.

8. The composition of claim 7 wherein the nucleic acid molecule is part of an expression vector adapted to express the antigenic pappalysin polypeptide fragment.

9. A method of vaccinating a subject suffering from or having a predisposition to cancer comprising administering an effective amount of an immunogenic composition comprising an antigenic pappalysin polypeptide fragment and an adjuvant and/or carrier wherein the antigenic pappalysin polypeptide fragment consists of the amino acid sequence set forth in SEQ ID NO: 26.

10. The method of claim 9 wherein the cancer is prostate cancer.

11. The method of claim 10 wherein the cancer is lung cancer.

* * * * *

SEQUENCE LISTING

```
<160> NUMBER OF SEQ ID NOS: 28

<210> SEQ ID NO 1
<211> LENGTH: 4884
<212> TYPE: DNA
<213> ORGANISM: Homo sapiens

<400> SEQUENCE: 1
atgcggctct ggagttgggt gctgcacctg gggctgctga gcgccgcgct gggctgcggg     60
ctggccgagc gtccccgccg ggcccggaga gacccgcggg ccggccgacc cccgcgcccc    120
gccgccggcc cggccacctg cgccacccgg gcggcccgcg gccgccgcgc ctcgccgccg    180
ccgccgccgc cgccgggcgg tgcctgggaa gccgtgcgcg tccccggcg gcggcagcag    240 cgggaggcga ggggcgccac cgaggagccg agcccgccga gcgggcgct ctatttcagc    300 gggcgaggcg agcagctgcg cctccgggcc gacctcgagc tgccccggga cgcgttcacg    360
```

```
ctgcaagtgt ggctgcgagc ggagggggc cagaggtctc cggcagtgat cacagggctg    420
tatgacaaat gttcttatat ctcacgtgac cgaggatggg tcgtgggcat tcacaccatc    480
agtgaccaag acaacaaaga cccacgctac tttttctcct tgaagacaga ccgagcccgg    540
caagtgacca ccatcaatgc ccaccgcagc tacctcccag gccagtgggt atacctagct    600
gccacctatg atgggcagtt catgaagctc tatgtgaatg gtgcccaggt ggccacctct    660
ggggaacaag tgggtggcat attcagccca ctgacccaga agtgcaaagt gctcatgtta    720 ggggcagtg ccctgaatca aactaccgg ggctacatcg agcacttcag tctgtggaag    780
gtggccagga ctcagcggga gatactgtct gacatgaaaa cccatggcgc ccacactgct    840
ctacctcagc tcctcctcca ggagaactgg acaatgtga agcatgcctg gtcccccatg    900
aaggatggca gcagcccaa agtggaattc agcaatgccc acggctttct gctggacacg    960
agtctggagc ctcctctgtg cggacagaca ttgtgtgaca acacagaggt cattgccagc   1020
tacaatcagc tctcaagttt ccgccagccc aaggtggtgc gctaccgcgt ggtcaacctc   1080
tatgaagatg atcataagaa cccgacggtg acgcgcgagc aggtggactt ccagcaccat   1140
cagctggctg aggccttcaa gcaatacaac atctcctggg agctgacgt gctggaggtg   1200 agcaactcct cccttcgccg ccgcctcatc ctggccaact gtgacatcag caagattggg   1260
gatgagaact gtgaccccga gtgcaaccac acgctgacgg gccacgacgg cggggattgc   1320
cgccacctgc gccaccctgc cttcgtgaag aagcagcaca cgggggtgtg tgacatggac   1380
tgcaactatg aacggttcaa ctttgatggt ggagagtgct gtgaccctga atcaccaat   1440 gtcactcaga cttgctttga ccccgactct ccacacagag cctacttgga tgttaatgag   1500
ctgaagaaca ttcttaaatt ggatggatca acacatctca atattttctt tgcaaaatcc   1560
tcagaggagg agttggcagg agtagcaact tggccatggg acaaggaggc cctgatgcac   1620
ttaggtggca ttgtcttgaa cccatctttc tatggcatgc ctgggcacac ccacaccatg   1680
atccatgaga ttggtcacag cctgggcctc tatcacgtct ccgaggcat ctcagaaatc   1740 cagtcctgca gtgacccctg catggagaca gagccctcct tcgagactgg agacctctgc   1800
aatgatacca cccagcccc taaacacaag tcctgtggtg acccagggcc aggaaatgac   1860
acctgtggct tcatagctt cttcaacact ccttacaaca acttcatgag ctatgcagat   1920
gacgactgta cggactcctt cacgcccaat caagtcgcca gaatgcactg ttacctggac   1980
ctggtctacc agggctggca gccctccagg aaaccagcgc tgttgccct cgccccccaa   2040 gttctgggcc acacaacgga ctctgtgaca ctggagtggt tcccacctat agatggccat   2100
ttctttgaaa gagaattggg atcagcatgt catctttgcc tggaagggag aatcctggtg   2160
cagtatgctt ccaacgcttc ctccccaatg ccctgcagcc catcaggaca ctggagccct   2220
cgtgaagcag aaggtcatcc tgatgttgaa cagccctgta gtccagtgt ccgcacctgg   2280 agcccaaatt cagctgtcaa cccacacacg gttcctccag cctgccctga cctcaaggc   2340 tgctacctcg agctggagtt cctctacccc ttggtccctg agtctctgac catttgggtg   2400
acctttgtct ccactgactg ggactctagt ggagctgtca atgacatcaa actgttggct   2460
gtcagtggga agaacatctc cctgggtcct cagaatgtct ctgtgatgt cccactgacc   2520 atcagactct gggacgtggg cgaggaggtg tatggcatcc aaatctacac gctggatgag   2580
cacctggaga tcgatgctgc catgttgacc tccactgcag acaccccact ctgtctacag   2640
tgtaagcccc tgaagtataa ggtggtccgg gaccctcctc tccagatgga tgtggcctcc   2700
```

-continued

```
atcctacatc tcaataggaa attcgtagac atggatctaa atcttggcag tgtgtaccag    2760
tattgggtca taactatttc aggaactgaa gagagtgagc catcacctgc tgtcacatac    2820
atccatggaa gtgggtactg tggcgatggc attatacaaa aagaccaagg tgaacaatgc    2880
gacgacatga ataagatcaa tggtgatggc tgctcccttt tctgccgaca agaagtctcc    2940
ttcaattgta ttgatgaacc cagccggtgc tatttccatg atggtgatgg ggtatgtgag    3000
gagtttgaac aaaaaaccag cattaaggac tgtggtgtct acacgcccca gggattcctg    3060
gatcagtggg catccaatgc ttcagtatct catcaagacc agcaatgccc aggctgggtc    3120
atcatcggac agccagcagc atcccaggtg tgtcgaacca aggtgataga tctcagtgaa    3180
ggcatttccc agcatgcctg gtaccettgc accatcagct acccatattc ccagctggct    3240
cagaccactt tttggctccg ggcgtatttt tctcaaccaa tggttgccgc agctgtcatt    3300
gtccacctgg tgacggatgg gacatattat ggggaccaaa agcaggagac catcagcgtg    3360
cagctgcttg ataccaaaga tcagagccac gatctaggcc tccatgtcct gagctgcagg    3420
aacaatcccc tgattatccc tgtggtccat gacctcagcc agcccttcta ccacagccag    3480
gcggtacgtg tgagcttcag ttcgcccctg gtcgccatct cggggtggc cctccgttcc    3540
ttcgacaact tgaccccgt caccctgagc agctgccaga gagggagac ctacagccct    3600
gccgagcaga gctgcgtgca cttcgcatgt gagaaaactg actgtccaga gctggctgtg    3660
gagaatgctt ctctcaattg ctccagcagc gaccgctacc acggtgccca gtgtactgtg    3720
agctgccgga caggctacgt gctccagata cggcgggatg atgagctgat caagagccag    3780
acgggaccca gcgtcacagt gacctgtaca gagggcaagt ggaataagca ggtggcctgt    3840
gagccagtcg actgcagcat cccagatcac catcaagtct atgctgcctc cttctcctgc    3900
cctgagggca ccacctttgg cagtcaatgt tccttccagt gccgtcaccc tgcacaattg    3960
aaaggcaaca acagcctcct gacctgcatg gaggatgggc tgtggtcctt cccagaggcc    4020
ctgtgtgagc tcatgtgcct cgctccaccc cctgtgccca tgcagacct ccagaccgcc    4080
cggtgccgag agaataagca caaggtgggc tccttctgca aatacaaatg caagcctgga    4140
taccatgtgc ctggatcctc tcggaagtca aagaaacggg ccttcaagac tcagtgtacc    4200
caggatggca gctggcagga gggagcttgt gttcctgtga cctgtgaccc acctccacca    4260
aaattccatg ggtctacca gtgtactaat ggcttccagt tcaacagtga gtgtaggatc    4320
aagtgtgaag acagtgatgc ctcccaggga cttgggagca atgtcattca ttgccggaaa    4380
gatggcacct ggaacggctc cttccatgtc tgccaggaga tgcaaggcca gtgctcggtt    4440
ccaaacgagc tcaacagcaa cctcaaactg cagtgccctg atggctatgc catagggtcg    4500
gagtgtgcca cctcgtgcct ggaccacaac agcgagtcca tcatcctgcc aatgaacgtg    4560
accgtgcgtg acatccccca ctggctgaac cccacacggg tagagagagt tgtctgcact    4620
gctggtctca gtggtatcc tcaccctgct ctgattcact gtgtcaaagg ctgtgagccc    4680
ttcatgggag acaattattg tgatgccatc aacaaccgag cctttttgcaa ctatgacggt    4740
ggggattgct gcacctccac agtgaagacc aaaaaggtca ccccattccc tatgtcctgt    4800
gatctacaag gtgactgtgc ttgtcggac ccccaggccc aagaacacag ccggaaagac    4860
ctccggggat acagccatgg ctaa                                            4884
```

<210> SEQ ID NO 2
<211> LENGTH: 1627
<212> TYPE: PRT
<213> ORGANISM: Homo sapiens

<400> SEQUENCE: 2

```
Met Arg Leu Trp Ser Trp Val Leu His Leu Gly Leu Leu Ser Ala Ala
1               5                   10                  15

Leu Gly Cys Gly Leu Ala Glu Arg Pro Arg Ala Arg Arg Asp Pro
            20                  25                  30

Arg Ala Gly Arg Pro Pro Arg Pro Ala Ala Gly Pro Ala Thr Cys Ala
            35                  40                  45

Thr Arg Ala Ala Arg Gly Arg Arg Ala Ser Pro Pro Pro Pro Pro Pro
    50                  55                  60

Pro Gly Gly Ala Trp Glu Ala Val Arg Val Pro Arg Arg Arg Gln Gln
65                  70                  75                  80

Arg Glu Ala Arg Gly Ala Thr Glu Glu Pro Ser Pro Pro Ser Arg Ala
                85                  90                  95

Leu Tyr Phe Ser Gly Arg Gly Glu Gln Leu Arg Leu Arg Ala Asp Leu
                100                 105                 110

Glu Leu Pro Arg Asp Ala Phe Thr Leu Gln Val Trp Leu Arg Ala Glu
                115                 120                 125

Gly Gly Gln Arg Ser Pro Ala Val Ile Thr Gly Leu Tyr Asp Lys Cys
130                 135                 140

Ser Tyr Ile Ser Arg Asp Arg Gly Trp Val Val Gly Ile His Thr Ile
145                 150                 155                 160

Ser Asp Gln Asp Asn Lys Asp Pro Arg Tyr Phe Phe Ser Leu Lys Thr
                165                 170                 175

Asp Arg Ala Arg Gln Val Thr Thr Ile Asn Ala His Arg Ser Tyr Leu
                180                 185                 190

Pro Gly Gln Trp Val Tyr Leu Ala Ala Thr Tyr Asp Gly Gln Phe Met
                195                 200                 205

Lys Leu Tyr Val Asn Gly Ala Gln Val Ala Thr Ser Gly Glu Gln Val
210                 215                 220

Gly Gly Ile Phe Ser Pro Leu Thr Gln Lys Cys Lys Val Leu Met Leu
225                 230                 235                 240

Gly Gly Ser Ala Leu Asn His Asn Tyr Arg Gly Tyr Ile Glu His Phe
                245                 250                 255

Ser Leu Trp Lys Val Ala Arg Thr Gln Arg Glu Ile Leu Ser Asp Met
                260                 265                 270

Glu Thr His Gly Ala His Thr Ala Leu Pro Gln Leu Leu Leu Gln Glu
                275                 280                 285

Asn Trp Asp Asn Val Lys His Ala Trp Ser Pro Met Lys Asp Gly Ser
                290                 295                 300

Ser Pro Lys Val Glu Phe Ser Asn Ala His Gly Phe Leu Leu Asp Thr
305                 310                 315                 320

Ser Leu Glu Pro Pro Leu Cys Gly Gln Thr Leu Cys Asp Asn Thr Glu
                325                 330                 335

Val Ile Ala Ser Tyr Asn Gln Leu Ser Ser Phe Arg Gln Pro Lys Val
                340                 345                 350

Val Arg Tyr Arg Val Val Asn Leu Tyr Glu Asp Asp His Lys Asn Pro
                355                 360                 365

Thr Val Thr Arg Glu Gln Val Asp Phe Gln His Gln Leu Ala Glu
                370                 375                 380

Ala Phe Lys Gln Tyr Asn Ile Ser Trp Glu Leu Asp Val Leu Glu Val
385                 390                 395                 400

Ser Asn Ser Ser Leu Arg Arg Arg Leu Ile Leu Ala Asn Cys Asp Ile
```

-continued

```
                405                 410                 415
Ser Lys Ile Gly Asp Glu Asn Cys Asp Pro Glu Cys Asn His Thr Leu
            420                 425                 430

Thr Gly His Asp Gly Gly Asp Cys Arg His Leu Arg His Pro Ala Phe
            435                 440                 445

Val Lys Lys Gln His Asn Gly Val Cys Asp Met Asp Cys Asn Tyr Glu
            450                 455                 460

Arg Phe Asn Phe Asp Gly Gly Glu Cys Cys Asp Pro Glu Ile Thr Asn
465                 470                 475                 480

Val Thr Gln Thr Cys Phe Asp Pro Asp Ser Pro His Arg Ala Tyr Leu
            485                 490                 495

Asp Val Asn Glu Leu Lys Asn Ile Leu Lys Leu Asp Gly Ser Thr His
            500                 505                 510

Leu Asn Ile Phe Phe Ala Lys Ser Ser Glu Glu Leu Ala Gly Val
            515                 520                 525

Ala Thr Trp Pro Trp Asp Lys Glu Ala Leu Met His Leu Gly Gly Ile
            530                 535                 540

Val Leu Asn Pro Ser Phe Tyr Gly Met Pro Gly His Thr His Thr Met
545                 550                 555                 560

Ile His Glu Ile Gly His Ser Leu Gly Leu Tyr His Val Phe Arg Gly
            565                 570                 575

Ile Ser Glu Ile Gln Ser Cys Ser Asp Pro Cys Met Glu Thr Glu Pro
            580                 585                 590

Ser Phe Glu Thr Gly Asp Leu Cys Asn Asp Thr Asn Pro Ala Pro Lys
            595                 600                 605

His Lys Ser Cys Gly Asp Pro Gly Pro Gly Asn Asp Thr Cys Gly Phe
            610                 615                 620

His Ser Phe Phe Asn Thr Pro Tyr Asn Asn Phe Met Ser Tyr Ala Asp
625                 630                 635                 640

Asp Asp Cys Thr Asp Ser Phe Thr Pro Asn Gln Val Ala Arg Met His
            645                 650                 655

Cys Tyr Leu Asp Leu Val Tyr Gln Gly Trp Gln Pro Ser Arg Lys Pro
            660                 665                 670

Ala Pro Val Ala Leu Ala Pro Gln Val Leu Gly His Thr Thr Asp Ser
            675                 680                 685

Val Thr Leu Glu Trp Phe Pro Pro Ile Asp Gly His Phe Phe Glu Arg
            690                 695                 700

Glu Leu Gly Ser Ala Cys His Leu Cys Leu Glu Gly Arg Ile Leu Val
705                 710                 715                 720

Gln Tyr Ala Ser Asn Ala Ser Ser Pro Met Pro Cys Ser Pro Ser Gly
            725                 730                 735

His Trp Ser Pro Arg Glu Ala Glu Gly His Pro Asp Val Glu Gln Pro
            740                 745                 750

Cys Lys Ser Ser Val Arg Thr Trp Ser Pro Asn Ser Ala Val Asn Pro
            755                 760                 765

His Thr Val Pro Pro Ala Cys Pro Glu Pro Gln Gly Cys Tyr Leu Glu
            770                 775                 780

Leu Glu Phe Leu Tyr Pro Leu Val Pro Glu Ser Leu Thr Ile Trp Val
785                 790                 795                 800

Thr Phe Val Ser Thr Asp Trp Asp Ser Ser Gly Ala Val Asn Asp Ile
            805                 810                 815

Lys Leu Leu Ala Val Ser Gly Lys Asn Ile Ser Leu Gly Pro Gln Asn
            820                 825                 830
```

```
Val Phe Cys Asp Val Pro Leu Thr Ile Arg Leu Trp Asp Val Gly Glu
        835                 840                 845

Glu Val Tyr Gly Ile Gln Ile Tyr Thr Leu Asp Glu His Leu Glu Ile
        850                 855                 860

Asp Ala Ala Met Leu Thr Ser Thr Ala Asp Thr Pro Leu Cys Leu Gln
865                 870                 875                 880

Cys Lys Pro Leu Lys Tyr Lys Val Val Arg Asp Pro Leu Gln Met
                885                 890                 895

Asp Val Ala Ser Ile Leu His Leu Asn Arg Lys Phe Val Asp Met Asp
                900                 905                 910

Leu Asn Leu Gly Ser Val Tyr Gln Tyr Trp Val Ile Thr Ile Ser Gly
                915                 920                 925

Thr Glu Glu Ser Glu Pro Ser Pro Ala Val Thr Tyr Ile His Gly Ser
        930                 935                 940

Gly Tyr Cys Gly Asp Gly Ile Ile Gln Lys Asp Gln Gly Glu Gln Cys
945                 950                 955                 960

Asp Asp Met Asn Lys Ile Asn Gly Asp Gly Cys Ser Leu Phe Cys Arg
                965                 970                 975

Gln Glu Val Ser Phe Asn Cys Ile Asp Glu Pro Ser Arg Cys Tyr Phe
                980                 985                 990

His Asp Gly Asp Gly Val Cys Glu Glu Phe Glu Gln Lys Thr Ser Ile
                995                 1000                1005

Lys Asp Cys Gly Val Tyr Thr Pro Gln Gly Phe Leu Asp Gln Trp
        1010                1015                1020

Ala Ser Asn Ala Ser Val Ser His Gln Asp Gln Gln Cys Pro Gly
        1025                1030                1035

Trp Val Ile Ile Gly Gln Pro Ala Ala Ser Gln Val Cys Arg Thr
        1040                1045                1050

Lys Val Ile Asp Leu Ser Glu Gly Ile Ser Gln His Ala Trp Tyr
        1055                1060                1065

Pro Cys Thr Ile Ser Tyr Pro Tyr Ser Gln Leu Ala Gln Thr Thr
        1070                1075                1080

Phe Trp Leu Arg Ala Tyr Phe Ser Gln Pro Met Val Ala Ala Ala
        1085                1090                1095

Val Ile Val His Leu Val Thr Asp Gly Thr Tyr Tyr Gly Asp Gln
        1100                1105                1110

Lys Gln Glu Thr Ile Ser Val Gln Leu Leu Asp Thr Lys Asp Gln
        1115                1120                1125

Ser His Asp Leu Gly Leu His Val Leu Ser Cys Arg Asn Asn Pro
        1130                1135                1140

Leu Ile Ile Pro Val Val His Asp Leu Ser Gln Pro Phe Tyr His
        1145                1150                1155

Ser Gln Ala Val Arg Val Ser Phe Ser Ser Pro Leu Val Ala Ile
        1160                1165                1170

Ser Gly Val Ala Leu Arg Ser Phe Asp Asn Phe Asp Pro Val Thr
        1175                1180                1185

Leu Ser Ser Cys Gln Arg Gly Glu Thr Tyr Ser Pro Ala Glu Gln
        1190                1195                1200

Ser Cys Val His Phe Ala Cys Glu Lys Thr Asp Cys Pro Glu Leu
        1205                1210                1215

Ala Val Glu Asn Ala Ser Leu Asn Cys Ser Ser Ser Asp Arg Tyr
        1220                1225                1230
```

His Gly Ala Gln Cys Thr Val Ser Cys Arg Thr Gly Tyr Val Leu
1235                     1240                    1245

Gln Ile Arg Arg Asp Asp Glu Leu Ile Lys Ser Gln Thr Gly Pro
1250                     1255                    1260

Ser Val Thr Val Thr Cys Thr Glu Gly Lys Trp Asn Lys Gln Val
1265                     1270                    1275

Ala Cys Glu Pro Val Asp Cys Ser Ile Pro Asp His His Gln Val
1280                     1285                    1290

Tyr Ala Ala Ser Phe Ser Cys Pro Glu Gly Thr Thr Phe Gly Ser
1295                     1300                    1305

Gln Cys Ser Phe Gln Cys Arg His Pro Ala Gln Leu Lys Gly Asn
1310                     1315                    1320

Asn Ser Leu Leu Thr Cys Met Glu Asp Gly Leu Trp Ser Phe Pro
1325                     1330                    1335

Glu Ala Leu Cys Glu Leu Met Cys Leu Ala Pro Pro Pro Val Pro
1340                     1345                    1350

Asn Ala Asp Leu Gln Thr Ala Arg Cys Arg Glu Asn Lys His Lys
1355                     1360                    1365

Val Gly Ser Phe Cys Lys Tyr Lys Cys Lys Pro Gly Tyr His Val
1370                     1375                    1380

Pro Gly Ser Ser Arg Lys Ser Lys Lys Arg Ala Phe Lys Thr Gln
1385                     1390                    1395

Cys Thr Gln Asp Gly Ser Trp Gln Glu Gly Ala Cys Val Pro Val
1400                     1405                    1410

Thr Cys Asp Pro Pro Pro Lys Phe His Gly Leu Tyr Gln Cys
1415                     1420                    1425

Thr Asn Gly Phe Gln Phe Asn Ser Glu Cys Arg Ile Lys Cys Glu
1430                     1435                    1440

Asp Ser Asp Ala Ser Gln Gly Leu Gly Ser Asn Val Ile His Cys
1445                     1450                    1455

Arg Lys Asp Gly Thr Trp Asn Gly Ser Phe His Val Cys Gln Glu
1460                     1465                    1470

Met Gln Gly Gln Cys Ser Val Pro Asn Glu Leu Asn Ser Asn Leu
1475                     1480                    1485

Lys Leu Gln Cys Pro Asp Gly Tyr Ala Ile Gly Ser Glu Cys Ala
1490                     1495                    1500

Thr Ser Cys Leu Asp His Asn Ser Glu Ser Ile Ile Leu Pro Met
1505                     1510                    1515

Asn Val Thr Val Arg Asp Ile Pro His Trp Leu Asn Pro Thr Arg
1520                     1525                    1530

Val Glu Arg Val Val Cys Thr Ala Gly Leu Lys Trp Tyr Pro His
1535                     1540                    1545

Pro Ala Leu Ile His Cys Val Lys Gly Cys Glu Pro Phe Met Gly
1550                     1555                    1560

Asp Asn Tyr Cys Asp Ala Ile Asn Asn Arg Ala Phe Cys Asn Tyr
1565                     1570                    1575

Asp Gly Gly Asp Cys Cys Ser Thr Val Lys Thr Lys Lys Val
1580                     1585                    1590

Thr Pro Phe Pro Met Ser Cys Asp Leu Gln Gly Asp Cys Ala Cys
1595                     1600                    1605

Arg Asp Pro Gln Ala Gln Glu His Ser Arg Lys Asp Leu Arg Gly
1610                     1615                    1620

Tyr Ser His Gly

1625

<210> SEQ ID NO 3
<211> LENGTH: 2284
<212> TYPE: DNA
<213> ORGANISM: Homo sapiens

<400> SEQUENCE: 3

```
atgataactg cactgacaac ttcactccta accaagtggc ccgaatgcat tgctatttgg      60
acctagtcta tcagcagtgg actgaaagca gaaagcccac ccccatcccc attccaccta     120
tggtcatcgg acagaccaac aagtccctca ctatccactg ctgcctcct attagtggag      180
ttgtatatga cagggcctca ggcagcttgt gtggcgcttg cactgaagat gggacctttc     240
gtcagtatgt gcacacagct tcctcccggc gggtgtgtga ctcctcaggt tattggaccc     300
cagaggaggc tgtggggcct cctgatgtgg atcagccctg cgagccaagc ttacaggcct     360
ggagccctga gtccacctg taccacatga acatgacggt ccctgcccc acagaaggct      420
gtagcttgga gctgctcttc aacacccgg tccaagccga caccctcacc ctgtgggtca      480
cttccttctt catggagtcc tcgcaggtcc tctttgacac agagatcttg ctggaaaaca     540
aggagtcagt gcacctgggc cccttagaca cttctctgtga catcccactc accatcaaac    600
tgcacgtgga tgggaaggtg tcggggggtga agtctacac ctttgatgag aggatagaga      660
ttgatgcagc actcctgact tctcagcccc acagtccctt gtgctctggc tgcaggcctg     720
tgaggtacca ggttctccgc gatccccat tgccagtgg tttgcccgtg gtggtgacac       780
attctcacag gaagttcacg gacgtggagg tcacacctgg acagatgtat cagtaccaag     840
ttctagctga agctggagga gaactgggag aagcttcgcc tcctctgaac cacattcatg     900
gagctcctta ttgtggagat gggaaggtgt cagagagact gggagaagag tgtgatgatg     960
gagaccttgt gagcggagat ggctgctcca aggtgtgtga gctggaggaa ggtttcaact    1020
gtgtaggaga gccaagcctt tgctacatgt atgaggaga tggcatatgt gaaccttttg     1080
agagaaaaac cagcattgta gactgtggca tctacactcc caaggatac ttggatcaat     1140
gggctacccg gcttactcc tctcatgaag acaagaagaa gtgtcctgtt tccttggtaa      1200
ctggagaacc tcattccta atttgcacat cataccatcc agatttaccc aaccaccgtc     1260
ccctaactgg ctggttttccc tgtgttgcca gtgaaaatga aactcaggat gacaggagtg     1320
aacagccaga aggtagcctg aagaaagagg atgaggtttg gctcaaagtg tgtttcaata    1380
gaccaggaga ggccagagca attttttattt ttttgacaac tgatggccta gttcccggag    1440
agcatcagca gccgacagtg actctctacc tgaccgatgt ccgtggaagc aaccactctc    1500
ttggaaccta tggactgtca tgccagcata tccactgat tatcaatgtg acccatcacc     1560
agaatgtcct tttccaccat accacctcag tgctgctgaa tttctcatcc ccacgggtcg    1620
gcatctcagc tgtggctcta aggacatcct cccgcattgg tctttcggct cccagtaact    1680
gcatctcaga ggacgagggg cagaatcatc agggacagag ctgtatccat cggccctgtg    1740
ggaagcagga cagctgtccg tcattgctgc ttgatcatgc tgatgtggtg aactgtacct    1800
ctataggccc aggtctcatg aagtgtgcta tcacttgtca aaggggattt gcccttcagg    1860
ccagcagtgg gcagtacatc aggcccatgc agaaggaaat tctgctcaca tgttcttctg    1920
ggcactggga ccagaatgtg agctgccttc ccgtggactg cggtgttccc gacccgtctt    1980
tggtgaacta tgcaaacttc tcctgctcag agggaaccaa atttctgaaa cgctgctcaa    2040
tctcttgtgt cccaccagcc aagctgcaag gactgagccc atggctgaca tgtcttgaag    2100
```

```
atggtctctg gtctctccct gaagtctact gcaagttgga gtgtgatgct ccccctatta    2160
ttctgaatgc caacttgctc ctgcctcact gcctccagga caaccacgac gtgggcacca    2220
tctgcaaata tgaatgcaaa ccagggtact atgtggcaga aagtgcagag ggtaaagtca    2280
ggaa                                                                  2284
```

<210> SEQ ID NO 4
<211> LENGTH: 1791
<212> TYPE: PRT
<213> ORGANISM: Homo sapiens

<400> SEQUENCE: 4

```
Met Met Cys Leu Lys Ile Leu Arg Ile Ser Leu Ala Ile Leu Ala Gly
1               5                   10                  15

Trp Ala Leu Cys Ser Ala Asn Ser Glu Leu Gly Trp Thr Arg Lys Lys
            20                  25                  30

Ser Leu Val Glu Arg Glu His Leu Asn Gln Val Leu Leu Glu Gly Glu
        35                  40                  45

Arg Cys Trp Leu Gly Ala Lys Val Arg Pro Arg Ala Ser Pro Gln
    50                  55                  60

His His Leu Phe Gly Val Tyr Pro Ser Arg Ala Gly Asn Tyr Leu Arg
65                  70                  75                  80

Pro Tyr Pro Val Gly Glu Gln Glu Ile His His Thr Gly Arg Ser Lys
                85                  90                  95

Pro Asp Thr Glu Gly Asn Ala Val Ser Leu Val Pro Pro Asp Leu Thr
            100                 105                 110

Glu Asn Pro Ala Gly Leu Arg Gly Ala Val Glu Glu Pro Ala Ala Pro
        115                 120                 125

Trp Val Gly Asp Ser Pro Ile Gly Gln Ser Glu Leu Leu Gly Asp Asp
    130                 135                 140

Asp Ala Tyr Leu Gly Asn Gln Arg Ser Lys Glu Ser Leu Gly Glu Ala
145                 150                 155                 160

Gly Ile Gln Lys Gly Ser Ala Met Ala Ala Thr Thr Thr Ala Ile
                165                 170                 175

Phe Thr Thr Leu Asn Glu Pro Lys Pro Glu Thr Gln Arg Arg Gly Trp
            180                 185                 190

Ala Lys Ser Arg Gln Arg Arg Gln Val Trp Lys Arg Ala Glu Asp
        195                 200                 205

Gly Gln Gly Asp Ser Gly Ile Ser Ser His Phe Gln Pro Trp Pro Lys
    210                 215                 220

His Ser Leu Lys His Arg Val Lys Lys Ser Pro Pro Glu Glu Ser Asn
225                 230                 235                 240

Gln Asn Gly Gly Glu Gly Ser Tyr Arg Glu Ala Glu Thr Phe Asn Ser
                245                 250                 255

Gln Val Gly Leu Pro Ile Leu Tyr Phe Ser Gly Arg Arg Glu Arg Leu
            260                 265                 270

Leu Leu Arg Pro Glu Val Leu Ala Glu Ile Pro Arg Glu Ala Phe Thr
        275                 280                 285

Val Glu Ala Trp Val Lys Pro Glu Gly Gly Gln Asn Asn Pro Ala Ile
    290                 295                 300

Ile Ala Gly Val Phe Asp Asn Cys Ser His Thr Val Ser Asp Lys Gly
305                 310                 315                 320

Trp Ala Leu Gly Ile Arg Ser Gly Lys Asp Lys Gly Lys Arg Asp Ala
                325                 330                 335
```

```
Arg Phe Phe Phe Ser Leu Cys Thr Asp Arg Val Lys Ala Thr Ile
            340                 345                 350

Leu Ile Ser His Ser Arg Tyr Gln Pro Gly Thr Trp Thr His Val Ala
        355                 360                 365

Ala Thr Tyr Asp Gly Arg His Met Ala Leu Tyr Val Asp Gly Thr Gln
370                 375                 380

Val Ala Ser Ser Leu Asp Gln Ser Gly Pro Leu Asn Ser Pro Phe Met
385                 390                 395                 400

Ala Ser Cys Arg Ser Leu Leu Gly Gly Asp Ser Ser Glu Asp Gly
                405                 410                 415

His Tyr Phe Arg Gly His Leu Gly Thr Leu Val Phe Trp Ser Thr Ala
            420                 425                 430

Leu Pro Gln Ser His Phe Gln His Ser Ser Gln His Ser Ser Gly Glu
                435                 440                 445

Glu Glu Ala Thr Asp Leu Val Leu Thr Ala Ser Phe Glu Pro Val Asn
        450                 455                 460

Thr Glu Trp Val Pro Phe Arg Asp Glu Lys Tyr Pro Arg Leu Glu Val
465                 470                 475                 480

Leu Gln Gly Phe Glu Pro Glu Pro Glu Ile Leu Ser Pro Leu Gln Pro
                485                 490                 495

Pro Leu Cys Gly Gln Thr Val Cys Asp Asn Val Glu Leu Ile Ser Gln
            500                 505                 510

Tyr Asn Gly Tyr Trp Pro Leu Arg Gly Glu Lys Val Ile Arg Tyr Gln
        515                 520                 525

Val Val Asn Ile Cys Asp Asp Glu Gly Leu Asn Pro Ile Val Ser Glu
530                 535                 540

Glu Gln Ile Arg Leu Gln His Glu Ala Leu Asn Glu Ala Phe Ser Arg
545                 550                 555                 560

Tyr Asn Ile Ser Trp Gln Leu Ser Val His Gln Val His Asn Ser Thr
                565                 570                 575

Leu Arg His Arg Val Val Leu Val Asn Cys Glu Pro Ser Lys Ile Gly
            580                 585                 590

Asn Asp His Cys Asp Pro Glu Cys Glu His Pro Leu Thr Gly Tyr Asp
        595                 600                 605

Gly Gly Asp Cys Arg Leu Gln Gly Arg Cys Tyr Ser Trp Asn Arg Arg
610                 615                 620

Asp Gly Leu Cys His Val Glu Cys Asn Asn Met Leu Asn Asp Phe Asp
625                 630                 635                 640

Asp Gly Asp Cys Cys Asp Pro Gln Val Ala Asp Val Arg Lys Thr Cys
                645                 650                 655

Phe Asp Pro Asp Ser Pro Lys Arg Ala Tyr Met Ser Val Lys Glu Leu
            660                 665                 670

Lys Glu Ala Leu Gln Leu Asn Ser Thr His Phe Leu Asn Ile Tyr Phe
        675                 680                 685

Ala Ser Ser Val Arg Glu Asp Leu Ala Gly Ala Ala Thr Trp Pro Trp
690                 695                 700

Asp Lys Asp Ala Val Thr His Leu Gly Gly Ile Val Leu Ser Pro Ala
705                 710                 715                 720

Tyr Tyr Gly Met Pro Gly His Thr Asp Thr Met Ile His Glu Val Gly
                725                 730                 735

His Val Leu Gly Leu Tyr His Val Phe Lys Gly Val Ser Glu Arg Glu
            740                 745                 750
```

```
Ser Cys Asn Asp Pro Cys Lys Glu Thr Val Pro Ser Met Glu Thr Gly
            755                 760                 765

Asp Leu Cys Ala Asp Thr Ala Pro Thr Pro Lys Ser Glu Leu Cys Arg
770                 775                 780

Glu Pro Glu Pro Thr Ser Asp Thr Cys Gly Phe Thr Arg Phe Pro Gly
785                 790                 795                 800

Ala Pro Phe Thr Asn Tyr Met Ser Tyr Thr Asp Asp Asn Cys Thr Asp
            805                 810                 815

Asn Phe Thr Pro Asn Gln Val Ala Arg Met His Cys Tyr Leu Asp Leu
            820                 825                 830

Val Tyr Gln Gln Trp Thr Glu Ser Arg Lys Pro Thr Pro Ile Pro Ile
            835                 840                 845

Pro Pro Met Val Ile Gly Gln Thr Asn Lys Ser Leu Thr Ile His Trp
850                 855                 860

Leu Pro Pro Ile Ser Gly Val Val Tyr Asp Arg Ala Ser Gly Ser Leu
865                 870                 875                 880

Cys Gly Ala Cys Thr Glu Asp Gly Thr Phe Arg Gln Tyr Val His Thr
            885                 890                 895

Ala Ser Ser Arg Arg Val Cys Asp Ser Ser Gly Tyr Trp Thr Pro Glu
            900                 905                 910

Glu Ala Val Gly Pro Pro Asp Val Asp Gln Pro Cys Glu Pro Ser Leu
            915                 920                 925

Gln Ala Trp Ser Pro Glu Val His Leu Tyr His Met Asn Met Thr Val
            930                 935                 940

Pro Cys Pro Thr Glu Gly Cys Ser Leu Glu Leu Leu Phe Gln His Pro
945                 950                 955                 960

Val Gln Ala Asp Thr Leu Thr Leu Trp Val Thr Ser Phe Phe Met Glu
            965                 970                 975

Ser Ser Gln Val Leu Phe Asp Thr Glu Ile Leu Leu Glu Asn Lys Glu
            980                 985                 990

Ser Val His Leu Gly Pro Leu Asp Thr Phe Cys Asp Ile Pro Leu Thr
            995                 1000                1005

Ile Lys Leu His Val Asp Gly Lys Val Ser Gly Val Lys Val Tyr
    1010            1015            1020

Thr Phe Asp Glu Arg Ile Glu Ile Asp Ala Ala Leu Leu Thr Ser
    1025            1030            1035

Gln Pro His Ser Pro Leu Cys Ser Gly Cys Arg Pro Val Arg Tyr
    1040            1045            1050

Gln Val Leu Arg Asp Pro Pro Phe Ala Ser Gly Leu Pro Val Val
    1055            1060            1065

Val Thr His Ser His Arg Lys Phe Thr Asp Val Glu Val Thr Pro
    1070            1075            1080

Gly Gln Met Tyr Gln Tyr Gln Val Leu Ala Glu Ala Gly Gly Glu
    1085            1090            1095

Leu Gly Glu Ala Ser Pro Pro Leu Asn His Ile His Gly Ala Pro
    1100            1105            1110

Tyr Cys Gly Asp Gly Lys Val Ser Glu Arg Leu Gly Glu Glu Cys
    1115            1120            1125

Asp Asp Gly Asp Leu Val Ser Gly Asp Gly Cys Ser Lys Val Cys
    1130            1135            1140

Glu Leu Glu Glu Gly Phe Asn Cys Val Gly Glu Pro Ser Leu Cys
    1145            1150            1155

Tyr Met Tyr Glu Gly Asp Gly Ile Cys Glu Pro Phe Glu Arg Lys
```

```
                    1160                1165                1170
Thr  Ser  Ile  Val  Asp  Cys  Gly  Ile  Tyr  Thr  Pro  Lys  Gly  Tyr  Leu
     1175                1180                1185

Asp  Gln  Trp  Ala  Thr  Arg  Ala  Tyr  Ser  Ser  His  Glu  Asp  Lys  Lys
     1190                1195                1200

Lys  Cys  Pro  Val  Ser  Leu  Val  Thr  Gly  Glu  Pro  His  Ser  Leu  Ile
     1205                1210                1215

Cys  Thr  Ser  Tyr  His  Pro  Asp  Leu  Pro  Asn  His  Arg  Pro  Leu  Thr
     1220                1225                1230

Gly  Trp  Phe  Pro  Cys  Val  Ala  Ser  Glu  Asn  Glu  Thr  Gln  Asp  Asp
     1235                1240                1245

Arg  Ser  Glu  Gln  Pro  Glu  Gly  Ser  Leu  Lys  Lys  Glu  Asp  Glu  Val
     1250                1255                1260

Trp  Leu  Lys  Val  Cys  Phe  Asn  Arg  Pro  Gly  Glu  Ala  Arg  Ala  Ile
     1265                1270                1275

Phe  Ile  Phe  Leu  Thr  Thr  Asp  Gly  Leu  Val  Pro  Gly  Glu  His  Gln
     1280                1285                1290

Gln  Pro  Thr  Val  Thr  Leu  Tyr  Leu  Thr  Asp  Val  Arg  Gly  Ser  Asn
     1295                1300                1305

His  Ser  Leu  Gly  Thr  Tyr  Gly  Leu  Ser  Cys  Gln  His  Asn  Pro  Leu
     1310                1315                1320

Ile  Ile  Asn  Val  Thr  His  His  Gln  Asn  Val  Leu  Phe  His  His  Thr
     1325                1330                1335

Thr  Ser  Val  Leu  Leu  Asn  Phe  Ser  Ser  Pro  Arg  Val  Gly  Ile  Ser
     1340                1345                1350

Ala  Val  Ala  Leu  Arg  Thr  Ser  Arg  Ile  Gly  Leu  Ser  Ala  Pro
     1355                1360                1365

Ser  Asn  Cys  Ile  Ser  Glu  Asp  Glu  Gly  Gln  Asn  His  Gln  Gly  Gln
     1370                1375                1380

Ser  Cys  Ile  His  Arg  Pro  Cys  Gly  Lys  Gln  Asp  Ser  Cys  Pro  Ser
     1385                1390                1395

Leu  Leu  Leu  Asp  His  Ala  Asp  Val  Val  Asn  Cys  Thr  Ser  Ile  Gly
     1400                1405                1410

Pro  Gly  Leu  Met  Lys  Cys  Ala  Ile  Thr  Cys  Gln  Arg  Gly  Phe  Ala
     1415                1420                1425

Leu  Gln  Ala  Ser  Ser  Gly  Gln  Tyr  Ile  Arg  Pro  Met  Gln  Lys  Glu
     1430                1435                1440

Ile  Leu  Leu  Thr  Cys  Ser  Ser  Gly  His  Trp  Asp  Gln  Asn  Val  Ser
     1445                1450                1455

Cys  Leu  Pro  Val  Asp  Cys  Gly  Val  Pro  Asp  Pro  Ser  Leu  Val  Asn
     1460                1465                1470

Tyr  Ala  Asn  Phe  Ser  Cys  Ser  Glu  Gly  Thr  Lys  Phe  Leu  Lys  Arg
     1475                1480                1485

Cys  Ser  Ile  Ser  Cys  Val  Pro  Pro  Ala  Lys  Leu  Gln  Gly  Leu  Ser
     1490                1495                1500

Pro  Trp  Leu  Thr  Cys  Leu  Glu  Asp  Gly  Leu  Trp  Ser  Leu  Pro  Glu
     1505                1510                1515

Val  Tyr  Cys  Lys  Leu  Glu  Cys  Asp  Ala  Pro  Pro  Ile  Ile  Leu  Asn
     1520                1525                1530

Ala  Asn  Leu  Leu  Leu  Pro  His  Cys  Leu  Gln  Asp  Asn  His  Asp  Val
     1535                1540                1545

Gly  Thr  Ile  Cys  Lys  Tyr  Glu  Cys  Lys  Pro  Gly  Tyr  Tyr  Val  Ala
     1550                1555                1560
```

```
Glu  Ser  Ala  Glu  Gly  Lys  Val  Arg  Asn  Lys  Leu  Leu  Lys  Ile  Gln
    1565                1570                     1575

Cys  Leu  Glu  Gly  Gly  Ile  Trp  Glu  Gln  Gly  Ser  Cys  Ile  Pro  Val
    1580                1585                     1590

Val  Cys  Glu  Pro  Pro  Pro  Val  Phe  Glu  Gly  Met  Tyr  Glu  Cys
    1595                1600                     1605

Thr  Asn  Gly  Phe  Ser  Leu  Asp  Ser  Gln  Cys  Val  Leu  Asn  Cys  Asn
    1610                1615                     1620

Gln  Glu  Arg  Glu  Lys  Leu  Pro  Ile  Leu  Cys  Thr  Lys  Glu  Gly  Leu
    1625                1630                     1635

Trp  Thr  Gln  Glu  Phe  Lys  Leu  Cys  Glu  Asn  Leu  Gln  Gly  Glu  Cys
    1640                1645                     1650

Pro  Pro  Pro  Pro  Ser  Glu  Leu  Asn  Ser  Val  Glu  Tyr  Lys  Cys  Glu
    1655                1660                     1665

Gln  Gly  Tyr  Gly  Ile  Gly  Ala  Val  Cys  Ser  Pro  Leu  Cys  Val  Ile
    1670                1675                     1680

Pro  Pro  Ser  Asp  Pro  Val  Met  Leu  Pro  Glu  Asn  Ile  Thr  Ala  Asp
    1685                1690                     1695

Thr  Leu  Glu  His  Trp  Met  Glu  Pro  Val  Lys  Val  Gln  Ser  Ile  Val
    1700                1705                     1710

Cys  Thr  Gly  Arg  Arg  Gln  Trp  His  Pro  Asp  Pro  Val  Leu  Val  His
    1715                1720                     1725

Cys  Ile  Gln  Ser  Cys  Glu  Pro  Phe  Gln  Ala  Asp  Gly  Trp  Cys  Asp
    1730                1735                     1740

Thr  Ile  Asn  Asn  Arg  Ala  Tyr  Cys  His  Tyr  Asp  Gly  Gly  Asp  Cys
    1745                1750                     1755

Cys  Ser  Ser  Thr  Leu  Ser  Ser  Lys  Lys  Val  Ile  Pro  Phe  Ala  Ala
    1760                1765                     1770

Asp  Cys  Asp  Leu  Asp  Glu  Cys  Thr  Cys  Arg  Asp  Pro  Lys  Ala  Glu
    1775                1780                     1785

Glu  Asn  Gln
    1790

<210> SEQ ID NO 5
<211> LENGTH: 873
<212> TYPE: DNA
<213> ORGANISM: Mus musculus

<400> SEQUENCE: 5
gacatgcggc tctggagttg ggtgctgcgc ctggggctgc tgagcgccgc gctgggctgc      60
gggctggccg agcgccccg ccgggtccga agagaccctc gggccgtgcg ccccccgcgc     120
cccgccgctg accggccac ctgcgccacc cggccgcccc gcgtcgccg cgcctcgccg      180 ccgccgcctc cgggcggtgc ctgggaagcc gtgcgcgtcc cccggcggcg gcagcagcgg      240
gcggcgaggg gcgccgagga gccgagcccg cctagccggg cgctctattt cagcgggcga      300
ggggagcagc tgcgcctccg ggccgacctg gagctacccc gcgacgcctt acactgcaa      360 gtgtggctgc gagccgaggg tggccagaag tctccagcag tgatcacagg gctgtatgac      420
aaatgttctt atacctcacg tgatcgagga tgggtcatgg gcattcacac caccagtgat      480
caaggcaaca gagatccacg ctactttttc tccttgaaga cagaccgggc caggaaagtg      540
accaccattg atgcccatcg cagctacctc ccaggtcagt gggtacatct agctgctacc      600
tatgatgggc ggctgatgaa gctctatatg aatggtgccc aggtggcaac ttcggctgag      660
```

-continued

```
caagtaggtg gcatattcag cccactgacc cagaagtgta aagtgctcat gttgggggc      720 agtgctctga atcacaactt ccggggccac attgaacact tcagtctatg aaagtagca      780 agaacccagc gagagattgt atccgacatg gaaacccgtg gcctccacac ccctctacct    840
cagctcctcc tccaggagaa ctgggacaac gtg                                  873

<210> SEQ ID NO 6
<211> LENGTH: 792
<212> TYPE: DNA
<213> ORGANISM: Mus musculus

<400> SEQUENCE: 6
gtatccgaca tggaaacccg tggcctccac accctctac ctcagctcct cctccaggag       60
aactgggaca cgtgaagcg cacttggtcc cccatgaagg atggcaacag cccccaggtg      120
gaattcagca atgcccacgg cttcctgttg acactaatt tggagccccc tctttgtggg     180
cagacactgt gtgacaacac agaagtcatc tccagttaca atcagctccc aagttttcgg    240
cagcccaagg tggtccgcta cgtgtggtc aacatctatg atgatcacca tgagaatcca    300
acggtgagct ggcaacagat tgactttcag caccaacagc tggctgaggc ctttcaacac    360
tacaacatct cctgggagct ggaggtactg aatataaaca gttcctctct gcgtcaccgc    420
ctcatcctag ccaactgtga catcagcaag attggggatg aaaaatgtga tccagaatgt    480
aaccatacac tgactggtca tgatggtgga gattgccgcc agctgcgcta ccctgcgttc    540
atgaagaagc agcagaatgg tgtgtgtgac atggactgta actacgaaag gtttaatttt    600
gatggtggag agtgctgtga cccagacatc actgatgtca ctaagacatg ctttgatcct    660
gactctccac acagagccta cttggatgtt aatgagctaa gaacattct tagactggac    720 ggatcaacac atctcaatat tttctttgca aactcttcag aggaggagtt ggcaggagtg    780
gcaacttggc ca                                                          792

<210> SEQ ID NO 7
<211> LENGTH: 1086
<212> TYPE: DNA
<213> ORGANISM: Mus musculus

<400> SEQUENCE: 7
ctggacggat caacacatct caatattttc tttgcaaact cttcagagga ggagttggca     60
ggagtggcaa cttggccatg ggacaaggaa gccctaatgc acttgggcgg tattgtcttg    120
aacccatctt tctatggcat tcccggacac acccacacca tgattcatga gattgggcat    180
agcctgggcc tctatcacat cttccgtggc atctcagaaa tccagtcctg cagtgatccc    240
tgcatggaga cagagccttc atttgaaact ggagacctct gcaatgatac caacccagcc    300
cccaaacaca agttttgtgg agaccctgga ccagggaatg cacttgtgg ctttcatggc    360 ttcttcaaca ctccttacaa caacttcatg agctacgcag atgacgactg tacagactct    420
ttcacgccca atcaagtctc cagaatgcac tgttacctgg acctcgtata ccagagctgg    480 cagcccctcca gaaagccagc acctgtagct cttgcgcccc aggttgtggg gcacacaatg    540
gactctgtga tgctagagtg gttcccaccc atcgatggcc acttctttga aagagaattg    600
ggatcagcat gtgaccttg cctagaaggg agaatcctgg tgcaatatgc tttcaatgcc    660
tcctccccca tgcctgtgg accgtcagga cactggagtc ctcgggaagc agaaggtcac    720
ccagatgttg aacagccctg taatccagt gtccgaacct ggagtccaaa ttcagctgtc    780
aacccacaca cagttcctcc agcctgccct gagccacaag gctgctacct cgagctggaa    840
```

```
tttcgctacc ctttggtccc tgagtctctg accatctggg taaccttttgt ctccagtgat      900 tgggactcta gtggagctgt caatgacatc aaactcttga ctatcagtgg aaagaatatc      960
tctttgggtc ctcagaatgt tttctgtgat atcccactta ccatcagact ccgggatgtg     1020
ggtgaggagg tatatggcat ccaaatctat actcttgatg agcacctgga gattgatgca     1080
gcaatg                                                                1086

<210> SEQ ID NO 8
<211> LENGTH: 1083
<212> TYPE: DNA
<213> ORGANISM: Mus musculus

<400> SEQUENCE: 8
ggtgaggagg tatatggcat ccaaatctat actcttgatg agcacctgga gattgatgca       60
gcaatgctga cctccactgt agacagtcca ctctgcctac agtgtaaacc tctgcagtat      120
aaagtgcttc gagacccacc tctgctagaa gatgtagcct cattactcca cctcaacaga      180
agattcatgg acacggatct gaaacttggc agtgtgtacc agtaccggat tatcaccatt      240
tcaggaaatg aagagagcga gccatcacct gctgccatat acacccacgg aagtgggtac      300
tgtggtgatg gcgttatcca aaaagaccaa ggagaagaat gtgacgacat gaataaggtc      360 aatgggggatg gctgctccct tttctgcaag caagaagttt ccttcaactg cattgatgaa      420
cccagccggt gctatttcca tgatggggat gggatgtgtg aagagtttga acaaaaaact      480
agcattaaag actgtggtgt ctacacgccc cagggtttcc tggatcagtg ggcatccaat      540
gcttcagtat ctcatcaaga ccagcagtgc ccaggttggg ttgtcattgg cagccagcg      600 gcatctcagg tgtgtcgaac caaggtgata gatctcagtg aaggcatttc ccagcatgct      660
tggtatcctt gcaccattac ttacccatac taccatctgc ctcagaccac attctggctc      720
cagacatatt tctctcagcc aatggttgct gcagctgtaa ttattcacct ggtgactgat      780
gggacatact atggggacca aaagcaagag accatcagtg tgcagttgct tgataccaaa      840
gatcaaagcc atgatctagg cctccatgtc ttgagctgca gaaacaatcc cctgattatc      900
cctgtggtcc atgacctcag ccagcccttc taccacagcc aggcggtaca tgtgagcttc      960
agttcgcccc tggtcgccat ctcgggggtg gccctccgct cttttcgacaa ctttgacccc     1020 gtcaccctga gcagctgcca gagaggagag acctacagcc tgctgagca gagctgtgtg     1080 cat                                                                   1083

<210> SEQ ID NO 9
<211> LENGTH: 927
<212> TYPE: DNA
<213> ORGANISM: Mus musculus

<400> SEQUENCE: 9
tgccagagag gagagaccta cagccctgct gagcagagct gtgtgcattt tgcctgtcaa       60
gctgccgact gcccagaact ggccgtgggg aatgcttctc tcaactgttc cagcaaccac      120
cactaccatg gtgcccagtg cactgtgagc tgccagacag gttatgtgct gcagatacag      180
cgggacgatg agctaatcaa gagccaggta gggccaagca tcacagtgac atgtaccgag      240
ggcaaatgga caagcaggt ggcatgtgag ccggtggact gtggtatccc agatcaccat      300
cacgtctatg ctgcctcctt ctcctgtcca gagggtacca cctttggtag aagatgttct      360
tttcagtgtc gccacccctgc ccagctgaaa ggcaacaaca gctttctgac ctgtatggaa      420
```

```
gatggactgt ggtccttccc agaggccttg tgtgagctca tgtgcctcgc ccaccccca      480 gttcccaatg cggacctaca gacagcccgg tgtcgagaga acaagcacaa ggtgggctcc      540
ttctgcaagt acaagtgtaa acctggatac cacgtgcctg gctcatctcg aagtccaag      600 aaacgggctt tcaagactca atgtactcaa gatggcagct ggcaagaggg aacttgtgtg      660
ccggtgactt gtgacccacc tccacccaaa ttccatgggc tctatcaatg cactaatggc      720
ttccagttca atagtgagtg caggatcaag tgtgaagaca gtgatgcctc ccagggccgt      780
gggagcaata tcattcactg ccggaaagat ggcacttgga gtggttcctt ccacgtctgc      840
cgagagatgc aaggccagtg ctcagcccca aaccaactca acagtaacct caaattgcag      900
tgtcctgatg gctatgcaat agggtca                                           927

<210> SEQ ID NO 10
<211> LENGTH: 465
<212> TYPE: DNA
<213> ORGANISM: Mus musculus

<400> SEQUENCE: 10
cgagagatgc aaggccagtg ctcagcccca aaccaactca acagtaacct caaattgcag      60
tgtcctgatg gctatgcaat agggtcagag tgtgccatct cgtgcctgga ccataacagc      120
gagtccatca tccttcccgt taacttgaca gtgcgtgaca taccccattg gatgaacccc      180
acacgagtac agaggattgt ctgcactgct ggtctccagt ggtatcccca ccctgctctg      240
atccactgtg tcaaaggctg tgagccattc atgggagaca actactgtga tgccatcaac      300
aatcgagcct ctgcaactat gatggtgggg gactgctgca cctccacagt aaagaccaaa      360
aaggtcactc cctttcctat gtcctgtgac ctacaaaatg actgcgcctg tcgagaccct      420
gaggcccaag aacacaaccg gaaagatctt cggggatata gccat                       465

<210> SEQ ID NO 11
<211> LENGTH: 882
<212> TYPE: DNA
<213> ORGANISM: Homo sapiens

<400> SEQUENCE: 11
gacatgcggc tctggagttg ggtgctgcac ctggggctgc tgagcgccgc gctgggctgc      60
gggctggccg agcgtccccg ccgggccggg agagacccgc gggccggccg accccgcgc      120 cccgccgccg gcccggccac ctgcgccacc cgggcggccc gcggccgccg cgcctcgccg      180
ccgccgccgc cgccgccggg cggtgcctgg aagccgtgc gcgtcccccg gcggcggcag      240
cagcgggagg cgaggggcgc caccgaggag ccgagcccgc cgagccgggc gctctatttc      300
agcgggcgag gcgagcagct gcgcctccgg gccgacctcg agctgccccg ggacgcgttc      360
acgctgcaag tgtggctgcg agcggagggg ggccagaggt ctccggcagt gatcacaggg      420
ctgtatgaca atgttcctta tatctcacgt gaccgaggat gggtcgtggg cattcacacc      480
atcagtgacc aagacaacaa agacccacgc tacttttcct ccttgaagac agaccgagcc      540
cggcaagtga ccaccatcaa tgcccaccgc agctacctcc aggccagtg ggtataccta      600 gctgccacct atgatgggca gttcatgaag ctctatgtga atggtgccca ggtggccacc      660
tctggggaac aagtgggtgg catattcagc ccactgaccc agaagtgcaa agtgctcatg      720
ttagggggca gtgccctgaa tcacaactac cggggctaca tcgagcactt cagtctgtgg      780
aaggtggcca ggactcagcg ggagatactg tctgacatgg aaacccatgg cgcccacact      840
gctctacctc agctcctcct ccaggagaac tgggacaatg tg                           882
```

<210> SEQ ID NO 12
<211> LENGTH: 792
<212> TYPE: DNA
<213> ORGANISM: Homo sapiens

<400> SEQUENCE: 12

```
ctgtctgaca tggaaaccca tggcgcccac actgctctac ctcagctcct cctccaggag      60
aactgggaca atgtgaagca tgcctggtcc cccatgaagg atggcagcag ccccaaagtg     120
gaattcagca atgcccacgg ctttctgctg acacgagtc tggagcctcc tctgtgcgga      180
cagacattgt gtgacaacac agaggtcatt gccagctaca atcagctctc aagtttccgc     240
cagcccaagg tggtgcgcta ccgcgtggtc aacctctatg aagatgatca taagaacccg     300
acggtgacgc gcgagcaggt ggacttccag caccatcagc tggctgaggc cttcaagcaa     360
tacaacatct cctgggagct ggacgtgctg gaggtgagca actcctccct tcgccgccgc     420
ctcatcctgg ccaactgtga catcagcaag attggggatg agaactgtga ccccgagtgc     480
aaccacacgc tgacgggcca cgacggcggg gattgccgcc acctgcgcca ccctgccttc     540
gtgaagaagg agcacaacgg ggtgtgtgac atggactgca actatgaacg gttcaacttt     600
gatggtggag agtgctgtga ccctgaaatc accaatgtca ctcagacttg ctttgacccc     660
gactctccac acagagccta cttggatgtt aatgagctga gaacattct taaattggat     720
ggatcaacac atctcaatat tttctttgca aaatcctcag aggaggagtt ggcaggagta     780
gcaacttggc ca                                                         792
```

<210> SEQ ID NO 13
<211> LENGTH: 1086
<212> TYPE: DNA
<213> ORGANISM: Homo sapiens

<400> SEQUENCE: 13

```
ttggatggat caacacatct caatattttc tttgcaaaat cctcagagga ggagttggca      60
ggagtagcaa cttggccatg ggacaaggag ccctgatgc acttaggtgg cattgtcttg     120
aacccatctt tctatggcat gcctgggcac acccacacca tgatccatga gattggtcac     180
agcctgggcc tctatcacgt cttccgaggc atctcagaaa tccagtcctg cagtgacccc     240
tgcatggaga cagagccctc cttcgagact ggagacctct gcaatgatac caacccagcc     300
cctaaacaca gtcctgtgg tgacccaggg ccaggaaatg cacctgtgg ctttcatagc      360
ttcttcaaca ctccttacaa caacttcatg agctatgcag atgacgactg tacggactcc     420
ttcacgccca atcaagtcgc cagaatgcac tgttacctgg acctggtcta ccagggctgg     480
cagccctcca ggaaaccagc gcctgttgcc ctcgccccc aagttctggg ccacacaacg     540
gactctgtga cactggagtg gttcccacct atagatggcc atttctttga aagagaattg     600
ggatcagcat gtcatctttg cctggaaggg agaatcctgg tgcagtatgc ttccaacgct     660
tcctccccaa tgccctgcag cccatcagga cactggagcc ctcgtgaagc agaaggtcat     720
cctgatgttg aacagccctg taagtccagt gtccgcacct ggagcccaaa ttcagctgtc     780
aacccacaca cggttcctcc agcctgccct gagcctcaag ctgctacct cgagctggag     840
ttcctctacc ccttggtccc tgagtctctg accatttggg tgacctttgt ctccactgac     900
tgggactcta gtggagctgt caatgacatc aaactgttgg ctgtcagtgg gaagaacatc     960
tccctgggtc ctcagaatgt cttctgtgat gtcccactga ccatcagact ctgggacgtg    1020
```

```
ggcgaggagg tgtatggcat ccaaatctac acgctggatg agcacctgga gatcgatgct    1080
gccatg                                                               1086

<210> SEQ ID NO 14
<211> LENGTH: 1083
<212> TYPE: DNA
<213> ORGANISM: Homo sapiens

<400> SEQUENCE: 14
ggcgaggagg tgtatggcat ccaaatctac acgctggatg agcacctgga gatcgatgct      60
gccatgttga cctccactgc agacacccca ctctgtctac agtgtaagcc cctgaagtat     120
aaggtggtcc gggaccctcc tctccagatg gatgtggcct ccatcctaca tctcaatagg     180
aaattcgtag acatggatct aaatcttggc agtgtgtacc agtattgggt cataactatt     240
tcaggaactg aagagagtga gccatcacct gctgtcacat acatccatgg aagtgggtac     300
tgtggcgatg gcattataca aaaagaccaa ggtgaacaat gcgacgacat gaataagatc     360
aatggtgatg gctgctccct tttctgccga caagaagtct ccttcaattg tattgatgaa     420
cccagccggt gctatttcca tgatggtgat ggggtatgtg aggagtttga acaaaaaacc     480
agcattaagg actgtggtgt ctacacgccc cagggattcc tggatcagtg ggcatccaat     540
gcttcagtat ctcatcaaga ccagcaatgc ccaggctggg tcatcatcgg acagccagca     600
gcatcccagg tgtgtcgaac caaggtgata gatctcagtg aaggcatttc ccagcatgcc     660
tggtacccct gcaccatcag ctacccatat tcccagctgg ctcagaccac ttttttggctc    720 cgggcgtatt tttctcaacc aatggttgcc gcagctgtca ttgtccacct ggtgacggat     780
gggacatatt atgggaccaa aaagcaggag accatcagcg tgcagctgct tgataccaaa     840
gatcagagcc acgatctagg cctccatgtc ctgagctgca ggaacaatcc cctgattatc     900
cctgtggtcc atgacctcag ccagcccttc taccacagcc aggcggtacg tgtgagcttc     960
agttcgcccc tggtcgccat ctcggggggtg gccctccgtt ccttcgacaa ctttgacccc    1020
gtcaccctga gcagctgcca gagagggggag acctacagcc ctgccgagca gagctgcgtg    1080
cac                                                                  1083

<210> SEQ ID NO 15
<211> LENGTH: 1083
<212> TYPE: DNA
<213> ORGANISM: Homo sapiens

<400> SEQUENCE: 15
ggcgaggagg tgtatggcat ccaaatctac acgctggatg agcacctgga gatcgatgct      60
gccatgttga cctccactgc agacacccca ctctgtctac agtgtaagcc cctgaagtat     120
aaggtggtcc gggaccctcc tctccagatg gatgtggcct ccatcctaca tctcaatagg     180
aaattcgtag acatggatct aaatcttggc agtgtgtacc agtattgggt cataactatt     240
tcaggaactg aagagagtga gccatcacct gctgtcacat acatccatgg aagtgggtac     300
tgtggcgatg gcattataca aaaagaccaa ggtgaacaat gcgacgacat gaataagatc     360
aatggtgatg gctgctccct tttctgccga caagaagtct ccttcaattg tattgatgaa     420
cccagccggt gctatttcca tgatggtgat ggggtatgtg aggagtttga acaaaaaacc     480
agcattaagg actgtggtgt ctacacgccc cagggattcc tggatcagtg ggcatccaat     540
gcttcagtat ctcatcaaga ccagcaatgc ccaggctggg tcatcatcgg acagccagca     600
gcatcccagg tgtgtcgaac caaggtgata gatctcagtg aaggcatttc ccagcatgcc     660
```

```
tggtaccctt gcaccatcag ctacccatat tcccagctgg ctcagaccac tttttggctc      720
cgggcgtatt tttctcaacc aatggttgcc gcagctgtca ttgtccacct ggtgacggat      780
gggacatatt atggggacca aaagcaggag accatcagcg tgcagctgct tgataccaaa      840
gatcagagcc acgatctagg cctccatgtc ctgagctgca ggaacaatcc ctgattatc       900 cctgtggtcc atgacctcag ccagcccttc taccacagcc aggcggtacg tgtgagcttc      960
agttcgcccc tggtcgccat tcggggggtg ccctccgtt  ccttcgacaa ctttgacccc     1020
gtcaccctga gcagctgcca gagagggag acctacagcc tgccgagca gagctgcgtg      1080 cac                                                                  1083

<210> SEQ ID NO 16
<211> LENGTH: 465
<212> TYPE: DNA
<213> ORGANISM: Homo sapiens

<400> SEQUENCE: 16
caggagatgc aaggccagtg ctcggttcca acgagctca acagcaacct caaactgcag       60
tgccctgatg gctatgccat agggtcggag tgtgccacct cgtgcctgga ccacaacagc      120
gagtccatca tcctgccaat gaacgtgacc gtgcgtgaca tcccccactg gctgaacccc      180
acacgggtag agagagttgt ctgcactgct ggtctcaagt ggtatcctca ccctgctctg      240
attcactgtg tcaaaggctg tgagcccttc atgggagaca attattgtga tgccatcaac      300
aaccgagcct tttgcaacta tgacggtggg gattgctgca cctccacagt gaagaccaaa      360
aaggtcaccc cattccctat gtcctgtgat ctacaaggtg actgtgcttg tcgggacccc      420
caggcccaag aacacagccg gaaagacctc cggggataca gccat                      465

<210> SEQ ID NO 17
<211> LENGTH: 291
<212> TYPE: PRT
<213> ORGANISM: Mus musculus

<400> SEQUENCE: 17

Asp Met Arg Leu Trp Ser Trp Val Leu Arg Leu Gly Leu Leu Ser Ala
1               5                   10                  15

Ala Leu Gly Cys Gly Leu Ala Glu Arg Pro Arg Val Arg Arg Asp
            20                  25                  30

Pro Arg Ala Val Arg Pro Pro Arg Ala Ala Gly Pro Ala Thr Cys
        35                  40                  45

Ala Thr Arg Ala Ala Arg Gly Arg Arg Ala Ser Pro Pro Pro Pro
    50                  55                  60

Gly Gly Ala Trp Glu Ala Val Arg Val Pro Arg Arg Gln Gln Arg
65                  70                  75                  80

Ala Ala Arg Gly Ala Glu Glu Pro Ser Pro Pro Ser Arg Ala Leu Tyr
            85                  90                  95

Phe Ser Gly Arg Gly Glu Gln Leu Arg Leu Arg Ala Asp Leu Glu Leu
            100                 105                 110

Pro Arg Asp Ala Phe Thr Leu Gln Val Trp Leu Arg Ala Glu Gly Gly
            115                 120                 125

Gln Lys Ser Pro Ala Val Ile Thr Gly Leu Tyr Asp Lys Cys Ser Tyr
        130                 135                 140

Thr Ser Arg Asp Arg Gly Trp Val Met Gly Ile His Thr Thr Ser Asp
145                 150                 155                 160
```

```
Gln Gly Asn Arg Asp Pro Arg Tyr Phe Phe Ser Leu Lys Thr Asp Arg
            165                 170                 175

Ala Arg Lys Val Thr Thr Ile Asp Ala His Arg Ser Tyr Leu Pro Gly
        180                 185                 190

Gln Trp Val His Leu Ala Ala Thr Tyr Asp Gly Arg Leu Met Lys Leu
    195                 200                 205

Tyr Met Asn Gly Ala Gln Val Ala Thr Ser Ala Glu Gln Val Gly Gly
210                 215                 220

Ile Phe Ser Pro Leu Thr Gln Lys Cys Lys Val Leu Met Leu Gly Gly
225                 230                 235                 240

Ser Ala Leu Asn His Asn Phe Arg Gly His Ile Glu His Phe Ser Leu
                245                 250                 255

Trp Lys Val Ala Arg Thr Gln Arg Glu Ile Val Ser Asp Met Glu Thr
            260                 265                 270

Arg Gly Leu His Thr Pro Leu Pro Gln Leu Leu Gln Glu Asn Trp
        275                 280                 285

Asp Asn Val
    290

<210> SEQ ID NO 18
<211> LENGTH: 264
<212> TYPE: PRT
<213> ORGANISM: Mus musculus

<400> SEQUENCE: 18

Val Ser Asp Met Glu Thr Arg Gly Leu His Thr Pro Leu Pro Gln Leu
1               5                   10                  15

Leu Leu Gln Glu Asn Trp Asp Asn Val Lys Arg Thr Trp Ser Pro Met
            20                  25                  30

Lys Asp Gly Asn Ser Pro Gln Val Glu Phe Ser Asn Ala His Gly Phe
        35                  40                  45

Leu Leu Asp Thr Asn Leu Glu Pro Pro Leu Cys Gly Gln Thr Leu Cys
    50                  55                  60

Asp Asn Thr Glu Val Ile Ser Ser Tyr Asn Gln Leu Pro Ser Phe Arg
65                  70                  75                  80

Gln Pro Lys Val Val Arg Tyr Arg Val Val Asn Ile Tyr Asp Asp His
                85                  90                  95

His Glu Asn Pro Thr Val Ser Trp Gln Gln Ile Asp Phe Gln His Gln
            100                 105                 110

Gln Leu Ala Glu Ala Phe Gln His Tyr Asn Ile Ser Trp Glu Leu Glu
        115                 120                 125

Val Leu Asn Ile Asn Ser Ser Ser Leu Arg His Arg Leu Ile Leu Ala
    130                 135                 140

Asn Cys Asp Ile Ser Lys Ile Gly Asp Glu Lys Cys Asp Pro Glu Cys
145                 150                 155                 160

Asn His Thr Leu Thr Gly His Asp Gly Gly Asp Cys Arg Gln Leu Arg
                165                 170                 175

Tyr Pro Ala Phe Met Lys Lys Gln Gln Asn Gly Val Cys Asp Met Asp
            180                 185                 190

Cys Asn Tyr Glu Arg Phe Asn Phe Asp Gly Gly Glu Cys Cys Asp Pro
        195                 200                 205

Asp Ile Thr Asp Val Thr Lys Thr Cys Phe Asp Pro Asp Ser Pro His
    210                 215                 220

Arg Ala Tyr Leu Asp Val Asn Glu Leu Lys Asn Ile Leu Arg Leu Asp
225                 230                 235                 240
```

```
Gly Ser Thr His Leu Asn Ile Phe Phe Ala Asn Ser Ser Glu Glu Glu
                245                 250                 255

Leu Ala Gly Val Ala Thr Trp Pro
            260

<210> SEQ ID NO 19
<211> LENGTH: 362
<212> TYPE: PRT
<213> ORGANISM: Mus musculus

<400> SEQUENCE: 19

Leu Asp Gly Ser Thr His Leu Asn Ile Phe Phe Ala Asn Ser Ser Glu
1               5                   10                  15

Glu Glu Leu Ala Gly Val Ala Thr Trp Pro Trp Asp Lys Glu Ala Leu
            20                  25                  30

Met His Leu Gly Gly Ile Val Leu Asn Pro Ser Phe Tyr Gly Ile Pro
        35                  40                  45

Gly His Thr His Thr Met Ile His Glu Ile Gly His Ser Leu Gly Leu
    50                  55                  60

Tyr His Ile Phe Arg Gly Ile Ser Glu Ile Gln Ser Cys Ser Asp Pro
65                  70                  75                  80

Cys Met Glu Thr Glu Pro Ser Phe Glu Thr Gly Asp Leu Cys Asn Asp
                85                  90                  95

Thr Asn Pro Ala Pro Lys His Lys Phe Cys Gly Asp Pro Gly Pro Gly
            100                 105                 110

Asn Asp Thr Cys Gly Phe His Gly Phe Phe Asn Thr Pro Tyr Asn Asn
        115                 120                 125

Phe Met Ser Tyr Ala Asp Asp Asp Cys Thr Asp Ser Phe Thr Pro Asn
    130                 135                 140

Gln Val Ser Arg Met His Cys Tyr Leu Asp Leu Val Tyr Gln Ser Trp
145                 150                 155                 160

Gln Pro Ser Arg Lys Pro Ala Pro Val Ala Leu Ala Pro Gln Val Val
                165                 170                 175

Gly His Thr Met Asp Ser Val Met Leu Glu Trp Phe Pro Pro Ile Asp
            180                 185                 190

Gly His Phe Phe Glu Arg Glu Leu Gly Ser Ala Cys Asp Leu Cys Leu
        195                 200                 205

Glu Gly Arg Ile Leu Val Gln Tyr Ala Phe Asn Ala Ser Ser Pro Met
    210                 215                 220

Pro Cys Gly Pro Ser Gly His Trp Ser Pro Arg Glu Ala Glu Gly His
225                 230                 235                 240

Pro Asp Val Glu Gln Pro Cys Lys Ser Ser Val Arg Thr Trp Ser Pro
                245                 250                 255

Asn Ser Ala Val Asn Pro His Thr Val Pro Ala Cys Pro Glu Pro
            260                 265                 270

Gln Gly Cys Tyr Leu Glu Leu Glu Phe Arg Tyr Pro Leu Val Pro Glu
        275                 280                 285

Ser Leu Thr Ile Trp Val Thr Phe Val Ser Ser Asp Trp Asp Ser Ser
    290                 295                 300

Gly Ala Val Asn Asp Ile Lys Leu Leu Thr Ile Ser Gly Lys Asn Ile
305                 310                 315                 320

Ser Leu Gly Pro Gln Asn Val Phe Cys Asp Ile Pro Leu Thr Ile Arg
                325                 330                 335

Leu Arg Asp Val Gly Glu Glu Val Tyr Gly Ile Gln Ile Tyr Thr Leu
```

```
                    340                 345                 350
Asp Glu His Leu Glu Ile Asp Ala Ala Met
            355                 360

<210> SEQ ID NO 20
<211> LENGTH: 361
<212> TYPE: PRT
<213> ORGANISM: Mus musculus

<400> SEQUENCE: 20

Gly Glu Glu Val Tyr Gly Ile Gln Ile Tyr Thr Leu Asp Glu His Leu
1               5                  10                  15

Glu Ile Asp Ala Ala Met Leu Thr Ser Thr Val Asp Ser Pro Leu Cys
            20                  25                  30

Leu Gln Cys Lys Pro Leu Gln Tyr Lys Val Leu Arg Asp Pro Pro Leu
        35                  40                  45

Leu Glu Asp Val Ala Ser Leu Leu His Leu Asn Arg Arg Phe Met Asp
    50                  55                  60

Thr Asp Leu Lys Leu Gly Ser Val Tyr Gln Tyr Arg Ile Ile Thr Ile
65                  70                  75                  80

Ser Gly Asn Glu Glu Ser Glu Pro Ser Pro Ala Ala Ile Tyr Thr His
                85                  90                  95

Gly Ser Gly Tyr Cys Gly Asp Gly Val Ile Gln Lys Asp Gln Gly Glu
            100                 105                 110

Glu Cys Asp Asp Met Asn Lys Val Asn Gly Asp Gly Cys Ser Leu Phe
        115                 120                 125

Cys Lys Gln Glu Val Ser Phe Asn Cys Ile Asp Glu Pro Ser Arg Cys
    130                 135                 140

Tyr Phe His Asp Gly Asp Gly Met Cys Glu Glu Phe Glu Gln Lys Thr
145                 150                 155                 160

Ser Ile Lys Asp Cys Gly Val Tyr Thr Pro Gln Gly Phe Leu Asp Gln
                165                 170                 175

Trp Ala Ser Asn Ala Ser Val Ser His Gln Asp Gln Cys Pro Gly
            180                 185                 190

Trp Val Val Ile Gly Gln Pro Ala Ala Ser Gln Val Cys Arg Thr Lys
        195                 200                 205

Val Ile Asp Leu Ser Glu Gly Ile Ser Gln His Ala Trp Tyr Pro Cys
    210                 215                 220

Thr Ile Thr Tyr Pro Tyr Tyr His Leu Pro Gln Thr Thr Phe Trp Leu
225                 230                 235                 240

Gln Thr Tyr Phe Ser Gln Pro Met Val Ala Ala Val Ile Ile His
                245                 250                 255

Leu Val Thr Asp Gly Thr Tyr Tyr Gly Asp Gln Lys Gln Glu Thr Ile
            260                 265                 270

Ser Val Gln Leu Leu Asp Thr Lys Asp Gln Ser His Asp Leu Gly Leu
        275                 280                 285

His Val Leu Ser Cys Arg Asn Asn Pro Leu Ile Ile Pro Val Val His
    290                 295                 300

Asp Leu Ser Gln Pro Phe Tyr His Ser Gln Ala Val His Val Ser Phe
305                 310                 315                 320

Ser Ser Pro Leu Val Ala Ile Ser Gly Val Ala Leu Arg Ser Phe Asp
                325                 330                 335

Asn Phe Asp Pro Val Thr Leu Ser Ser Cys Gln Arg Gly Glu Thr Tyr
            340                 345                 350
```

```
Ser Pro Ala Glu Gln Ser Cys Val His
        355                 360

<210> SEQ ID NO 21
<211> LENGTH: 309
<212> TYPE: PRT
<213> ORGANISM: Mus musculus

<400> SEQUENCE: 21

Cys Gln Arg Gly Glu Thr Tyr Ser Pro Ala Glu Gln Ser Cys Val His
1               5                   10                  15

Phe Ala Cys Gln Ala Ala Asp Cys Pro Glu Leu Ala Val Gly Asn Ala
            20                  25                  30

Ser Leu Asn Cys Ser Ser Asn His His Tyr His Gly Ala Gln Cys Thr
        35                  40                  45

Val Ser Cys Gln Thr Gly Tyr Val Leu Gln Ile Gln Arg Asp Asp Glu
    50                  55                  60

Leu Ile Lys Ser Gln Val Gly Pro Ser Ile Thr Val Thr Cys Thr Glu
65                  70                  75                  80

Gly Lys Trp Asn Lys Gln Val Ala Cys Glu Pro Val Asp Cys Gly Ile
                85                  90                  95

Pro Asp His His His Val Tyr Ala Ala Ser Phe Ser Cys Pro Glu Gly
            100                 105                 110

Thr Thr Phe Gly Arg Arg Cys Ser Phe Gln Cys Arg His Pro Ala Gln
        115                 120                 125

Leu Lys Gly Asn Asn Ser Phe Leu Thr Cys Met Glu Asp Gly Leu Trp
    130                 135                 140

Ser Phe Pro Glu Ala Leu Cys Glu Leu Met Cys Leu Ala Pro Pro Pro
145                 150                 155                 160

Val Pro Asn Ala Asp Leu Gln Thr Ala Arg Cys Arg Glu Asn Lys His
                165                 170                 175

Lys Val Gly Ser Phe Cys Lys Tyr Lys Cys Lys Pro Gly Tyr His Val
            180                 185                 190

Pro Gly Ser Ser Arg Lys Ser Lys Arg Ala Phe Lys Thr Gln Cys
        195                 200                 205

Thr Gln Asp Gly Ser Trp Gln Glu Gly Thr Cys Val Pro Val Thr Cys
    210                 215                 220

Asp Pro Pro Pro Lys Phe His Gly Leu Tyr Gln Cys Thr Asn Gly
225                 230                 235                 240

Phe Gln Phe Asn Ser Glu Cys Arg Ile Lys Cys Glu Asp Ser Asp Ala
                245                 250                 255

Ser Gln Gly Arg Gly Ser Asn Ile Ile His Cys Arg Lys Asp Gly Thr
            260                 265                 270

Trp Ser Gly Ser Phe His Val Cys Arg Glu Met Gln Gly Gln Cys Ser
        275                 280                 285

Ala Pro Asn Gln Leu Asn Ser Asn Leu Lys Leu Gln Cys Pro Asp Gly
    290                 295                 300

Tyr Ala Ile Gly Ser
305

<210> SEQ ID NO 22
<211> LENGTH: 155
<212> TYPE: PRT
<213> ORGANISM: Mus musculus

<400> SEQUENCE: 22
```

```
Arg Glu Met Gln Gly Gln Cys Ser Ala Pro Asn Gln Leu Asn Ser Asn
1               5                   10                  15

Leu Lys Leu Gln Cys Pro Asp Gly Tyr Ala Ile Gly Ser Glu Cys Ala
            20                  25                  30

Ile Ser Cys Leu Asp His Asn Ser Glu Ser Ile Ile Leu Pro Val Asn
            35                  40                  45

Leu Thr Val Arg Asp Ile Pro His Trp Met Asn Pro Thr Arg Val Gln
50                      55                  60

Arg Ile Val Cys Thr Ala Gly Leu Gln Trp Tyr Pro His Pro Ala Leu
65                  70                  75                  80

Ile His Cys Val Lys Gly Cys Glu Pro Phe Met Gly Asp Asn Tyr Cys
                85                  90                  95

Asp Ala Ile Asn Asn Arg Ala Phe Cys Asn Tyr Asp Gly Gly Asp Cys
                100                 105                 110

Cys Thr Ser Thr Val Lys Thr Lys Lys Val Thr Pro Phe Pro Met Ser
            115                 120                 125

Cys Asp Leu Gln Asn Asp Cys Ala Cys Arg Asp Pro Glu Ala Gln Glu
            130                 135                 140

His Asn Arg Lys Asp Leu Arg Gly Tyr Ser His
145                 150                 155

<210> SEQ ID NO 23
<211> LENGTH: 294
<212> TYPE: PRT
<213> ORGANISM: Homo sapiens

<400> SEQUENCE: 23

Asp Met Arg Leu Trp Ser Trp Val Leu His Leu Gly Leu Leu Ser Ala
1               5                   10                  15

Ala Leu Gly Cys Gly Leu Ala Glu Arg Pro Arg Arg Ala Arg Arg Asp
            20                  25                  30

Pro Arg Ala Gly Arg Pro Pro Arg Pro Ala Ala Gly Pro Ala Thr Cys
            35                  40                  45

Ala Thr Arg Ala Ala Arg Gly Arg Arg Ala Ser Pro Pro Pro Pro Pro
50                  55                  60

Pro Pro Gly Gly Ala Trp Glu Ala Val Arg Val Pro Arg Arg Arg Gln
65                  70                  75                  80

Gln Arg Glu Ala Arg Gly Ala Thr Glu Glu Pro Ser Pro Pro Ser Arg
            85                  90                  95

Ala Leu Tyr Phe Ser Gly Arg Gly Glu Gln Leu Arg Leu Arg Ala Asp
            100                 105                 110

Leu Glu Leu Pro Arg Asp Ala Phe Thr Leu Gln Val Trp Leu Arg Ala
            115                 120                 125

Glu Gly Gly Gln Arg Ser Pro Ala Val Ile Thr Gly Leu Tyr Asp Lys
            130                 135                 140

Cys Ser Tyr Ile Ser Arg Asp Arg Gly Trp Val Val Gly Ile His Thr
145                 150                 155                 160

Ile Ser Asp Gln Asp Asn Lys Asp Pro Arg Tyr Phe Phe Ser Leu Lys
                165                 170                 175

Thr Asp Arg Ala Arg Gln Val Thr Thr Ile Asn Ala His Arg Ser Tyr
            180                 185                 190

Leu Pro Gly Gln Trp Val Tyr Leu Ala Ala Thr Tyr Asp Gly Gln Phe
            195                 200                 205

Met Lys Leu Tyr Val Asn Gly Ala Gln Val Ala Thr Ser Gly Glu Gln
210                 215                 220
```

```
Val Gly Gly Ile Phe Ser Pro Leu Thr Gln Lys Cys Lys Val Leu Met
225                 230                 235                 240

Leu Gly Gly Ser Ala Leu Asn His Asn Tyr Arg Gly Tyr Ile Glu His
            245                 250                 255

Phe Ser Leu Trp Lys Val Ala Arg Thr Gln Arg Glu Ile Leu Ser Asp
        260                 265                 270

Met Glu Thr His Gly Ala His Thr Ala Leu Pro Gln Leu Leu Leu Gln
    275                 280                 285

Glu Asn Trp Asp Asn Val
    290

<210> SEQ ID NO 24
<211> LENGTH: 264
<212> TYPE: PRT
<213> ORGANISM: Homo sapiens

<400> SEQUENCE: 24

Leu Ser Asp Met Glu Thr His Gly Ala His Thr Ala Leu Pro Gln Leu
1               5                   10                  15

Leu Leu Gln Glu Asn Trp Asp Asn Val Lys His Ala Trp Ser Pro Met
            20                  25                  30

Lys Asp Gly Ser Ser Pro Lys Val Glu Phe Ser Asn Ala His Gly Phe
        35                  40                  45

Leu Leu Asp Thr Ser Leu Glu Pro Pro Leu Cys Gly Gln Thr Leu Cys
    50                  55                  60

Asp Asn Thr Glu Val Ile Ala Ser Tyr Asn Gln Leu Ser Ser Phe Arg
65                  70                  75                  80

Gln Pro Lys Val Val Arg Tyr Arg Val Asn Leu Tyr Glu Asp Asp
                85                  90                  95

His Lys Asn Pro Thr Val Thr Arg Glu Gln Val Asp Phe Gln His His
            100                 105                 110

Gln Leu Ala Glu Ala Phe Lys Gln Tyr Asn Ile Ser Trp Glu Leu Asp
        115                 120                 125

Val Leu Glu Val Ser Asn Ser Ser Leu Arg Arg Arg Leu Ile Leu Ala
    130                 135                 140

Asn Cys Asp Ile Ser Lys Ile Gly Asp Glu Asn Cys Asp Pro Glu Cys
145                 150                 155                 160

Asn His Thr Leu Thr Gly His Asp Gly Gly Asp Cys Arg His Leu Arg
                165                 170                 175

His Pro Ala Phe Val Lys Lys Gln His Asn Gly Val Cys Asp Met Asp
            180                 185                 190

Cys Asn Tyr Glu Arg Phe Asn Phe Asp Gly Gly Glu Cys Cys Asp Pro
        195                 200                 205

Glu Ile Thr Asn Val Thr Gln Thr Cys Phe Asp Pro Asp Ser Pro His
    210                 215                 220

Arg Ala Tyr Leu Asp Val Asn Glu Leu Lys Asn Ile Leu Lys Leu Asp
225                 230                 235                 240

Gly Ser Thr His Leu Asn Ile Phe Phe Ala Lys Ser Ser Glu Glu Glu
                245                 250                 255

Leu Ala Gly Val Ala Thr Trp Pro
            260

<210> SEQ ID NO 25
<211> LENGTH: 362
<212> TYPE: PRT
```

<213> ORGANISM: Homo sapiens

<400> SEQUENCE: 25

| Leu | Asp | Gly | Ser | Thr | His | Leu | Asn | Ile | Phe | Phe | Ala | Lys | Ser | Ser | Glu |
|1|||||5|||||10|||||15||

| Glu | Glu | Leu | Ala | Gly | Val | Ala | Thr | Trp | Pro | Trp | Asp | Lys | Glu | Ala | Leu |
||||20|||||25|||||30|||

| Met | His | Leu | Gly | Gly | Ile | Val | Leu | Asn | Pro | Ser | Phe | Tyr | Gly | Met | Pro |
|||35|||||40|||||45||||

| Gly | His | Thr | His | Thr | Met | Ile | His | Glu | Ile | Gly | His | Ser | Leu | Gly | Leu |
||50|||||55|||||60||||

| Tyr | His | Val | Phe | Arg | Gly | Ile | Ser | Glu | Ile | Gln | Ser | Cys | Ser | Asp | Pro |
|65|||||70|||||75|||||80|

| Cys | Met | Glu | Thr | Glu | Pro | Ser | Phe | Glu | Thr | Gly | Asp | Leu | Cys | Asn | Asp |
|||||85|||||90|||||95||

| Thr | Asn | Pro | Ala | Pro | Lys | His | Lys | Ser | Cys | Gly | Asp | Pro | Gly | Pro | Gly |
||||100|||||105|||||110|||

| Asn | Asp | Thr | Cys | Gly | Phe | His | Ser | Phe | Phe | Asn | Thr | Pro | Tyr | Asn | Asn |
|||115|||||120|||||125||||

| Phe | Met | Ser | Tyr | Ala | Asp | Asp | Cys | Thr | Asp | Ser | Phe | Thr | Pro | Asn |
||130|||||135|||||140|||

| Gln | Val | Ala | Arg | Met | His | Cys | Tyr | Leu | Asp | Leu | Val | Tyr | Gln | Gly | Trp |
|145|||||150|||||155|||||160|

| Gln | Pro | Ser | Arg | Lys | Pro | Ala | Pro | Val | Ala | Leu | Ala | Pro | Gln | Val | Leu |
|||||165|||||170|||||175||

| Gly | His | Thr | Thr | Asp | Ser | Val | Thr | Leu | Glu | Trp | Phe | Pro | Ile | Asp |
||||180|||||185|||||190|||

| Gly | His | Phe | Phe | Glu | Arg | Glu | Leu | Gly | Ser | Ala | Cys | His | Leu | Cys | Leu |
|||195|||||200|||||205||||

| Glu | Gly | Arg | Ile | Leu | Val | Gln | Tyr | Ala | Ser | Asn | Ala | Ser | Ser | Pro | Met |
||210|||||215|||||220||||

| Pro | Cys | Ser | Pro | Ser | Gly | His | Trp | Ser | Pro | Arg | Glu | Ala | Glu | Gly | His |
|225|||||230|||||235|||||240|

| Pro | Asp | Val | Glu | Gln | Pro | Cys | Lys | Ser | Ser | Val | Arg | Thr | Trp | Ser | Pro |
|||||245|||||250|||||255||

| Asn | Ser | Ala | Val | Asn | Pro | His | Thr | Val | Pro | Ala | Cys | Pro | Glu | Pro |
||||260|||||265|||||270|||

| Gln | Gly | Cys | Tyr | Leu | Glu | Leu | Glu | Phe | Leu | Tyr | Pro | Leu | Val | Pro | Glu |
|||275|||||280|||||285||||

| Ser | Leu | Thr | Ile | Trp | Val | Thr | Phe | Val | Ser | Thr | Asp | Trp | Asp | Ser | Ser |
||290|||||295|||||300||||

| Gly | Ala | Val | Asn | Asp | Ile | Lys | Leu | Leu | Ala | Val | Ser | Gly | Lys | Asn | Ile |
|305|||||310|||||315|||||320|

| Ser | Leu | Gly | Pro | Gln | Asn | Val | Phe | Cys | Asp | Val | Pro | Leu | Thr | Ile | Arg |
|||||325|||||330|||||335||

| Leu | Trp | Asp | Val | Gly | Glu | Glu | Val | Tyr | Gly | Ile | Gln | Ile | Tyr | Thr | Leu |
||||340|||||345|||||350|||

| Asp | Glu | His | Leu | Glu | Ile | Asp | Ala | Ala | Met |
|||355|||||360||

<210> SEQ ID NO 26
<211> LENGTH: 361
<212> TYPE: PRT
<213> ORGANISM: Homo sapiens

<400> SEQUENCE: 26

```
Gly Glu Glu Val Tyr Gly Ile Gln Ile Tyr Thr Leu Asp Glu His Leu
1               5                   10                  15
Glu Ile Asp Ala Ala Met Leu Thr Ser Thr Ala Asp Thr Pro Leu Cys
            20                  25                  30
Leu Gln Cys Lys Pro Leu Lys Tyr Lys Val Val Arg Asp Pro Pro Leu
        35                  40                  45
Gln Met Asp Val Ala Ser Ile Leu His Leu Asn Arg Lys Phe Val Asp
    50                  55                  60
Met Asp Leu Asn Leu Gly Ser Val Tyr Gln Tyr Trp Val Ile Thr Ile
65                  70                  75                  80
Ser Gly Thr Glu Glu Ser Glu Pro Ser Pro Ala Val Thr Tyr Ile His
                85                  90                  95
Gly Ser Gly Tyr Cys Gly Asp Gly Ile Ile Gln Lys Asp Gln Gly Glu
            100                 105                 110
Gln Cys Asp Asp Met Asn Lys Ile Asn Gly Asp Gly Cys Ser Leu Phe
        115                 120                 125
Cys Arg Gln Glu Val Ser Phe Asn Cys Ile Asp Glu Pro Ser Arg Cys
    130                 135                 140
Tyr Phe His Asp Gly Asp Gly Val Cys Glu Glu Phe Glu Gln Lys Thr
145                 150                 155                 160
Ser Ile Lys Asp Cys Gly Val Tyr Thr Pro Gln Gly Phe Leu Asp Gln
                165                 170                 175
Trp Ala Ser Asn Ala Ser Val Ser His Gln Asp Gln Gln Cys Pro Gly
            180                 185                 190
Trp Val Ile Ile Gly Gln Pro Ala Ala Ser Gln Val Cys Arg Thr Lys
        195                 200                 205
Val Ile Asp Leu Ser Glu Gly Ile Ser Gln His Ala Trp Tyr Pro Cys
    210                 215                 220
Thr Ile Ser Tyr Pro Tyr Ser Gln Leu Ala Gln Thr Thr Phe Trp Leu
225                 230                 235                 240
Arg Ala Tyr Phe Ser Gln Pro Met Val Ala Ala Val Ile His Val
                245                 250                 255
Leu Val Thr Asp Gly Thr Tyr Tyr Gly Asp Gln Lys Gln Glu Thr Ile
                260                 265                 270
Ser Val Gln Leu Leu Asp Thr Lys Asp Gln Ser His Asp Leu Gly Leu
            275                 280                 285
His Val Leu Ser Cys Arg Asn Asn Pro Leu Ile Ile Pro Val Val His
        290                 295                 300
Asp Leu Ser Gln Pro Phe Tyr His Ser Gln Ala Val Arg Val Ser Phe
305                 310                 315                 320
Ser Ser Pro Leu Val Ala Ile Ser Gly Val Ala Leu Arg Ser Phe Asp
                325                 330                 335
Asn Phe Asp Pro Val Thr Leu Ser Ser Cys Gln Arg Gly Glu Thr Tyr
                340                 345                 350
Ser Pro Ala Glu Gln Ser Cys Val His
            355                 360
```

<210> SEQ ID NO 27
<211> LENGTH: 309
<212> TYPE: PRT
<213> ORGANISM: Homo sapiens

<400> SEQUENCE: 27

```
Cys Gln Arg Gly Glu Thr Tyr Ser Pro Ala Glu Gln Ser Cys Val His
  1               5                  10                  15

Phe Ala Cys Glu Lys Thr Asp Cys Pro Glu Leu Ala Val Glu Asn Ala
             20                  25                  30

Ser Leu Asn Cys Ser Ser Ser Asp Arg Tyr His Gly Ala Gln Cys Thr
             35                  40                  45

Val Ser Cys Arg Thr Gly Tyr Val Leu Gln Ile Arg Arg Asp Asp Glu
 50                  55                  60

Leu Ile Lys Ser Gln Thr Gly Pro Ser Val Thr Val Thr Cys Thr Glu
 65                  70                  75                  80

Gly Lys Trp Asn Lys Gln Val Ala Cys Glu Pro Val Asp Cys Ser Ile
                 85                  90                  95

Pro Asp His His Gln Val Tyr Ala Ala Ser Phe Ser Cys Pro Glu Gly
                100                 105                 110

Thr Thr Phe Gly Ser Gln Cys Ser Phe Gln Cys Arg His Pro Ala Gln
                115                 120                 125

Leu Lys Gly Asn Asn Ser Leu Leu Thr Cys Met Glu Asp Gly Leu Trp
        130                 135                 140

Ser Phe Pro Glu Ala Leu Cys Glu Leu Met Cys Leu Ala Pro Pro Pro
145                 150                 155                 160

Val Pro Asn Ala Asp Leu Gln Thr Ala Arg Cys Arg Glu Asn Lys His
                165                 170                 175

Lys Val Gly Ser Phe Cys Lys Tyr Lys Cys Lys Pro Gly Tyr His Val
                180                 185                 190

Pro Gly Ser Ser Arg Lys Ser Lys Arg Ala Phe Lys Thr Gln Cys
        195                 200                 205

Thr Gln Asp Gly Ser Trp Gln Glu Gly Ala Cys Val Pro Val Thr Cys
210                 215                 220

Asp Pro Pro Pro Lys Phe His Gly Leu Tyr Gln Cys Thr Asn Gly
225                 230                 235                 240

Phe Gln Phe Asn Ser Glu Cys Arg Ile Lys Cys Glu Asp Ser Asp Ala
                245                 250                 255

Ser Gln Gly Leu Gly Ser Asn Val Ile His Cys Arg Lys Asp Gly Thr
        260                 265                 270

Trp Asn Gly Ser Phe His Val Cys Gln Glu Met Gln Gly Gln Cys Ser
        275                 280                 285

Val Pro Asn Glu Leu Asn Ser Asn Leu Lys Leu Gln Cys Pro Asp Gly
        290                 295                 300

Tyr Ala Ile Gly Ser
305

<210> SEQ ID NO 28
<211> LENGTH: 155
<212> TYPE: PRT
<213> ORGANISM: Homo sapiens

<400> SEQUENCE: 28

Gln Glu Met Gln Gly Gln Cys Ser Val Pro Asn Glu Leu Asn Ser Asn
  1               5                  10                  15

Leu Lys Leu Gln Cys Pro Asp Gly Tyr Ala Ile Gly Ser Glu Cys Ala
             20                  25                  30

Thr Ser Cys Leu Asp His Asn Ser Glu Ser Ile Ile Leu Pro Met Asn
             35                  40                  45

Val Thr Val Arg Asp Ile Pro His Trp Leu Asn Pro Thr Arg Val Glu
 50                  55                  60
```

-continued

```
Arg Val Val Cys Thr Ala Gly Leu Lys Trp Tyr Pro His Pro Ala Leu
65                  70                  75                  80

Ile His Cys Val Lys Gly Cys Glu Pro Phe Met Gly Asp Asn Tyr Cys
                85                  90                  95

Asp Ala Ile Asn Asn Arg Ala Phe Cys Asn Tyr Asp Gly Gly Asp Cys
            100                 105                 110

Cys Thr Ser Thr Val Lys Thr Lys Lys Val Thr Pro Phe Pro Met Ser
        115                 120                 125

Cys Asp Leu Gln Gly Asp Cys Ala Cys Arg Asp Pro Gln Ala Gln Glu
    130                 135                 140

His Ser Arg Lys Asp Leu Arg Gly Tyr Ser His
145                 150                 155
```